(12) United States Patent
Minogue et al.

(10) Patent No.: US 12,090,276 B1
(45) Date of Patent: Sep. 17, 2024

(54) HIGHLY PORTABLE GAS DELIVERY SYSTEMS

(71) Applicant: Michael R. Minogue, South Hamilton, MA (US)

(72) Inventors: Michael R. Minogue, South Hamilton, MA (US); Sarah-Catherine M. Moen, Malden, MA (US)

(73) Assignee: Michael R. Minogue, South Hamilton, MA (US)

( * ) Notice: Subject to any disclaimer, the term of this patent is extended or adjusted under 35 U.S.C. 154(b) by 0 days.

(21) Appl. No.: 18/509,316

(22) Filed: Nov. 15, 2023

(51) Int. Cl.
*A61M 16/06* (2006.01)
*A61M 16/20* (2006.01)

(52) U.S. Cl.
CPC ...... *A61M 16/0627* (2014.02); *A61M 16/208* (2013.01)

(58) Field of Classification Search
CPC ............ A61M 16/0627; A61M 16/208; B63C 11/18–186; B63C 2011/188; B63C 11/22–24; A62B 7/00–04; A62B 9/02–06
USPC .................................................... 128/203.11
See application file for complete search history.

(56) References Cited

U.S. PATENT DOCUMENTS

| | | | |
|---|---|---|---|
| 2,327,995 A | 8/1943 | Bulbulian |
| 2,920,623 A | 1/1960 | Holt |
| 4,119,097 A | 10/1978 | Spector |
| 4,582,054 A | 4/1986 | Ferrer |
| 4,739,913 A | 4/1988 | Moore |
| 5,222,479 A | 6/1993 | Brauer |

(Continued)

FOREIGN PATENT DOCUMENTS

| | | |
|---|---|---|
| AU | 2011200591 A1 | 8/2011 |
| CA | 3096171 | 4/2022 |

(Continued)

OTHER PUBLICATIONS

Harper et al., "Makerspace helps Tyler doctor develop CPR device" Tyler Morning Telegraph, Mar. 25, 2016. https://tylerpaper.com/news/local/makerspace-helps-tyler-doctor-develop-cpr-device/article_70c95da9-2775-593b-95da-9ac6d022f5ef.html.

(Continued)

*Primary Examiner* — Elliot S Ruddie
(74) *Attorney, Agent, or Firm* — Transformative Legal LLC; Len S. Smith

(57) ABSTRACT

Provided are devices for engaging highly portable gas containers are provided that include a mouthpiece component comprising a flexible mouthguard, a variable inlet component that allows gas to flow from two or more sources to the user, or both. In embodiments such a device comprises engagement means for engaging gas container(s), a transition element that comprises an interior flow passage and a substantially rigid or resilient body, and optionally, a lip engagement component. The devices can be used in assemblies/devices that comprise one or more gas containers containing gas, e.g., an oxygen-rich gas and possibly other ingredients, such as nitric oxide, helium, or active pharmaceutical ingredients. In aspects, the components engage a gas container operable as a gas delivery system independently of such components. Also provided are methods of using such devices, e.g., in delivering oxygen to a person exposed to undesirable saliva-transmissible agents, e.g., harmful chemicals or infectious agents.

29 Claims, 4 Drawing Sheets

(56) References Cited

U.S. PATENT DOCUMENTS

| | | | |
|---|---|---|---|
| 5,318,019 | A | 6/1994 | Celaya |
| 5,411,018 | A * | 5/1995 | Rinehart ............... B63C 11/186 128/201.27 |
| 5,979,442 | A | 11/1999 | Orr |
| 6,494,201 | B1 | 12/2002 | Welik |
| 7,051,731 | B1 * | 5/2006 | Rogerson ............ A61M 15/009 128/207.14 |
| 7,341,056 | B1 | 3/2008 | Tucker |
| 8,166,973 | B2 * | 5/2012 | Pan ........................ A62B 7/02 128/205.24 |
| 8,707,954 | B2 | 4/2014 | McCarthy |
| 9,205,206 | B2 | 12/2015 | Hamaguchi |
| 10,398,872 | B2 | 9/2019 | Schatzl |
| 10,556,074 | B2 | 2/2020 | McCarthy |
| 10,857,314 | B2 | 12/2020 | de Kruijf |
| 10,967,203 | B1 | 4/2021 | Emerson |
| 11,260,190 | B1 | 3/2022 | Feld |
| 11,517,701 | B1 | 12/2022 | Emerson |
| 2001/0020470 | A1 | 9/2001 | Zupan |
| 2004/0040556 | A1 | 3/2004 | Fillyaw |
| 2007/0074726 | A1 | 4/2007 | Majer, III |
| 2011/0247623 | A1 | 10/2011 | McCarthy |
| 2013/0199523 | A1 | 8/2013 | Chen |
| 2017/0151406 | A1 | 6/2017 | Booth Wise |
| 2020/0030643 | A1 * | 1/2020 | Griffiths .................. A62B 9/02 |
| 2021/0402220 | A1 | 12/2021 | Tralau |
| 2022/0008674 | A1 | 1/2022 | Sharp |
| 2022/0040434 | A1 | 2/2022 | Jho |
| 2023/0249009 | A1 | 8/2023 | Silva |
| 2023/0263984 | A1 | 8/2023 | McCarthy |

FOREIGN PATENT DOCUMENTS

| | | |
|---|---|---|
| EP | 2666497 A1 | 11/2013 |
| EP | 3048036 A1 | 7/2016 |
| WO | WO2004018045 A1 | 3/2004 |
| WO | WO2014078034 A1 | 5/2014 |

OTHER PUBLICATIONS

Laerdal, Laerdal Pocket Mask with Oxygen Inlet user guide. Laerdal Medical AS 2021. (Year: 2021).

Life Corporation, Life 02 Mini Product Sheet. Retrieved from the internet Nov. 17, 2023. https://www.lifecorporation.com/life-o2-mini.

Novamedic First Aid CPR Mask Kit Amazon product page. Retrieved Nov. 17, 2023. https://www.amazon.com/NOVAMEDIC-Infant-Detachable-Single-Resuscitator/dp/B09Q4HNNYV.

OXY99 Portable Oxygen Cylinder/Can website. Retrieved from the internet Nov. 17, 2023. https://www.oxy99.org/.

Prestan, Prestan CPR Training Face Mask and Adaptor Bundles. Retrieved from the internet Nov. 17, 2023. https://www.prestan.com/products/cpr-training-supplies/training-face-mask-adaptor-bundles/?back=products.

* cited by examiner

HIGHLY PORTABLE GAS DELIVERY SYSTEMS

FIELD OF THE INVENTION

This invention relates to highly portable gas delivery devices and methods of using such gas delivery devices to aid in addressing various conditions.

BACKGROUND OF THE INVENTION

The development of devices to supplement personal oxygen intake dates to the earliest-known attempts at developing underwater breathing devices (around 500 BCE). The development of such devices dramatically increased during the Industrial Revolution, with the first self-contained breathing apparatus for firefighters and the first autonomous open circuit breathing apparatus for underwater applications being developed in the 1870s and 1860s, respectively (e.g., a patent issued in 1889 to John E. Casey and Arthur W. Browne describes an oxygen delivery system including a mouthpiece, oxygen storage component, and delivery tube). Medical applications with gas delivery devices progressed thereafter, with the modern portable metered dose inhaler devices being initially developed throughout the 1950s.

These systems have been significantly refined and expanded upon to the present, and numerous proposals have been made concerning highly portable breathing apparatuses to oxygenate the lungs, particularly in patent disclosures, over the last five decades. Examples of patent disclosures relating to proposed personal gas delivery devices include U.S. Pat. Nos. 4,119,097, 4,582,054, and 8,707,954 (see also U.S. Ser. No. 10/556,074B2, US20230263984, and US20110247623 by the same inventor and Harper, "Makerspace helps Tyler doctor develop CPR device," Tyler Morning Telegraph, Mar. 25, 2016); US Patent Publication Nos. 2001/0020470 and 2022/0008674; Australian Patent Publication AU2011200591A1; and PCT Application WO 2004018045. Other patent disclosures that propose portable oxygen delivery devices or disclose potentially related components include U.S. Pat. Nos. 2,327,995, 2,920,623, 4,739,913, 5,222,479 5,318,019, 5,979,442, 6,494,201, 7,341,056, 9,205,206, 10,398,872, 10,857,314, 10,967,203, 11,260,190, and 11,517,701 (U.S. patent application Ser. No. 17/689,067 is a reportedly a presently unpublished continuation-in-part of U.S. Pat. No. 11,517,701); US Patent Publication Nos. 2001/0020470, 2004/0040556, 2007/0074726, 2013/0199523, 2017/0151406, 2021/0402220, 2022/0040434, 2023/0249009; and non-US patent documents including EP2666497, EP3048036, WO2014078034A1, and CA3096171.

In the 2000s, the use of highly portable personal supplemental oxygen systems became widespread after the launch of Boost Oxygen™ portable oxygen devices in 2007, particularly after the retail chain Sports Authority™ began to carry Boost Oxygen™ 95% oxygen cans in 2012, and even more so after the product was featured on the Shark Tank™ television program in 2019. The aesthetic design of the currently marked Boost Oxygen® system is disclosed in US Design Patent 610,250, issued Feb. 16, 2010. Robert Neuner, the current CEO of Boost Oxygen, obtained a new design patent in 2022 (U.S. D942,612), which illustrates a somewhat similarly designed device. The Boost Oxygen™ devices are not approved or designed for medical use. Accordingly, the contexts in which such devices can be used are limited to non-medical treatment scenarios.

Following the success of the Boost Oxygen® system, several competitors have also started to market similar devices, including LIFE® O2 Mini (lifecorporation.com/life-o2-mini) and OXY 99 (oxy99.org) devices. In some cases, manufacturers of such devices have even suggested extended applications of such portable oxygen delivery devices that allegedly include use in emergency situations (e.g., in the delivery of CPR), but these devices do not appear to have been approved by regulatory authorities for such applications and use of such devices in such settings appears either rare or completely unknown in the relevant medical literature.

The air in the atmosphere contains 21% oxygen, 78% nitrogen, 0.035% carbon dioxide, and other gases. The pressure of the air in the atmosphere is 760 mmHg, and inhalation and exhalation consist of negative and positive pressure of approximately 3 mmHg. The use of oxygen to resuscitate and support individuals in cases ranging from unconsciousness to CPR is a clinical standard to support human life. However, human breaths passed during mouth-to-mouth resuscitation combined with CPR typically contain 16% oxygen and 5% $CO_2$, meaning that CPR methods may often not be effective to sustain life, particularly without injury to a treated person.

Other oxygen or air delivery devices developed specifically for CPR applications are also known (e.g., oxygen masks used with larger gas delivery devices or containers). In some cases, such devices can include additional features such as an external breathing tube component (examples of which include the Prestan Products CPR training mask (prestan.com/products/cpr-training-supplies/training-face-mask-adaptor-bundles/), the Laerdal Pocket Mask (laerdal.com/us/doc/113/Laerdal-Pocket-Mask), and the Novamedic first aid CPR rescue mask (currently marked on Amazon and through other retailers)). However, the application of these types of devices appears to be limited to systems including oxygen sources that are not highly portable, even with the numerous attempts at developing such systems described in the above-listed patent documents. Often such devices are associated with still other components, such as air bag components. However, despite widespread use, air bags (or airbags) attached to a face mask often release only 21% oxygen to a treated person, while providing limited airflow pressure into the lungs.

Despite the long history of efforts to develop such devices and all the above-described efforts aimed at conceiving effective, highly portable oxygen delivery systems, there has yet to be any successful commercial development of a device that has led to any adoption of highly portable oxygen systems for life-saving applications, reflecting that the development of effective highly portable personal systems for delivering oxygen and other supplemental gases for such applications requires the application of inventive ingenuity.

SUMMARY OF THE INVENTION

This document includes a section entitled "CONSTRUCTION PRINCIPLES AND DESCRIPTION OF SELECT TERMS" that readers are encouraged to consult to help properly interpret the disclosure provided in this section and elsewhere here.

This "Summary of the Invention" section ("Summary") briefly describes the elements and characteristics of selected illustrative embodiment(s) of the invention. The brief summaries of such embodiments provided here are primarily intended to illustrate the nature of the invention and, accordingly, the content of this Summary is not intended to be all-inclusive, and the scope of the invention is not limited to, or by, the exemplary aspects of the invention provided in this section. Any of the aspects of the invention described in this section can be combined with any other aspect described in this or any other aspect of this disclosure.

In one set of embodiments, the invention provides gas delivery devices that comprise a mouthpiece component comprising a contoured mouthguard and a highly portable gas container. In aspects, the contoured mouthguard is selectively releasable/attachable to the highly portable gas container by means of an engagement component. In some respects, the release/attachment is configured to be a rapid attachment/release (as discussed further below). In some respects, the mouthpiece is specifically adapted to bind the gas container or several gas containers. Specific binding is also further discussed below, but, briefly, means that either the engagement component is limited to binding a container or containers having a certain feature (e.g., a certain shaped engagement mechanism element, such as having a specific size of threading, a particular type and size of clip engagement, etc.) or that the engagement component of the mouthpiece component binds more quickly or more effectively to the container due to some feature of the container, such as an element of an engagement mechanism that is specifically sized or otherwise designed to engage the engagement component/element of the device. In aspects, the gas container delivers gas through the mouthpiece via pulse delivery. In some respects, the device comprises a transition element that is relatively small (smaller than the gas container, for example), relatively stable (e.g., rigid/resilient), or both.

In another set of embodiments, the invention provides gas delivery devices comprising a variable inlet component. A variable inlet component is a component that is adapted to deliver gases to a treated person/user by (1) a person assisting the user (an "assistant") breathing into at least part of the variable inlet component or (2) by connecting the variable inlet component to a second gas container/gas source that the variable inlet component is adapted to engage. A variable inlet component often is in the form of a tube. In aspects, the variable inlet component comprises two distinct parts, where one of the two parts comprises a flexible section that is collapsible, compressible, or both. In some respects, the variable inlet component is attachable and detachable. In aspects, the overall length is longer than traditional breathing tubes (e.g., is at least 3, at least 4, or at least 5 inches in length when fully extended). In aspects where the variable inlet component comprises a flexible portion, the flexible portion allows an assistant to control the length of the tube when breathing into it (controlling the rate of breath delivery while also ensuring a distance that promotes safety by avoiding inhaling transmissible chemicals or agents, such as fentanyl or viruses). In aspects where the variable inlet tube comprises a removable portion, the removable portion can facilitate cleaning or sterilization, attaching different specifically adapted engagement components, and achieving other benefits/providing for other uses. In aspects, a variable inlet tube can engage or only engages a part of the transition element, such as an access port that forms a part of or is positioned in the transition element, as a means/method for connection with a mouthpiece component.

In another embodiment, the invention provides devices that comprise both (1) a mouthpiece component as described above and (2) a variable inlet component described above. In facets, the mouthpiece component, variable inlet component, or both are detachable from other components of the device (e.g., from the gas container, secondary gas container, or both) or from each other.

The devices of the invention offer numerous benefits to people, including providing a better way to deliver oxygen to those in need thereof than the mouth-to-mouth resuscitation element of traditional CPR (with higher oxygen content, more consistent gas composition delivered, etc.), particularly in situations where other types of oxygen delivery devices are not available (e.g., more than 1, 2, 5, 10, 15, 20, or 25 miles from a hospital, ambulance, etc.). Other benefits of such devise include a significantly lower incidence of choking or biting in treated persons due to the inclusion of a mouthguard component. Still other possible benefits can include, e.g., a significant reduction in the transmission of undesirable material from a targeted/treated person such as transmission of a virus or other microorganism, or undesirable chemical, e.g., fentanyl, to individual(s) assisting such a person. In aspects, the devices and methods of the invention provide new ways of achieving delivery of therapeutic gas(es) (e.g., highly enriched oxygen gas (oxygen rich gas, e.g., about 95% or 92-95% oxygen concentration gas) that may or may not be supplemented with other agent(s) such as helium, carbon dioxide, or nitric oxide) with safe administration and appropriate pressure in a wearer's (treated person's) mouth to, e.g., directly oxygenate the lungs of the targeted person (and, accordingly, to increase red blood cell oxygen content/association, oxygen blood concentration, lung oxygen concentration, etc.).

In aspects, the invention provides kits comprising components for assembling any of the above-described devices, optionally along with one or more gas container(s).

Such devices can be used in several beneficial ways, including as medical devices. Medical applications associated with such devices can include performing life-saving gas delivery methods, e.g., as a replacement/improvement over CPR (e.g., by consistently delivering a higher concentration of oxygen to a user/target or treated person). These devices also can significantly reduce the risk of contamination from transmissible chemicals or biologic agents, such as compounds (e.g., fentanyl), viruses (e.g., coronaviruses), bacteria, and the like. The devices can significantly improve safety by, e.g., significantly reducing the incidence of tongue biting/damage, gum damage, cheek biting damage, jaw damage, teeth damage, or risk/likelihood or severity of choking, etc. (e.g., where the treated person is undergoing a seizure, such as an epileptic seizure, febrile seizure, or other seizure, or is undergoing spasms or uncontrolled movements, such as in the case of poisoning, drug overdose, and the like) An assistant can use the device to provide gas to a target/user by operation of the gas container to deliver gas through a mouthpiece, by blowing into a variable input component, by otherwise causing gas delivery through a variable input component, or by performing a combination of any or all thereof. Given these and other beneficial characteristics, methods can be applied to persons with epilepsy, COPD, and other disorders/conditions described herein.

More specific exemplary embodiments follow.

In one particular aspect, the invention provides devices for providing a modified engagement with a highly portable gas container (e.g., a pressurized gas device, such as a gas canister device, such as the currently marked version of a Boost Oxygen™ device, or a device/system that is substantially similar thereto in terms of e.g., stored gas, gas delivery rate/volume, capacity, size/weight, or a combination thereof) comprising (1) a contoured flexible mouthguard component that comprises (a) a gas outlet and (b) at least right rear and left rear teeth engagement features/components, (2) an engagement component that releasably sealingly engages at least one type of gas container (e.g., by having a structure that rapidly engages and forms an at least substantially airtight/gas-containing seal with the mouthpiece of a gas canister, such as the previously mentioned Boost Oxygen™ devices or similar gas storage/delivery devices), and (3) a transition element positioned between the engagement component and the mouthguard component and that comprises (a) an interior flow passage and (b) a substantially rigid body, a relatively small size (e.g., having no length, width, or depth measure that is greater than the largest dimension of the associated gas container(s) or having no height, width, or depth greater than 18 inches, 15 inches, 12 inches, or 10 inches), or both. The contoured flexible mouthguard component in aspects further comprises a lip engagement component/mouth seal component, which engages the lips of a user's mouth and promotes more effective sealing of the mouth of a user (with respect to retaining delivered gas) when the device is in use. The flexible mouthguard component is typically mostly, generally entirely, substantially entirely, essentially, or entirely composed of a silicone-based material, such as a silicone rubber material, or a material having substantially similar properties in terms of user safety, hardness/softness, etc.

Such devices can be combined with one or more gas delivery/storage devices (e.g., pressurized gas canisters) to form more complex devices (assemblies) or systems or otherwise form a part/component of a larger device or system. In such regard, the invention provides, for example, a device for delivering gas to a user comprising: (1) a gas container comprising (a) an inert and impermeable container material that forms a gas compartment and (b) a stable, compressed, pressurized, aerosol-free, and propellant-free supply of an inhalable gaseous substance suitable for mammalian consumption contained in the gas compartment, the gas compartment having a capacity such that the device can deliver the equivalent of at least about 25 one second continuous release pulses of gas when full, and (c) a selectable gas release component that releases the compressed and pressurized inhalable gaseous substance from the gas container when engaged by the user, and (2) a releasable mouthpiece component that is adapted to engage the gas container and that comprises (a) a contoured flexible mouthguard that comprises (I) a gas outlet and (II) at least right rear and left rear teeth engagement features, (b) an engagement component that releasably sealingly engages the gas container, and (c) a transition element that retains a substantially stable shape in use.

In a related aspect, the invention provides, e.g., a device for delivering gas to a mammalian user (e.g., a human) comprising (1) a gas container, e.g., a gas canister device that is capable of assuming at least one stable vertically oriented position, and that comprises (a) one or more outer horizontal dimensions comprising either an outer length and outer width or, where the device is cylindrical in shape, an outer diameter, (b) an inert and impermeable container material that forms a gas compartment (e.g., a metallic material, such as aluminum or another material that is lightweight, insert, and capable of maintaining the gas under pressurized conditions, such as ≥~100 pound per square inch of pressure (psi/PSI), e.g., ≥~125 psi, or ≥~150 psi or greater, and (c) a stable, compressed, pressurized, aerosol-free, and propellant-free supply of an inhalable gaseous substance suitable for mammalian consumption contained in the gas compartment (at pressure, as noted above), the gas compartment having a capacity such that the device can deliver the equivalent of at least about 25 one second continuous release pulses of gas when full (e.g., ≥~30 pulses, such as about 25-250 pulses, ~30-240 pulses, ~30-210 pulses, or ~25-200 pulses, etc. (e.g., ~50-200, ~50-100, ~50-150, ~30-150, ~30-120, ~30-180, ~40-200, ~40-160, ~75-300, or ~75-150 pulses), and (d) a selectable gas release component that releases the compressed and pressurized inhalable gaseous substance from the gas container when engaged by the user (e.g., a button, dial, knob, lever, or trigger that engages a release valve or other release component(s)), wherein the amount of the gaseous substance released from the gas container is proportional to the amount of time that the user engages the selectable gas release component (i.e., the longer the release component is engaged the more air is released) and (2) a releasable mouthpiece component that is adapted to engage the gas container (e.g., by seal, threading, or other engagement method/means) and that comprises (a) a contoured flexible mouthguard that comprises (I) a gas outlet and (II) at least right rear and left rear teeth engagement features, (b) an engagement component that releasably sealingly engages the gas container, and (c) a transition element comprising one or more outer dimensions and an interior gas flow passage that permits the gaseous substance released from the gas container to flow from the gas container to the gas outlet. In aspects, the transition element can be characterized by (1) comprising a substantially rigid body (i.e., a body that does not change shape significantly during ordinary use), (2) comprising a structure that stays substantially in the same position with respect to the gas container when engaged, (3) has no outer dimension size (including height, length, and width) that is more than five times the size of the largest outer horizontal dimension size of the gas delivery/storage device (also called herein a gas container) (and, accordingly, the transition element is not elongated like a hose).

In aspects, the overall device is noticeably lightweight, e.g., about 2.5 pounds or less, such as about 2 pounds or less, about 1.5 pounds or less, about 1 pound or less, or even less than 1 pound, such as about 0.75, 0.66, 0.5, 0.4, or 0.33 pounds or less. In aspects, the device is suitable for handheld use by most, generally all, or substantially all healthy adults. In aspects, the device can be stably supported in a number of environments on its own. In aspects, a device can, e.g., be vertically oriented ("stand") on a variety of surfaces (e.g., flat or substantially flat surfaces). In this and other respects, devices can be used in a hands-free manner (without the requirement of the user holding the device during use). In aspects, the mouthpiece component is adequately adapted and the overall weight of the device sufficiently low than most, generally, or all users can use the device while inserted into the mouth in a hands-free manner (without supporting the gas storage container). For example, in aspects a gas container can be allowed to "hang" from the user's mouth while the user engages the mouthpiece component, during operation for some, most, or all of a period of use, in aspects without significant discomfort, loss of the device, loss of significant amounts of gas, or a combination thereof.

Due to the lightweight nature of devices of the invention, in aspects, methods can include having such devices available at schools, in ambulances or other EMT deployment, in military exercises or other military situations, in outdoor activities, and for car/home safety. In aspects, such devices are provided with, e.g., other elements of a first aid kit, with fire extinguisher(s), or with other safety-related or emergency use objects/kits.

In another particular aspect, the invention provides the device as described above, wherein the mouthpiece component further comprises at least one access port designed to receive one or more additional gas conveyance components. In aspects, the gas conveyance component may be a variable inlet component (e.g., or another type of supplemental inlet component, such as a supplemental inlet tube, e.g., a breathing tube). In aspects, a kit or device comprises a variable inlet component/tube that provides a means for delivering additional gas to the user, such as oxygen from another gas container or from the mouth of a person assisting the user. In aspects, the supplemental tube is designed to provide gas that is used in combination with a gas container such as currently marketed Boost Oxygen™ devices or substantially similar device(s). In aspects, a device can be operated with or without the gas conveyance component.

In yet another exemplary aspect, the invention provides a device for delivering gas to a user comprising (1) a gas container comprising (a) one or more outer horizontal dimensions comprising either an outer length and outer width or an outer diameter, (b) an inert and impermeable container material that forms a gas compartment, and (c) an amount of an inhalable gaseous substance suitable for mammalian consumption contained in the gas compartment, the gas compartment having a capacity such that the device can deliver the equivalent of at least about 20, ≥~25, ≥~30, ≥~35, ≥~40, or ≥~50, or ≥~25, ≥~40, ≥~60, ≥~80, or ≥~100 one second continuous release pulses of gas when full, and (d) a selectable gas release component that releases the compressed and pressurized inhalable gaseous substance from the gas container when engaged by the user, wherein the amount of the gaseous substance released from the gas container is proportional to the amount of time that the user engages the selectable gas release component; (2) a releasable mouthpiece component that is adapted to engage the gas container and that comprises (a) a gas outlet and (b) at least right rear and left rear teeth engagement features, (c) an engagement component that releasably sealingly engages the gas container, and (d) a transition element comprising one or more outer dimensions and an interior gas flow passage that permits the gaseous substance released from the gas container to flow from the gas container to the gas outlet, wherein (I) no outer dimension size of the transition element is more than five times the size of the largest outer horizontal dimension size of the gas container and (II) the transition element retains a substantially stable shape in use; and (3) a variable inlet component adapted to provide one or more additional substance(s) to the user in addition to the inhalable gaseous substance. In aspects, the variable inlet component comprises a flexible portion that is collapsible, compressible, or both. In aspects, the variable inlet component comprises two portions that can be separated. In aspects, one part of the variable inlet component is specifically adapted to engage one or more secondary gas devices/gas sources. In aspects, the variable inlet component is detachable from the device.

In yet another exemplary aspect, the invention provides a multi-port connection device, comprising (1) a first port adapted to form a selectively releasable connection to a gas container optionally comprising a stable, compressed, pressurized, aerosol-free, and propellant-free supply of an inhalable gaseous substance suitable for mammalian consumption, (2) a second port to which a selectively releasable variable inlet component is attached, (3) a third port adapted to form a selectively releasable connection to a mouthpiece component, and (4) a passageway between the first port, the second port, or both the first and second ports and the third port, such (a) that the inhalable gaseous substance, when present and released from the gas container, can enter the multi-port connection device via the first port and exit the multi-port connection device via the third port (b) gas provided via the variable inlet component can enter the multi-port device via the second port and exit the multi-port connection device via the third port, or (c) gas introduced either via the gas container, the variable inlet component, or both, can enter the multi-port connection device via their respective ports and exit the multi-port connection device via the third port.

In still a further exemplary aspect, the invention provides a multi-port connection device, comprising (1) a first port adapted to form a selectively releasable connection to a gas container optionally comprising a stable, compressed, pressurized, aerosol-free, and propellant-free supply of an inhalable gaseous substance suitable for mammalian consumption, (2) a second port to which a selectively releasable variable inlet component is attached, (3) a third port adapted to form a selectively releasable connection to a mouthpiece component, and (4) a passageway between the first port, the second port, or both the first and second ports and the third port, such (a) that the inhalable gaseous substance, when present and released from the gas container, can enter the multi-port connection device via the first port and exit the multi-port connection device via the third port (b) gas provided via the variable inlet component can enter the multi-port device via the second port and exit the multi-port connection device via the third port, or (c) gas introduced either via the gas container, the variable inlet component, or both, can enter the multi-port connection device via their respective ports and exit the multi-port connection device via the third port.

In an additional exemplary aspect, the invention provides a multi-port connection device, wherein (1) a first port is adapted to form a selectively releasable connection to a gas container optionally comprising a stable, compressed, pressurized, aerosol-free, and propellant-free supply of an inhalable gaseous substance suitable for mammalian consumption and (2) a second port is adapted to form a selectively releasable connection to a mouthpiece component, and (3) a passageway between the first port and the second port, such that the inhalable gaseous substance, when present and released from the gas container, can enter the multi-port connection device via the first port and exit the multi-port connection device via the second port.

In still a further exemplary aspect, the invention provides a kit (a collection of components(s)/device(s)) for delivering one or more sources of gas to a user comprising (1) one or more gas container(s) that is/are each capable of assuming at least one stable vertically oriented position and that comprise(s) (a) one or more outer horizontal dimensions comprising an outer length, an outer width, or an outer diameter, (b) an inert and impermeable container material that forms a gas compartment within the gas container, and (c) optionally a stable, compressed, pressurized, aerosol-free, and propellant-free supply of an inhalable gaseous substance suitable for mammalian consumption contained in the gas compartment, the gas compartment having a capacity such that the device can deliver the equivalent of at least about 25 one-second, continuous release pulses of gas when full, and (d) a selectable gas release component that releases the compressed and pressurized inhalable gaseous substance, when present, from the gas container when engaged by the user, wherein the amount of the gaseous substance released from the gas container is proportional to the amount of time that the user engages the selectable gas release component;

and (2) one or more mouthpiece component(s) adapted to engage, e.g., releasably engage, at least one of the one or more gas container(s) and that each comprise (a) a contoured flexible mouthguard that comprises (I) a gas outlet and (II) at least right rear and left rear teeth engagement features and (b) an engagement component that releasably sealingly engages the gas container.

In some respects, the invention provides more complex devices that comprise such a mouthpiece interface device as a component of a more complex device, where the mouthpiece interface component is in operable association with the gas container/delivery/storage device/component. Such devices also can be described as "operable devices." In aspects, the two different types of devices are provided as a "kit," where a user may assemble the components. In aspects, the mouthpiece component is provided as a stand-alone device but is specifically adapted to engage one or more types of gas delivery/storage devices. For the sake of further illuminating the invention, exemplary aspects of such a gas container component/device will be described in the next several sections.

In yet another illustrative aspect, the invention provides new methods of delivering gaseous substances to the mouth/lungs of a mammalian user comprising (1) placing the mouthpiece of a device having the features of the above-described devices into the mouth of a user such that at least some of the user's teeth engage the right rear and left rear teeth engagement features of the mouthguard component when the user's mouth is closed and (2) having the user or a person assisting the user engages the gas release component to deliver the gas to the user. In some respects, the method is performed by a person assisting the user. In some respects, the user is a person who is unconscious or at risk of becoming unconscious. In some respects, a user is a person having a condition wherein transmission of saliva materials is highly undesired, such as exposure to a chemical (e.g., to a drug, such as fentanyl) or an infectious agent (e.g., a virus, such as a coronavirus or other virus), or the person has epilepsy, asthma, COPD, heart attack or other coronary-related condition, or other condition that makes use of the device highly desirable as compared to existing gas delivery systems.

Exemplary Aspects of the Invention

The following non-limiting list of exemplary aspects of the invention illustrates numerous embodiments of the invention in a summary form, which may further aid readers in understanding the scope of the invention described herein.

Like patent claims, the listed aspects described in the paragraphs of this section may refer to (and, thus, depend on/from) one or more of the other listed paragraphs.

Readers will understand that such references mean that the features/characteristics or steps of such referenced aspects are incorporated into/combined with the referring aspect. For example, if an aspect in a paragraph (e.g., a paragraph indicated by text at the end of the paragraph as aspect 2) refers to another aspect by one or more aspect numbers (e.g., aspect 1 or "any one of aspects 1-3"), it will be understood to include the elements, steps, or characteristics of such referenced aspects (e.g., aspect 1) in addition to those of the aspect in which the reference is made (e.g., if aspect 2 refers to aspect 1, it discloses a composition, method, system, device, etc., including the features of both aspect 1 and aspect 2).

Reference to ranges of aspects should be interpreted as disclosing all such aspects individually, each as unique embodiments of the invention, and in combination with one another as unique embodiment(s) of the invention, according to the presentation provided of such aspects unless such an aspect within such a referenced range is either nonsensical or otherwise contradicted. If a part of an aspect is nonsensical or otherwise contradicted, the aspect should be construed as excluding any contradicted or nonsensical referenced aspect(s). For example, if a dependent aspect Y is directed to specific characteristics of element X, but element X is not included in all the aspects that aspect Y refers to, aspect Y will be interpreted as applying to only those aspects within the referenced list that comprise element X.

It is intended that these listed exemplary aspects begin with the first listed aspect (ASPECT 1) and thereafter be numbered sequentially and incrementally reflected by the inclusion of a reference placed near or at the end of the listed aspect (ASPECT 2, ASPECT, 3, etc.). In case of a missing aspect reference or repeated aspect reference, the order of placement of the actual recited aspect in the list that is associated with the repeated aspect reference or missing aspect reference will control (e.g., if there is an unlabeled aspect located between a first aspect labeled ASPECT 1 and a third aspect labeled aspect "ASPECT 2," the unlabeled aspect should be treated as ASPECT 2, and the aspect labeled as ASPECT 2 treated as ASPECT 3, etc.), and all numbering in the list (including all references to aspects in the list) be interpreted as accordingly modified (e.g., if the fourth aspect in such list was labeled as ASPECT 3, it should be interpreted as being labeled as ASPECT 4, and if such aspect referred to "any one or both of aspect 1 or aspect 2," it should be read as referring to "any one or more of aspects 1-3"). Similarly, if an aspect is misnumbered (e.g., by a number in the sequence being skipped or otherwise missing), readers will similarly construe this list of aspects according to the order of placement of the recited aspects over the numerical references. Further, if one or more of the listed exemplary aspects of the invention in this section fails to reference any other aspects of the invention, such aspect, uncontradicted, should be interpreted as applying to or as capable of being incorporated into any one or more other exemplary aspect(s) provided in this section and if an aspect includes an incomplete reference to other aspects (e.g., "any one or more of aspects 1 to"), such aspect will be interpreted as referring to a list of aspects that incorporates all aspects up to the aspect preceding that aspect or as referring to the first aspect up to the included referenced aspect, as applicable (e.g., for cases where an aspect refers to, e.g., "any one or more of aspects to 29").

In the first exemplary aspect, the invention provides (AA) a device for delivering gas to a user comprising (1) a gas container comprising (a) a stable, compressed, supply of an inhalable gaseous substance ("gas") suitable for mammalian consumption, and (b) a selectable gas release component that releases the compressed and pressurized inhalable gaseous substance from the gas container when engaged by the user, and (2) a mouthpiece component that is adapted to engage the gas container and that comprises (a) a contoured flexible mouthguard that comprises (I) a gas outlet and (II) at least right rear and left rear teeth engagement features, (b) an engagement component that releasably sealingly engages the gas container, and (c) a transition element comprising one or more outer dimensions and an interior gas flow passage that permits the gaseous substance released from the gas container to flow from the gas container to the gas outlet, wherein (I) no outer dimension of the transition element is more than 9 inches in size, (II) no outer dimension size of the transition element is more than five times the size of the largest outer horizontal dimension size of the gas container, or (III) the transition element retains a substantially stable shape in use, or (BB) a device for delivering gas to a user comprising a mouthpiece component that is adapted to engage a highly portable gas container weighing 1.5 pounds or less, the mouthpiece component comprising (a) a contoured flexible mouthguard that comprises (I) a gas inlet that can receive a gas flow from the gas container, (II) a gas outlet through which gas can flow into the mouth of a user, and (III) at least right rear and left rear teeth engagement features, (b) an engagement component that releasably sealingly engages the highly portable gas container, and (c) a transition element that (I) is composed of a flexible material that substantially stable shape at rest so as to maintain the relative position of the mouthpiece component to the highly portable gas container when present, (II) comprises a passageway for the flow of gas from the gas container to the inlet of the mouthpiece component, and (III) comprises a port for engaging a secondary inlet component (e.g., a variable inlet component or other supplemental inlet component), or (CC) a device/system for delivering gas to a user comprising a mouthpiece component comprising (a) a contoured flexible mouthguard that comprises (I) a gas inlet that can receive a gas flow from the gas container, (II) a gas outlet through which gas can flow into the mouth of a user, and (III) at least right rear and left rear teeth engagement features, (b) a first engagement component that is configured to releasably engage one or more highly portable gas containers and form an airtight seal between the highly portable gas container and the engagement component, and (c) a transition element that (I) is composed of a flexible material that substantially stable shape at rest so as to maintain the relative position of the mouthpiece component to the highly portable gas container when present, (II) comprises a passageway for the flow of gas from the gas container to the inlet of the mouthpiece component, and (III) comprises a port for engaging a variable inlet component, (2) a variable inlet component that comprises (a) a flexible portion having that is horizontally and vertically compressible and (b) a second portion that is selectively detachable from the flexible portion and comprises a second engagement component that is adapted to sealingly and releasably engage one or more gas sources, and (3) a highly portable gas container having a weight of less than 1.5 pounds and comprising (a) an inert and impermeable container material that forms a gas compartment and (b) a compressed supply of a compressed oxygen-rich gas contained in the gas compartment, the gas compartment having a capacity such that the device can deliver the equivalent of at least about 100 one second continuous release pulses of the gas when full, and (c) a selectable gas release component that releases the compressed oxygen-rich gas from the gas container when engaged. ASPECT 1.

In another exemplary aspect, the invention provides a system for delivering one or more sources of gas to a user comprising (1) a gas container that is capable of assuming at least one stable vertically oriented position and that comprises an inert and impermeable container material that forms a gas compartment within the gas container; and (2) a mouthpiece component that is adapted to engage the gas container and that comprises (a) a contoured flexible mouthguard that comprises (1) a gas outlet and (11) at least right rear and left rear teeth engagement features, (b) an engagement component that releasably sealingly engages the gas container, (c) at least one access port designed to receive one or more variable inlet component(s), wherein the mouthpiece component is optionally releasable and re-attachable to the gas container. ASPECT 2.

In another exemplary aspect, the invention provides a device for delivering a gas to a user comprising (1) a gas container that comprises an inert and impermeable container material that forms a gas compartment within the gas container, (2) a mouthpiece component that is adapted to engage the gas container and that comprises (a) a contoured flexible mouthguard that comprises (I) a gas outlet and (II) at least right rear and left rear teeth engagement features, (b) an engagement component that sealingly engages the gas container, and (3) a supplemental inlet component that engages the mouthpiece component and that provides a way to provide alternative or supplemental gas delivery to the user independent of the gas container (a secondary pathway (secondary flow path), where the flow from the gas container (aka, first gas container) to the mouthpiece component may be referred to as the primary pathway). ASPECT 3.

In another exemplary aspect, the invention provides a gas delivery device comprising (1) a gas outlet, (2) at least two inlet ports, and (3) at least one passageway connecting the gas outlet with at least one of the at least two inlet ports, wherein the first inlet port is designed to selectively connect to a source of pressurized gas, and the second inlet port is an access port designed to selectively connect to a variable inlet component, and wherein the at least one passageway facilitates the passage of gas from the source of pressurized gas, the variable inlet component, or both, to the gas outlet. ASPECT 4.

In another aspect, the invention provides a device for delivering gas to a user comprising (1) a contoured flexible mouthguard that comprises (a) a gas outlet and (b) at least right rear and left rear teeth engagement features, (2) an engagement component that is adapted to rapidly releasably sealingly engage one or more highly portable and vertically oriented gas delivery devices, and (3) a transition element that is (a) less than 9 inches in size in any dimension or (b) is either substantially rigid or substantially resilient in shape. ASPECT 5.

In another aspect, the invention provides a device for providing a modified engagement with a highly portable gas container and release device comprising (1) a contoured flexible mouthguard that comprises (a) a gas outlet and (b) at least right rear and left rear teeth engagement features, (2) an engagement component that is adapted to releasably sealingly engage at least one type of gas container, and (3) a transition element comprising (a) an interior flow passage and (b) a substantially rigid body. ASPECT 6.

In another aspect, the invention provides a device for delivering gas to a user comprising: (1) means for storing a gaseous substance ("gas storage means"), (2) means for selectively releasing the gaseous substance ("gas release means") and (3) a releasable mouthpiece component comprising (a) a contoured flexible mouthguard that comprises (I) a gas outlet and (II) means for engaging the teeth of a user, (b) means for releasably sealingly engaging the gas storage means ("engagement means"), and (c) a transition element comprising a substantially rigid/resilient body that maintains its position with respect to the gas storage means. ASPECT 7.

In an exemplary aspect, the invention provides a multi-port connection device/component or a collection of multi-port connection device(s)/component(s) for use with a highly portable gas container, it or each thereof comprising a first port operating as a gas inlet port, a second port operating as a gas outlet port, and a passageway between the first port and the second port, wherein the first port, the second port, or both the first and the second ports are adapted to provide (e.g., adapted to provide specifically) a selectively releasable connection to or are connected to (1) a source of pressurized gas (e.g., a gas container, such as one or more particularly gas container(s), such as, e.g., one or more currently marketed Boost Oxygen™ devices or device (s) substantially similar thereto); (2) a gas delivery component (e.g., a mouthpiece component such as described above or anywhere else in this disclosure or other suitable means for delivery of gas to a user); or (3) both (i.e., either). ASPECT 8.

In an exemplary aspect, the invention provides a multi-port connection device for use with a highly portable gas container, wherein (1) a first port is adapted to form a selectively releasable connection to a gas container optionally comprising a stable, compressed, pressurized, aerosol-free, and propellant-free supply of an inhalable gaseous substance suitable for mammalian consumption and (2) a second port is adapted to form a selectively releasable connection to a mouthpiece component, and (3) a passageway between the first port and the second port, such that the inhalable gaseous substance, when present and released from the gas container, can enter the multi-port connection device via the first port and exit the multi-port connection device via the second port. ASPECT 9.

In an exemplary aspect, the invention provides a multi-port connection device for use with a highly portable gas container, comprising (1) a first port adapted to form a selectively releasable connection to a gas container optionally comprising a stable, compressed, pressurized, aerosol-free, and propellant-free supply of an inhalable gaseous substance suitable for mammalian consumption, (2) a second port adapted to form a selectively releasable connection to a variable inlet component, (3) a third port adapted to form a selectively releasable connection to a mouthpiece component, and (4) a passageway between the first port, the second port, or both the first and second ports and the third port, such (a) that the inhalable gaseous substance, when present and released from the gas container, can enter the multi-port connection device via the first port and exit the multi-port connection device via the third port (b) gas provided via the variable inlet component can enter the multi-port device via the second port and exit the multi-port connection device via the third port, or (c) gas introduced either via the gas container, the variable inlet component, or both, can enter the multi-port connection device via their respective ports and exit the multi-port connection device via the third port. ASPECT 10.

In one exemplary aspect, the invention provides a device for delivering gas to a user comprising (1) a highly portable gas container, (2) a gas delivery component that allows for flow of gas into the mouth of a user, and (3) a variable inlet component that sealingly engages the gas delivery component and comprises (a) a flexible component that is collapsible, compressible, or both and comprises a gas flow passage through which gas can flow to the gas delivery component and (b) a detachable interface component that is substantially more rigid, more resilient, or both, in shape, than the flexible component, wherein the variable inlet component is adapted to receive manual blowing from a user and to engage one or more gas delivery devices, wherein optionally the length of the flexible component (here, length meaning the largest dimension of the device) when not collapsed is at least about 4, 5, or 6 inches long (e.g., is about 3-9 inches, about 3.5-7 inches, about 3.75-7.5 inches, about 4-8 inches, or about 4-6 inches long), and further optionally also or alternatively where the flexible component/portion is longer than the interface portion. ASPECT 11.

In one exemplary aspect, the invention provides a device for delivering gas to a user comprising (1) a highly portable gas container, (2) a mouthpiece component comprising a flexible contoured mouthguard component comprising a gas outlet that permits the flow of gas into the mouth of a user that is engaging the mouthguard and a gas flow passageway that permits gas to flow to the gas outlet, and (3) a variable inlet component that comprises (a) a flexible component that sealing engages the mouthpiece component, comprises a gas flow passageway, and is collapsible, compressible, or both, and (b) a detachable interface component that is substantially more rigid than the flexible component, wherein the variable inlet component is adapted to receive manual blowing from a user and to engage one or more gas delivery devices, wherein optionally the length of the flexible component when not collapsed is at least about 5 inches long. ASPECT 12.

In one exemplary aspect, the invention provides a device for delivering gas to a user comprising (1) a gas container comprising (a0 an inert and impermeable container material that forms a gas compartment and (b) an amount of an inhalable gaseous substance suitable for mammalian consumption contained in the gas compartment, optionally the gas compartment having a capacity such that the device can deliver the equivalent of at least about 50, 100, 150, 200, or 250 (e.g., 40-400, 30-300, 50-500, 250-350, or 250-500) one second continuous release pulses of gas when full, and (c) a selectable gas release component that releases the compressed and pressurized inhalable gaseous substance from the gas container when engaged by the user, wherein the amount of the gaseous substance released from the gas container is proportional to the amount of time that the user engages the selectable gas release component; (2) a releasable mouthpiece component that is adapted to engage the gas container and that comprises (a) a gas outlet and (b) at least right rear and left rear teeth engagement features, (c) an engagement component that releasably sealingly engages the gas container, and (d) a transition element comprising one or more outer dimensions and an interior gas flow passage that permits the gaseous substance released from the gas container to flow from the gas container to the gas outlet, wherein (I) no outer dimension size of the transition element is more than five times the size of the largest outer horizontal dimension size of the gas container or (II) the transition element retains a substantially stable shape in use; and (3) a variable inlet component that is attached to a second gas container that when selected delivers one or more additional substance(s) to the user in addition to the inhalable gaseous substance. ASPECT 13.

In one aspect, the invention provides a variable inlet component (e.g., a breathing tube) adapted for use with one or more highly portable gas containers, wherein the variable inlet component comprises (1) an inlet end adapted to receive one or more substances from manual user blowing or from a gas container (a second gas container, where applicable) and (2) an outlet end component adapted for allowing the one or more substances to exit the variable inlet component and pass to an engaged gas delivery component and comprising a body that is at least mostly flexible and either collapsible, compressible, or both, wherein the inlet end portion and outlet end portion are optionally detachable from each other. ASPECT 14.

In one aspect, the invention provides a device of any one or more of aspects 1-14, wherein the gas container is a container that can assume at least one stable, vertically oriented (upright) position when placed on a flat or substantially flat surface. ASPECT 15.

In one aspect, the invention provides a device of any one or more of aspects 1-15, wherein prior to use, the container contains a stable, compressed/pressurized, and typically aerosol-free and propellant-free supply of an inhalable gaseous substance suitable for mammalian consumption contained in the gas compartment. ASPECT 16.

In one aspect, the invention provides a device of any one or more of aspects 1-16, wherein the gas container comprises or is associated with a selectable gas release component that releases the compressed and pressurized inhalable gaseous substance from the gas container when engaged by the user, optionally in a pulse delivery manner, optionally wherein the amount of the gaseous substance released from the gas container is substantially proportional to the amount of time that the user engages the selectable gas release component. ASPECT 17.

In one aspect, the invention provides a device of any one or more of aspects 1-17, wherein the gas container comprises one or more gas compartments that have a capacity of at least about 20, ≥~25, ≥~30, ≥~35, ≥~40, or ≥~50, or ≥ ~25, ≥~40, ≥~60, ≥~80, or ≥~100 one-second continuous release pulses of gas when full. ASPECT 18.

In one aspect, the invention provides a device of aspect 18, wherein the gas container comprises one or more gas compartments that have a capacity of at least about 125, e.g., ≥~150, ≥~175, ≥~200, ≥~220, ≥~250, or ≥~280 (e.g., ~80-320, 90-270, 100-300, 200-500, 200-400, 200-350, 200-300, 220-320, 220-270, 250-400, 250-350, or 250-300) one-second continuous release pulses of gas when full. ASPECT 19.

In one aspect, the invention provides a device of any one or more of aspects 1-19, wherein the gas container, when separated from the mouthpiece component, is still independently operable as a gas delivery device. ASPECT 20.

In one aspect, the invention provides a device of aspect 20, wherein the gas container comprises a second mouthpiece that can be used when the gas container is not attached to the mouthpiece component, wherein the second mouthpiece optionally does not cover the nose of a user in use. ASPECT 21.

In one aspect, the invention provides a device of any one or more of aspects 1-21, wherein the right rear teeth engagement component and the left rear teeth engagement component are separated from each other. ASPECT 22.

In one aspect, the invention provides a device of any one or more of aspects 1-22, wherein no outer dimension of the transition element is more than three times the size of the largest outer horizontal dimension of the gas container. ASPECT 23.

In one aspect, the invention provides a device of aspect 23, wherein no outer dimension of the transition element is more than two times the size of the largest outer horizontal dimension of the gas container. ASPECT 24.

In one aspect, the invention provides a device of any one or more of aspects 1-24, wherein the gas container has a capacity of 0.5-20 L with respect to pure or substantially pure oxygen gas. ASPECT 25.

In one aspect, the invention provides a device of aspect 25, wherein the gas container has a capacity of 1-15 L with respect to pure or substantially pure oxygen gas. ASPECT 26.

In one aspect, the invention provides a device of aspect 26, wherein the gas container has a capacity of 4-12 L. ASPECT 27.

In one aspect, the invention provides a device of aspect 27, wherein the gas container has a capacity of 5-10 L (e.g., about 5 L, about 7 L, about 8 L, or about 10 L or about 7.5-10 L). ASPECT 28.

In one aspect, the invention provides a device of any one or more of aspects 1-28, wherein each of the right rear teeth engagement component and the left rear teeth engagement component are at least mostly composed of one or more types of silicone rubber. ASPECT 29.

In one aspect, the invention provides a device of any one or more of aspects 1-29, wherein the gas container can deliver 50-350 one-second continuous release pulses of gas when full, such as 100-300, 100-250, 100-225, or 100-200 pulses. ASPECT 30.

In one aspect, the invention provides a device of any one or more of aspects 1-30, wherein the gas container can deliver 125-250, 150-275, 200-300, 200-400, 200-500, 220-400, 250-400, 250-350, 240-300, 250-300, or 200-300 one-second continuous release pulses of gas when full. ASPECT 31.

In one aspect, the invention provides a device of any one or more of aspects 1-31, wherein the gas comprises 35%-100% oxygen. ASPECT 32.

In one aspect, the invention provides a device of any one or more of aspects 1-31, wherein the gas comprises 35%-99.9% oxygen. ASPECT 33

In one aspect, the invention provides a device of any one or more of aspects 1-31, wherein the gas comprises 35%-95% or 35%-98% oxygen. ASPECT 34.

In one aspect, the invention provides a device of any one or more of aspects 1-31, wherein the gas comprises 55%-100% oxygen. ASPECT 35.

In one aspect, the invention provides a device of any one or more of aspects 1-31, wherein the gas comprises 55%-99.9% oxygen. ASPECT 36.

In one aspect, the invention provides a device of any one or more of aspects 1-31, wherein the gas comprises 55%-95% or 55%-98% oxygen. ASPECT 37.

In one aspect, the invention provides a device of any one or more of aspects 1-31, wherein the gas comprises 90%-99.9% oxygen. ASPECT 38.

In one aspect, the invention provides a device of any one or more of aspects 1-31, wherein the gas comprises 90%-95% or 90%-98% oxygen. ASPECT 39.

In one aspect, the invention provides a device of any one or more of aspects 1-31, wherein the oxygen concentration in the gas is 92.4%-95.4% (e.g., 92-95%) or 92.4%-98.4%. ASPECT 40.

In one aspect, the invention provides a device of any one or more of aspects 1-31, wherein the gas comprises at least 0.001% nitric oxide. ASPECT 41.

In one aspect, the invention provides a device of any one or more of aspects 1-41, wherein the mouthpiece component comprises a lip seal component. ASPECT 42.

In one aspect, the invention provides a device of any one or more of aspects 1-42, wherein the total weight of the device is less than 2.5 pounds. ASPECT 43.

In one aspect, the invention provides a device of any one or more of aspects 1-42, wherein the total weight of the device is less than 2 pounds. ASPECT 44.

In one aspect, the invention provides a device of any one or more of aspects 1-42, wherein the total weight of the device is less than 1.5 pounds. ASPECT 45.

In one aspect, the invention provides a device of any one or more of aspects 1-42, wherein the total weight of the device is less than 1 pound. ASPECT 46.

In one aspect, the invention provides a device of any one or more of aspects 1-46, wherein the mouthpiece component/mouthguard has been specifically adapted for use by a specific user. ASPECT 47.

In one aspect, the invention provides a device of any one or more of aspects 1-47, wherein the device is adapted to prevent/comprises one or more components that prevent the backflow of gas from the user to the gas container during use. ASPECT 48.

In one aspect, the invention provides a device of any one or more of aspects 1-48, wherein the flow rate of gas from the device is about 50 mL to about 500 mL per second, such as about 100-350 mL per sec. when the gas release component is engaged. ASPECT 49.

In one aspect, the invention provides a device of any one or more of aspects 1-49, wherein the device comprises at least one access port that can be selectively open or selectively closed, wherein when open, the access port can receive one or more materials therethrough, and when closed, is sufficiently sealed so as to keep at least about 80% of the inhalable gaseous substance released from the gas container from exiting the system via the access port. ASPECT 50.

In one aspect, the invention provides a device of any one or more of aspects 1-49, wherein the device comprises at least one access port that can be selectively open or selectively closed, and wherein when open, the access port can receive one or more materials therethrough, and when closed, is sufficiently sealed so as to keep at least about 90% of the inhalable gaseous substance released from the gas container from exiting the system via the access port. ASPECT 51.

In one aspect, the invention provides a device of any one or more of aspects 1-49, wherein the device comprises at least one access port that can be selectively open or selectively closed, wherein when open, the access port can receive one or more materials therethrough, and when closed, is sufficiently sealed so as to keep at least about 95% (e.g., ≥98%, ≥99%, ≥99.5%, or ≥99.9%) of the inhalable gaseous substance released from the gas container from exiting the system via the access port. ASPECT 52.

In one aspect, the invention provides a device of any one or more of aspects 1-52 wherein the device is adapted to prevent/comprises one or more components that prevent the backflow of gas from the user to the gas container during use. ASPECT 53.

In one aspect, the invention provides the gas delivery device of one or both of aspect 52 or aspect 53, wherein at least one of the at least two inlet ports can be selectively open or closed. ASPECT 53.

In one aspect, the invention provides the gas delivery device of any one or more of 1-54, wherein the source of pressurized gas is a gas container capable of assuming at least one stable vertically oriented position. ASPECT 54.

In one aspect, the invention provides the gas delivery device of one or more of aspects 1-55, wherein the only gas delivery component that delivers gas to the mouth of a user is a mouthpiece component. ASPECT 56.

In one aspect, the invention provides a device of any one or more of aspects 1-56, wherein the device further comprises means for engaging the lip to seal the mouth better ("lip sealing means"). ASPECT 57.

In one aspect, the invention provides a device of any one or more of aspects 1-57, wherein the comprises gas backflow prevention means. ASPECT 58.

In aspects, the invention provides a device according to any one or more of aspects 1-58, wherein the device comprises a variable inlet component that is sealingly engaged to and in fluid communication with a second gas container that comprises one or more additional gaseous substance(s) that are delivered via the variable inlet component to a user, wherein at least one of the one or more additional substance(s) provided by the variable inlet component is at least generally, at least substantially, at least essentially, or is the same inhalable gaseous substance delivered from or by the gas container (the primary gas container). ASPECT 59.

In aspects, the invention provides a device according to any one or more of aspects 1-58, wherein the device comprises a variable inlet component that is sealingly engaged to and in fluid communication with a second gas container that comprises one or more additional gaseous substance(s) that are delivered via the variable inlet component to a user, wherein at least one of the one or more additional substance(s) provided by the variable inlet component is detectably or significantly different from the inhalable gaseous substance delivered from or by the gas container. ASPECT 60.

In aspects, the invention provides a device according to any one or more of aspects 1-60, wherein the device comprises a variable inlet component that comprises (a) a flexible component that sealing engages the mouthpiece component, comprises a gas flow passageway, and is collapsible, compressible, or both, and (b) a detachable interface component, where the detachable interface component is dish-washable, autoclavable, or both. ASPECT 61.

In aspects, the invention provides a device according to any one or more of aspects 1-61, wherein the gas container is disposable. ASPECT 62.

In aspects, the invention provides a device according to any one or more of aspects 1-61, wherein the gas container is recyclable. ASPECT 63.

In aspects, the invention provides a device according to any one or more of aspects 1-61, wherein the gas container is reusable. ASPECT 64.

In aspects, the invention provides a device according to any one or more of aspects 1-64, wherein the device comprises a variable inlet component and wherein the variable inlet component comprises a mechanism for opening an access port upon engagement. ASPECT 65.

In one aspect, the invention provides a device according to any one or more of aspects 1-65, wherein the variable inlet component of one or more of aspects 140-142, the variable inlet component comprising an inlet end that is engageable by a person that interacts with the device to introduce a gaseous substance into the variable inlet component. ASPECT 66.

In one aspect, the invention provides a device according to any one or more of aspects 1-66, wherein the device comprises a variable inlet component, wherein the variable inlet component comprises an inlet end that is orally engageable by a person assisting with/using the device (e.g., is adapted for placement between the lips of or at least partially within the mouth of a user of a device so as to, for example, facilitate an assistant blowing a breath or a treated person exhaling a breath into the variable inlet component interior compartment). ASPECT 67.

In one aspect, the invention provides a device according to any one or more of aspects 1-67, wherein the device comprises a variable inlet component, wherein the variable inlet component comprises an inlet end and wherein when a substance is introduced into the variable inlet component inlet end, the interior compartment is capable of maintaining at least about 80% of the substance (e.g., ≥~85%, ≥~92.5%, or ≥~95% of the substance) introduced into the inlet end until it passes through the outlet end when the inlet end and outlet end are each otherwise sealed. ASPECT 68.

In one aspect, the invention provides a device according to any one or more of aspects 1-68, wherein the device comprises a variable inlet component, wherein the variable inlet component comprises an inlet end and wherein when a substance is introduced into the variable inlet component inlet end, the enclosed interior compartment can maintain at least about 97.5% (e.g., ≥98%, ≥99%, 99.5%, or ≥99.9%) of the substance introduced into the inlet end until it passes through the outlet end when the inlet end and outlet end are each otherwise sealed. ASPECT 69.

In one aspect, the invention provides a device according to any one or more of aspects 1-69, wherein the device comprises a variable inlet component, wherein the variable inlet component comprises an inlet end and wherein when a substance is introduced into the variable inlet component inlet end, the enclosed interior compartment can maintain at least about 99% (e.g., ≥99.5% or ≥99.9%) of the substance introduced into the inlet end until it passes through the outlet end when the inlet end and outlet end are each otherwise sealed. ASPECT 70.

In one aspect, the invention provides a device according to any one or more of aspects 1-70, wherein the device comprises a variable inlet component comprising an inlet end and an outlet end, wherein the device comprises an access port that attaches to the variable inlet component, and wherein the access port that attaches to the variable inlet component is adapted to prevent the backflow of material into the variable inlet component once it has exited the outlet end of the variable inlet component and passed through the access port. ASPECT 71.

In one aspect, the invention provides a device according to any one or more of aspects 1-71, wherein the device comprises a variable inlet component, wherein the variable inlet component is a removable inlet tube. ASPECT 72.

In one aspect, the invention provides a device according to any one or more of aspects 1-72, wherein the device comprises a variable inlet component comprising an inner gas flow passage, wherein the maximum diameter, width, or height of the inner gas flow passage is between about 2 mm and about 25 mm (e.g., about 3-21, about 4-20, about 5-15, or about 5-20 mm). ASPECT 73.

In one aspect, the invention provides a device according to any one or more of aspects 1-73, wherein the device comprises a variable inlet component, wherein the device comprises a fitting that is used to attach the variable inlet component to the rest of the device, a second gas container (gas delivery source), or both. ASPECT 74.

In one aspect, the invention provides a device according to any one or more of aspects 1-74, wherein the device comprises an oral engagement mechanism suitable for allowing/adapted to a user to introduce material into the variable inlet component by mouth. ASPECT 75.

In one aspect, the invention provides a device according to any one or more of aspects 1-75, wherein the device comprises is an oral engagement mechanism, wherein the oral engagement mechanism is releasably attached to another part of the variable inlet component. ASPECT 76.

In one aspect, the invention provides a device according to any one or more of aspects 1-76, wherein the device comprises is an oral engagement mechanism, wherein the oral engagement mechanism is an oral engagement tube having an inlet end and an outlet end, wherein the outlet end of the oral engagement tube is fixedly attached to the inlet end of the variable inlet component. ASPECT 77.

In one aspect, the invention provides a device according to any one or more of aspects 1-77, wherein the device comprises a variable inlet component comprising an inlet end and an outlet end, wherein the inlet end of the variable inlet component is suitable for allowing a user to introduce material into the device by mouth. ASPECT 78.

In one aspect, the invention provides a device according to any one or more of aspects 1-78, wherein the device comprises a variable inlet component comprising an inlet end and an outlet end, wherein the inlet end of the variable inlet component comprises a threaded section/element (is threaded) such that it can engage one or more other parts of the device by a screwing mechanism. ASPECT 79.

In one aspect, the invention provides a device according to any one or more of aspects 1-79, wherein the device comprises a variable inlet component that engages a second gas container, wherein the second gas container has one or more feature of the gas container (primary gas container) as described in any of the preceding aspects (e.g., comprises a highly portable oxygen container, such as a currently marketed Boost Oxygen™ device). ASPECT 80.

In one aspect, the invention provides a device according to any one or more of aspects 1-80, wherein the device comprises a variable inlet component and wherein the variable inlet component comprises a transitional element facilitating the attachment of the variable inlet component to another device or system. ASPECT 81

In one aspect, the invention provides a device according to any one or more of aspects 1-81, wherein the device comprises a variable inlet component and wherein the variable inlet component has a length that is at least about two times the length of the transition element. ASPECT 82.

In one aspect, the invention provides a device according to aspect 82, wherein the variable inlet component has a length that is at least about five times the length of the transition element. ASPECT 83.

In one aspect, the invention provides a device according to any one or more of aspects 1-83, wherein the device comprises a variable inlet component, wherein the body of the variable inlet component is (a) expandable so as to comprise the ability to detectably or significantly expand in length, (b) collapsible so as to comprise the ability to detectably or significantly decrease in length, or (c) reversibly expandible and collapsible such that the body of the variable inlet component can both detectably or significantly expand and detectably or significantly collapse making the length of the body reversibly detectably or significantly longer and shorter, respectively. ASPECT 84.

In one aspect, the invention provides a device comprising a variable inlet component of aspect 84, wherein at least a portion of the body of the variable inlet component is reversibly expandable and collapsible, and wherein the length of the body when in a fully expanded configuration is at least about 50% longer than the length of the portion of the body when the portion of the body is in a fully collapsed configuration. ASPECT 85.

In one aspect, the invention provides a device comprising a variable inlet component according to aspect 85, wherein the length of the body portion when in a fully expanded configuration is at least about two times longer the body when the body portion is in a fully collapsed configuration. ASPECT 86.

In one aspect, the invention provides a device comprising a variable inlet component according to aspect 86, wherein the length of the body portion when in a fully expanded configuration is at least about three times longer than the length of the body portion when the body portion is in a fully collapsed configuration. ASPECT 87.

In one aspect, the invention provides a device comprising a variable inlet component according to aspect 87, wherein the length of the body portion when in a fully expanded configuration is at least about three times longer than the length of the body portion when the body portion is in a fully collapsed configuration. ASPECT 88.

In one aspect, the invention provides a device according to any one or more of aspects 1-89, wherein the device comprises a variable inlet component, and wherein least a portion of the variable inlet component is replaceable/removable/interchangeable. ASPECT 89.

In one aspect, the invention provides a device comprising a variable inlet component of aspect 89, wherein at least a portion of the variable inlet component is disposable. ASPECT 90.

In one aspect, the invention provides a device comprising a variable inlet component of aspect 89, wherein the entirety of the variable inlet component is replaceable/interchangeable/removable, disposable, or both. ASPECT 91.

In one aspect, the invention provides a device according to any one or more of aspects 1-91, wherein the device comprises a variable inlet component, and wherein the variable inlet component is comprised of at least two detectably or significantly different materials. ASPECT 92 (e.g., in terms of composition, stiffness, hardness, density, or a combination thereof).

In one aspect, the invention provides a device according to any one or more of aspects 1-92, wherein the device comprises a variable inlet component, wherein the variable inlet component comprises a flexible section, wherein the flexible section mostly, generally, substantially, or only is made up of polyvinyl chloride (PVC), polyurethane, silicone, vinyl, nasal cannula tubing, rubber, plastic, metal, or any another material suitable for a tube designed for providing a substance to a subject for inhalation. ASPECT 93.

In one aspect, the invention provides a device according to any one or more of aspects 1-93, wherein some, most, generally all, or all of the components of the device are washable (e.g., the mouthpiece component and at least a part of the variable inlet component are washable). ASPECT 94.

In one aspect, the invention provides a device according to any one or more of aspects 1-94, wherein some, most, generally all, or all of the components of the device (e.g., the mouthpiece component and at least part of the variable inlet component) are capable of being sterilized (e.g., by autoclave sterilization). ASPECT 95.

In one aspect, the invention provides a device according to any one or more of aspects 1-95, wherein one or more component(s) of the device are recyclable, reusable, or biodegradable. ASPECT 96.

In one aspect, the invention provides a device according to any one or more of aspects 1-97, wherein the device comprises an access port and wherein the access port is automatically in a closed position unless a variable inlet component is attached and engaged therewith. ASPECT 97.

In one aspect, the invention provides a device according to any one or more of aspects 1-97, wherein the device comprises an access port and wherein the access port is mostly, generally, or always open. ASPECT 98.

In one aspect, the invention provides a device according to any one or more of aspects 1-98, wherein the device comprises an access port and wherein the access port is flush with the device. ASPECT 99.

In one aspect, the invention provides a device according to any one or more of aspects 1-99, wherein the device comprises an access port and wherein the access port extends perpendicularly, substantially perpendicularly, or about perpendicularly from the device. ASPECT 100.

In one aspect, the invention provides a device according to any one or more of aspects 1-99, wherein the device comprises an access port and wherein the access port extends at an angle from the device of at least about 10 degrees (e.g., 15-75 or 25-65 degrees or 115-165 or 125-160 degrees). ASPECT 101.

In one exemplary aspect, the invention provides a kit (a collection of components(s)/device(s)) comprising two or more components of a device according to any one or more of aspects 1-101. ASPECT 102.

In one exemplary aspect, the invention provides a kit comprising (1) one or more gas container(s) and (2) one or more mouthpiece component(s) adapted to engage, e.g., releasably engage, at least one of the one or more gas container(s) and that each comprise (a) a contoured flexible mouthguard that comprises (I) a gas outlet and (II) at least right rear and left rear teeth engagement features and (b) an engagement component that releasably sealingly engages the gas container. ASPECT 103.

The kit of aspect 103, wherein the gas container is capable of assuming at least one stable vertically oriented position, and comprises (1) an inert and impermeable container material that forms a gas compartment within the gas container, the gas compartment having a capacity such that the device can deliver the equivalent of at least about 50, 100, 150, 175, 200, 220, or 250 (e.g., 50-500, 50-400, 50-300, 100-400, 100-350, 100-300, 100-250, 150-350, or 100-300) one-second, continuous release pulses of gas when full, and (2) a selectable gas release component that releases the compressed and pressurized inhalable gaseous substance, when present, from the gas container when engaged by the user, wherein the amount of the gaseous substance released from the gas container is proportional to the amount of time that the user engages the selectable gas release component. ASPECT 104.

In one aspect, the invention provides the kit of either or both of aspect 103 and aspect 104, wherein each of the at least one mouthpiece component(s) further comprise(s) at least one access port designed to receive one or more variable inlet components. ASPECT 105.

In one aspect, the invention provides the kit of aspect 105, wherein the kit further comprises one or more variable inlet component(s). ASPECT 106.

In another aspect, the invention provides methods of delivering a gaseous substance to the mouth of a mammalian user comprising (1) placing the mouthpiece component of a device according to any one or more of aspects 1-101 into the mouth of a user such that at least some of the user's teeth engage the right rear and left rear teeth engagement features when the user's mouth is closed and (2) having the user or a person assisting the user engages the gas release component to deliver the gas to the user. ASPECT 107.

In another aspect, the invention provides a method of delivering a gas to a mammalian user comprising performing a step for the user engaging a device according to any one or more of aspects 1-101 and a step for engaging the gas release means to deliver the gas to the user. ASPECT 108.

In one aspect, the invention provides a method of aspect 108, wherein the method comprises a step for at least partially closing the nostrils of the user while administering the gas to the user. ASPECT 109.

In one aspect, the invention provides a method of aspect 107, wherein the method comprises the person assisting the user in placing the mouthpiece component of the device into the mouth of the user and engaging the gas release component of the device/gas container to release the gas and deliver it to the user. ASPECT 110.

In one aspect, the invention provides a method of any one or more of aspects 107-110 wherein the gas comprises at least about 95-99% oxygen. ASPECT 21.

In one aspect, the invention provides a method of any one or more of aspects 107-111, wherein the method comprises the person assisting the user directly or indirectly, at least partially closing the nostrils of the user by action of one hand and operating the device by action of the other hand. ASPECT 112.

In one aspect, the invention provides a method of any one or more of aspects 107-112 wherein the user is a person who has asthma. ASPECT 113.

In one aspect, the invention provides a method of any one or more of aspects 107-113, wherein the user is a person who suffers from an infection, such as a viral infection, such as a COVID-19 infection. ASPECT 114.

In one aspect, the invention provides a method of any one or more of aspects 107-114, wherein the user is a person who has epilepsy. ASPECT 115.

In one aspect, the invention provides a method of any one or more of aspects 107-115, wherein the user is a person that is known or suspected to contain saliva-transmissible chemicals, such as fentanyl. ASPECT 116.

In one aspect, the invention provides a method of any one of aspects 107-116, wherein the user is unconscious or at risk of unconsciousness during at least a part of the method. ASPECT 117.

In one aspect, the invention provides a method of any one or more of aspects 107-117 wherein the user entirely performs the method. ASPECT 118.

In one aspect, the invention provides a method of aspect 118, wherein the user performs the method in the presence of air particulates or a harmful gas. ASPECT 119.

In one aspect, the invention provides a method of aspect 119, wherein the user performs the method in the presence of a fire or smoke-filled area. ASPECT 120.

In one aspect, the invention provides a method of any one or more of aspects 107-120, wherein the gaseous substance further includes one or more other gasses that detectably or significantly improve one or more conditions in a significant number of intended users. ASPECT 121.

In one aspect, the invention provides a method of aspect 121, wherein the gaseous substance comprises an effective amount of nitric oxide, such as at least about 0.001% nitric oxide. ASPECT 122.

In one aspect, the invention provides a method of any one or more of aspects 107-122, wherein the method comprises the user or the person assisting the user attaching the mouthpiece component to the gas container before performing any other step of the method. ASPECT 33.

In one aspect, the invention provides a method of any one or more of aspects 107-123, wherein the method comprises releasing the mouthpiece component from the gas container after performing the other steps of the method one or more times. ASPECT 123.

In one aspect, the invention provides a method of any one or more of aspects 107-124 wherein the method comprises (1) cleaning and reusing the mouthpiece component, (2) refilling and reusing the gas container, or (3) performing both (1) and (2), in each case after using the device one or more times. ASPECT 125.

In one aspect, the invention provides a method of any one or more of aspects 107-125, the method further comprising (1) providing a variable inlet component; (2) ensuring attachment of the variable inlet component to the device; and (3) delivering additional gas flow to the user through the variable inlet component. ASPECT 126.

In one aspect, the invention provides a method according to aspect 126, the method comprising a person assisting the user exhaling a breath into the variable inlet component such that the variable inlet component delivers at least a portion of the exhaled breath from the variable inlet to the user. ASPECT 127.

In an aspect, the invention provides a method of aspect 127, wherein the method comprises the person assisting the user compressing a flexible part of the variable inlet component, collapsing part of the flexible part of the variable inlet component, or both. ASPECT 128.

In one aspect, the invention provides the method of any one of aspects 107-128, wherein the target subject (user) is unconscious or at risk of unconsciousness during the execution of at least a part of the method. ASPECT 128.

In one aspect, the invention provides the method of any one of aspects 107-129, wherein the method comprises attaching and using a variable inlet component, removing a variable inlet component, or both. ASPECT 130.

In one aspect, the invention provides a device or method of any one or more of the preceding aspects, in which one or more elements of the aspects are combined with or modified to comprise one or more features of any of the original claims of this disclosure.

In one aspect, the invention provides a device or method of any one or more of the preceding aspects, in which one or more elements of the aspects are combined with or modified to comprise one or more features of any of the original Figures of this disclosure, optionally as characterized in the description thereof provided herein.

BRIEF DESCRIPTION OF THE DRAWINGS/FIGURES

The drawings/figures provided here, and the associated following brief description of figures are intended to exemplify certain aspects and principles of the invention without limiting its scope.

DETAILED DESCRIPTION OF THE INVENTION

Figure 1:
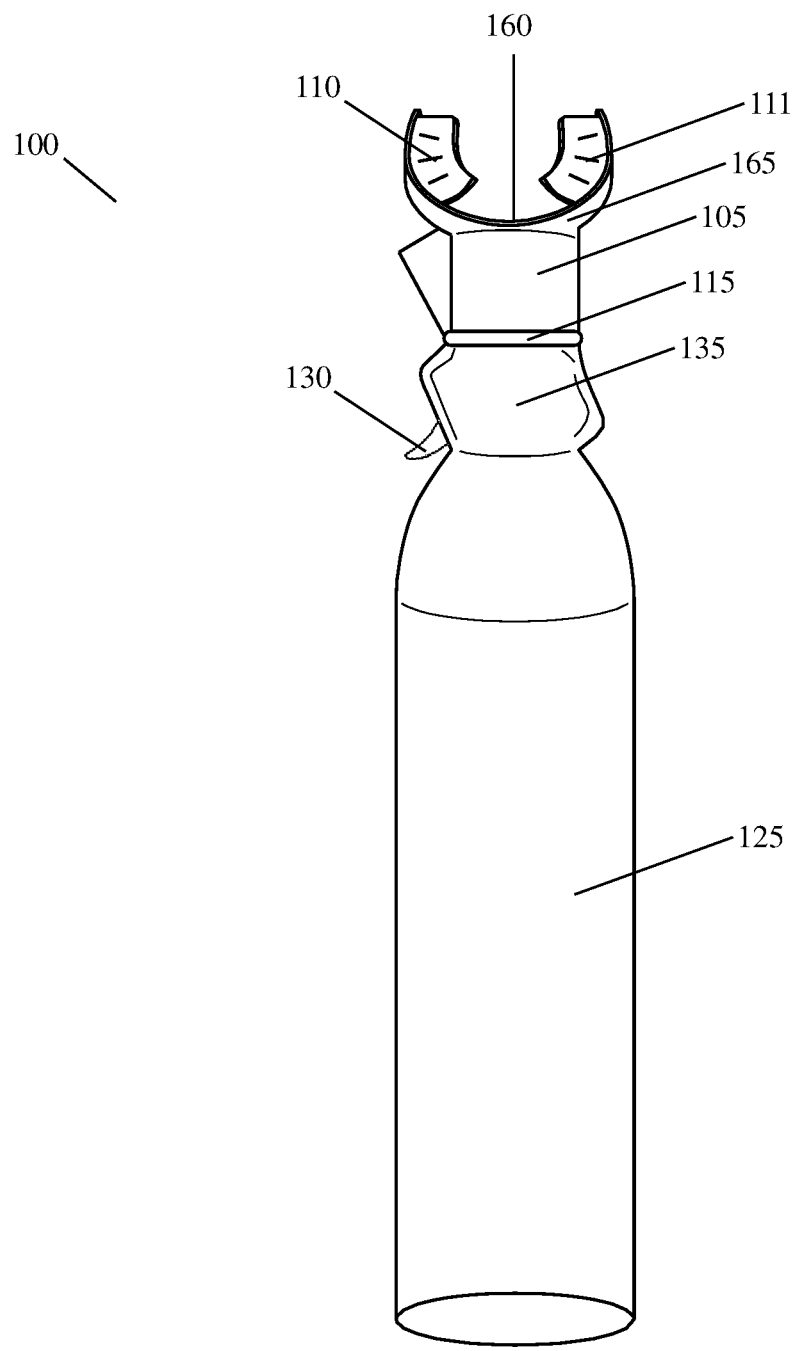
FIG. 1 is an isometric view of an exemplary assembled device/assembly of the invention comprising both a gas container component, e.g., an oxygen canister component, and a mouthpiece component, which sealingly and stably engages the gas container component.

To better illustrate the invention, descriptions of exemplary objects (e.g., devices, compositions, systems, etc.), methods, and individual elements thereof may be described in this Detailed Description of the Invention ("Detailed Description").

Despite the inclusion of passages focused on specific elements/steps in this Detailed Description, uncontradicted, any aspect, facet, embodiment, or other description of a particular step(s) or element(s) can be applied to any other aspect.

Uncontradicted, any passage contained in this Detailed Description is to be interpreted as exemplary in nature and not intended to limit the scope of any possible aspect(s) of the invention provided by the disclosure.

Highly Portable Gas Delivery Devices and Components Thereof

The invention provides a component or device for engaging a gas container, such as a highly portable gas container, which, in aspects, contains a mouthpiece component, which in aspects comprises a contoured mouthguard that comprises one or more channels that permit airflow from an engaged gas container to be delivered into the mouth of a user.

A mouthguard component comprises one or more tooth engagement features/components, which may be alternatively referred to as "occlusion features" or components and which may be exemplified as "bite trays," which are structures known in the art in association with mouthguards.

The terms "component" or "device" or even "system" are sometimes alternatively used in this respect, refer to the fact that such mouthpiece components can be considered a component of a larger device/system comprising a gas storage device or other gas source and alternatively can be provided as a standalone device that is adapted to engage one or more types of gas storage devices, e.g., one or more highly portable gas containers.

The devices of the invention are typically associated with highly portable gas container(s). A "highly portable gas container" usually means a gas storage and delivery device that weighs less than about 3 pounds, e.g., less than about 2.5, less than about 2, less than about 1.5, less than about 1.25, less than about 1, less than about 0.75, less than about 0.66, less than about 0.5, or less than about 0.33 pounds. Typically, such devices are highly pressurized, compressed gas devices, and composed of materials suitable for maintaining gas under such pressures (e.g., about 50-500, 100-350, 50-350, 100-400, 50-400, 125-375, 125-250, 50-150, 50-200, 75-300, or 75-225 psi). In some respects, the devices operate without any propellants, aerosols, or the like. Many highly portable gas container devices are known, particularly for the storage and delivery of highly enriched oxygen gases. An example of such devices is the oxygen delivery devices currently marketed under the Boost Oxygen™ trademark.

An "engagement component" can be any component that permits a component of a device to engage another. In the case of a mouthpiece component, an engagement component is any one or more device(s)/component(s) or element(s)/feature(s) that permit the mouthpiece component to engage the gas container (sometimes called the primary gas container) in a suitable manner. A "suitable engagement" in this respect means an engagement that is effective for the intended purpose of the interacting components/devices, as described herein or as will otherwise be evident to readers (and in any event, uncontradicted, means an engagement that maintains the engaged components/devices in association for the desired period under expected/normal conditions). In the context of a mouthpiece component and a gas container/primary gas container a suitable engagement is one that maintains the connection/association of these devices/components in a manner that provides for a reliable flow of gas from the gas container into the mouthpiece component (directly or indirectly) and thereafter into the mouth of a user/treated person. Uncontradicted, any engagement described herein is a suitable engagement.

In aspects, the engagement component engages one or more other components, features, structures, etc., on the counterpart component/device (e.g., the engagement component of a mouthpiece component engages a counterpart component/structure on a gas container). In such aspects, the combination of such component(s)/structure(s) can be characterized as an "engagement mechanism." Uncontradicted, any engagement component described herein implicitly can be part of an engagement mechanism comprising counterpart structure(s) on the counterpart engaged device/component.

Examples of suitable engagement components are known in the art and, uncontradicted, any suitable type can be used or any device that provides equivalent functionality (in this respect a device can be considered to include one or more "engagement means"). Examples of such devices/components/features/mechanisms include fasteners (e.g., screws, adhesives, bolts, e.g., threaded connectors, clamps, etc.), couplings (e.g., universal joints, flange couplings, sleeve couplings, etc.), and seals (e.g., O-rings, gaskets, lip seals, etc.), etc. Other examples are provided elsewhere here (in the detailed discussion of engagement components), and equivalents to the engagement components described here and there are known.

In aspects, an engagement component or engagement mechanism can be characterized as a "rapid release" or "quick release" engagement mechanism. Uncontradicted, any engagement component described herein in connection with a mouthpiece component, or a variable inlet component is, at least one in one aspect, implicitly a rapid release engagement component. A "rapid release" engagement component is one that most human users can release with minimal or no instruction within less than about 2 minutes, less than about 1 minute, less than about 30 seconds, less than about 20 seconds, less than about 10 seconds, less than about 7 seconds, less than about 5 seconds, less than about 3 seconds, or less than about 2 seconds (e.g., 1-15 seconds, 1-10 seconds, 0.25-5 seconds, 0.5-5 seconds, 0.5-10 seconds, 0.5-15 seconds, 2-12 seconds, 2-8 seconds, 3-15 seconds, 3-18 seconds, or 3-30 seconds). In aspects, a device includes visual instruction for triggering release of a rapid release engagement component, or most, generally all, or all rapid release engagement components of the device. Examples of rapid release components, and other types of engagement components, are described below.

The mouthpiece interface device/component further comprises a transition element positioned between the engagement component and the mouthguard component, and that comprises (a) an interior flow passage (that allows fluid communication of the gas from the gas container to the mouthpiece) and, in aspects and (b) has a body surrounding the interior flow passage that (I) mostly, generally, or entirely can be characterized a substantially stable/rigid body in use (by either being composed of a relatively rigid or relative rigid material that substantially retains the shape of the transition element during normal conditions of use), (II) is of a relatively limited length (here length meaning the largest dimension of the component) (e.g., less than about 12, 10, 9, 8, 7, 6, 5, or 4 inches (e.g., between 3-12, 3-9, 4-10, 4-8, 3.5-9.5, or 3.5-7 inches), or (III) is of a limited size as compared to other components of the system (e.g., is shorter in length than any associated variable inlet tube, has no dimension that is more than 1.5×, 2×, 2.5×, 3×, 3.5×, 4×, or 5× that of the greatest dimension of the primary gas container, etc.).

In aspects, a transition element can also comprise or be described as a multi-port connector. Where suitable, these terms implicitly provide support for aspects comprising the counterpart term herein (e.g., any time transition element is used herein it implicitly discloses, where suitable, a counterpart aspect in which the transition element is a multi-port connector). The term multi-port connector is used to reflect that such components typically comprise a port leading to a gas delivery component (e.g., a mouthpiece component, as described above and elsewhere) and to a gas source (e.g., a gas container). In aspects, a transition element/multi-port connector comprises a gas inlet port/opening, a gas outlet port/opening, and an open/hollow body that is impermeable to gas(es), such that the transition element forms an airflow passageway/channel or area (e.g., comprising multiple channels) between the gas container and the mouthpiece component or gas delivery component that a user engages to receive gas. The substantially rigid body of the transition element means that it maintains its shape or a substantially similar shape in use, as described further elsewhere. Thus, in aspects, the transition element is, in aspects, clearly not a hose or hose-like tube or similar element (e.g., does permit free movement with respect to other components of the device). In transition elements that comprise a substantially stable/rigid body, the mouthpiece component maintains its position with respect to the gas container when the transition element serves to connect the gas container and the mouthpiece component or other oral gas delivery element.

A mouthguard component in aspects further comprises a lip engagement component/mouth seal component, which engages the lips of a user's mouth and better seals the mouth when the device is in use. A flexible mouthguard component is typically mostly, generally entirely, substantially entirely, essentially, or entirely composed of a silicone-based material, such as a silicone rubber material, or a material having substantially similar properties in terms of user safety, hardness/softness, etc.

Such devices can be combined with one or more gas delivery/storage devices (e.g., pressurized gas canisters) to form more complex devices (assemblies) or systems or otherwise form a part/component of a larger device or system. For example, such devices can comprise a variable inlet component.

In such regard, the invention provides, for example, a device for delivering gas to a user comprising: (1) a gas container comprising (a) an inert and impermeable container material that forms a gas compartment and (b) a stable, compressed, pressurized, aerosol-free, and propellant-free supply of an inhalable gaseous substance suitable for mammalian consumption contained in the gas compartment, the gas compartment having a capacity such that the device can deliver the equivalent of at least about 25 one second continuous release pulses of gas when full, and (c) a selectable gas release component that releases the compressed and pressurized inhalable gaseous substance from the gas container when engaged by the user, and (2) a releasable mouthpiece component that is adapted to engage the gas container and that comprises (a) a contoured flexible mouthguard that comprises (I) a gas outlet and (II) at least right rear and left rear teeth engagement components, (b) an engagement component that releasably sealingly engages the gas container, and (c) a transition element that retains a substantially stable shape in use. A device comprising both the gas delivery/storage component/device and the mouthpiece component/device can be described as an "operable device." It also can sometimes be referred to as an assembly, particularly in aspects where the devices are releasable/separatable, e.g., in aspects where the gas delivery/storage device can operate as a gas delivery system independently of the mouthpiece component.

In another illustrative aspect, the invention provides, e.g., a device for delivering gas to a mammalian user (e.g., a human) comprising (1) a gas container, e.g., a gas canister device that is capable of assuming at least one stable vertically oriented position, and that comprises (a) one or more outer horizontal dimensions comprising either an outer length and outer width or, where the device is cylindrical in shape, an outer diameter, (b) an inert and impermeable container material that forms a gas compartment (e.g., a metallic material, such as aluminum or another material that is lightweight, insert, and capable of maintaining the gas under pressurized conditions, such as ≥~100 pound per square inch of pressure (psi/PSI), e.g., ≥~125 psi, or ≥~150 psi or greater, and (c) a stable, compressed, pressurized, aerosol-free, and propellant-free supply of an inhalable gaseous substance suitable for mammalian consumption contained in the gas compartment (at pressure, as noted above), the gas compartment having a capacity such that the device can deliver the equivalent of at least about 25 one second continuous release pulses of gas when full (e.g., ≥30 pulses, such as about 25-250 pulses, 30-240 pulses, 30-210 pulses, or 25-200 pulses, etc. (e.g., 50-200, 50-100, 50-150, 30-150, 30-120, 30-180, 40-200, 40-160, 75-300, or 75-150 pulses), and (d) a selectable gas release component that releases the compressed and pressurized inhalable gaseous substance from the gas container when engaged by the user (e.g., a button, dial, knob, lever, or trigger that engages a release valve or other release component(s)), wherein the amount of the gaseous substance released from the gas container is proportional to the amount of time that the user engages the selectable gas release component (i.e., the longer the release component is engaged the more air is released) and (2) a releasable mouthpiece component that is adapted to engage the gas container (e.g., by seal, threading, or other engagement method/means) and that comprises (a) a contoured flexible mouthguard that comprises (I) a gas outlet and (II) at least right rear and left rear teeth engagement features/components, (b) an engagement component that releasably sealingly engages the gas container, and (c) a transition element comprising one or more outer dimensions and an interior gas flow passage that permits the gaseous substance released from the gas container to flow from the gas container to the gas outlet. In aspects, the transition element can be characterized by (1) comprising a substantially rigid body (i.e., a body that does not change shape significantly during ordinary use), (2) comprising a structure that stays substantially in the same position with respect to the gas container when engaged, (3) has no outer dimension size (including height, length, and width) that is more than five times the size of the largest outer horizontal dimension size of the gas container (and, accordingly, the transition element is not elongated like a hose). In aspects, the overall device is exceptionally light, e.g., about 2.5 pounds or less, such as about 2 pounds or less, about 1.5 pounds or less, about 1 pound or less, or even less than 1 pound, such as about 0.75, 0.66, 0.5, 0.4, or 0.33 pounds or less.

In another exemplary aspect, the invention provides a highly portable gas delivery device as, e.g., described above, wherein the mouthpiece component further comprises at least one access port designed to receive one or more gas conveyance components. In aspects, the gas conveyance component may be a supplemental inlet tube such as an oxygen tube or breathing tube. In the same aspects, the supplemental tube provides an alternative means/pathway for delivering additional gas to the user from the primary pathway of from the [first] gas container and into the mouthpiece component, such as delivering oxygen from another gas container/source or from the mouth of a person assisting the user. In aspects, a supplemental inlet component (e.g., a supplemental inlet tube) is also capable of or specifically designed to provide gas that is used in combination with a highly portable gas container such as Boost Oxygen™ devices. In aspects, the device can be operated with or without the gas conveyance component. In aspects, access port(s) can be selectively open(ed), wherein when open, an access port can receive one or more materials therethrough, and when closed, is sufficiently sealed so as to keep/retain at least about 95% of the inhalable gaseous substance released from the applicable gas source within the supplemental inlet component or flow path comprising the supplemental inlet component (the secondary flow path). In the same or additional aspects, the access port(s) is/are selectively open, and the materials received therethrough are an additional gaseous substance such as oxygen from an additional oxygen tank or from the mouth of a person assisting the user. In aspects, a supplemental inlet component can be characterized as a variable inlet component, which is a component that is specifically adapted to delivery gas through a secondary flow path from two or more sources (e.g., from either breaths of an assistant or from a gas sources, such as another gas container or gas generator/collector).

Devices that comprise variable inlet components, without a mouthpiece component, represent an independent aspect of this invention, as exemplified elsewhere.

Components of devices provided here also can represent inventive subject matter and, accordingly, also can be considered aspects of the invention.

In yet another aspect, the invention provides new methods of delivering gaseous substances to the mouth/lungs of a mammalian user comprising (1) placing the mouthpiece of a device having the elements/construction/components of the above-described device into the mouth of a user such that at least some of the user's teeth engage the right rear and left rear teeth engagement features of the mouthguard component when the user's mouth is closed and (2) having the user or a person assisting the user engage the gas release component to deliver the gas to the user. In some respects, the method is performed by a person assisting the user. In some respects, the user is a person who is unconscious or at risk of becoming unconscious. In some respects, a user is a person having a condition wherein transmission of saliva materials is highly undesired, such as exposure to a chemical (e.g., to a drug, such as fentanyl or a toxin/poison) or to an infectious agent (e.g., a virus, such as a coronavirus or other virus), or the person has epilepsy, asthma, COPD, is undergoing poisoning or drug overdose, is undergoing a seizure or other kind of uncontrolled movement, is undergoing a heart attack or other coronary-related condition, or other condition that makes use of the device highly desirable as compared to existing gas delivery systems. In aspects, use of devices of the invention can significantly or measurably (detectably) reduce the risk or severity of treated person-induced injuries to an assistant, such as, e.g., from biting, saliva exchange, or transmission of undesirable substances. In aspects, a treated person is a person known to have or is at risk of having COVID-19 or similar contagious illness.

In yet another aspect, the invention provides a kit for delivering gaseous substances to the mouth/lungs of a mammalian user comprising (1) at least one gas container such as the aforementioned Boost Oxygen™ device(s) and (2) at least one releasable mouthpiece component that is adapted to engage the gas container and that comprises (a) a contoured flexible mouthguard that comprises (I) a gas outlet and (II) at least right rear and left rear teeth engagement features and (b) an engagement component that releasably sealingly engages the gas container. In the same or additional aspects, at least one of the at least one mouthpiece component(s) further comprise(s) an access port designed to receive one or more gas conveyance components. In some additional respects, the kit further comprises at least one gas conveyance component, wherein the gas conveyance component may be a supplemental inlet tube such as a breathing tube or oxygen tube.

In facets, devices of the invention can be characterized by their simplicity, e.g., in what they lack as compared to systems/devices of the prior art, which can contribute both to resiliency, effectiveness, and safety. For example, in some respects, the mouthpiece component lacks any electronic components or powered components. In aspects, a device of the invention lacks any "air bag" component, such as are often used in association with breathing mask devices in the art. The mouthpiece device/component also can lack any wearable component, connector hose, face mask, or mouthpiece that surrounds the nose and the like. In aspects, devices of the invention are characterized by comprising ≤10, ≤8, ≤7, ≤6, or ≤5 separable parts (e.g., the only separable parts may be, in aspects, (1) the mouthpiece component and (2) the gas storage container, but in aspects devices may further comprise a separate (3) transition element/multi-port connector, or (4) a variable inlet component (or in cases a two-part, separable variable inlet component (4) and (5)). In aspects, one or more parts of the mouthpiece component are separable from other parts. For example, in aspects, a mouthguard component can be separated from other parts of the mouthpiece component. In aspects, the mouthpiece component is a single, integrated component that is not adapted to separable intentionally under normal conditions of use (e.g., by being molded as a single piece).

In aspects, devices of the invention are characterized by the inclusion of one or more elements/components that are specifically adapted to engage one or more pre-existing other components or devices. E.g., in one aspect the invention provides a mouthpiece component comprising an engagement component that is specifically adapted to fit one or more types of currently marketed Boost Oxygen™ canisters. In aspects, the specific engagement promotes rapid engagement/release of the applicable component. By specific adaptation to a widespread and available device, devices of the invention can readily be put into practice with relatively less risk of inoperability due to depletion of associated gas storage component(s). Specific adaptation is described elsewhere and known, but generally includes configuration in terms of size of element(s), shape of element(s), etc., so as to engage the target counterpart component or device effectively or preferentially measurably or significantly.

In aspects, some, most, generally all, or all of the components of a device are "disposable," recyclable, biodegradable, or reusable. Recyclable in this respect means being composed of a material that is generally recognized as suitable for recycling such as a recyclable metal or a recyclable plastic (e.g., a grade 1-6, grade 1-5, grade 1-4, or grade 1-3 plastic material (see, e.g., millerrecycling.com/plastics-recycling-numbers/). Measures and classifications for biodegradability also are known in the art (see. e.g., Rocha W F C et al. Environ Res. 2016 October; 27(10): 799-811. doi: 10.1080/1062936X.2016.1238010. Epub 2016 Oct. 6. PMID: 27710037; PMCID: PMC5382130). A disposable component is a component that has an intended usability of less than 5 applications, less than 3 applications, or only a single use (i.e., is a single use intended component). A reusable component is a component that can be used repeatedly, in contrast to a disposable component. E.g., a gas container might be subject to reuse with recharging/refilling with relevant gas. Flexible components, e.g., a transition element, a flexible part of the variable inlet tube, or other components that are or are not flexible might be disposable. Alternatively, such components (any thereof) might be considered recyclable.

To further illuminate the invention, focus is given in the following sections to the specific components that can be incorporated in devices or kits of the invention.

Mouthpiece Component/Mouthpiece Interface Device

Devices of the invention typically include a gas delivery means or component, which provides for the effective delivery of gas into the mouth of a user.

In aspects, the gas delivery means/component comprises a mouthpiece component. A mouthpiece component can be any component comprising a mouthpiece, which is a structure that is adapted to engage the mouth of a user effectively/suitably during use. In aspects, a mouthpiece component comprises a mouthguard component (a structure that engages at least some of the teeth of a user/treated person in use). A mouthpiece component can comprise other components. A mouthpiece component typically comprises ≥1 engagement component(s) that engage other parts of the device, typically including an oxygen container or other type of gas container. In aspects, a mouthpiece component comprises a transition/transitional element/component that separates the mouthpiece from an engagement component that engages the gas container.

Readers should note that many characteristics and features of mouthpiece components that in aspects are included in devices of the invention are described elsewhere in this disclosure.

As noted, in aspects devices of the invention include a mouthpiece component. For example, in aspects, the invention provides new devices that comprise (1) a mouthpiece component which, in turn, comprises (a) a mouthguard (e.g., a contoured mouthguard) that comprises (I) a gas outlet that permits gas to flow through the mouthguard and into the mouth of a user and (II) one or more bite tray(s) or other tooth engagement structure(s), (2) an engagement component that allows the mouthpiece component to engage one or more highly portable gas storage/delivery component(s)/device(s) such that the mouthpiece component can be in operable association with such a gas storage/delivery device or component, and (3) a size-constricted, substantially positionally stable (or "substantially rigid"), or both size-constricted and substantially rigid transition component (aka transition element) that comprises a gas passageway that allows for flow of gas from the gas storage/delivery device/component. A "contoured" mouthguard is a mouthguard that is shaped, in part, to match the contouring of the mouth of a typical user, e.g., by having a horseshoe or oval shape, similar to typical mouthguards known in the art. A "flexible" mouthguard means that s mouthguard that is mostly, generally, or entirely made up of a flexible, resilient, or elastic material (the terms resilient, flexible, and elastic, in such contexts, are meant to provide implicit support for one another herein). A material that can bend or stretch reversibly. In aspects, the material(s) that make up such a component have an elasticity modulus of, e.g., 0.001-20 MPa, e.g., ~0.005-15 MPa, e.g., 0.003-12 MPa, 0.004-8 MPa, 0.01-10 MPa, 0.05-10 MPa, 0.1-10 MPa, 0.2-10 MPa, or 0.005-5 MPa. In aspects, material(s) that are described as flexible, resilient, elastic, etc., have an elasticity modulus of, e.g., ~0.05-10 ksi, e.g., about 0.07-9.5 ksi. In aspects, the material(s) have a flexibility, elasticity, etc., that corresponds to any of the materials described herein in connection with flexible components or that are used in mouthguards or other components of the art that are described/known in the art to be flexible, resilient, elastic, etc.

Additionally, in aspects, the mouthpiece component (sometimes simply called "the mouthpiece") further comprises at least one access port designed to receive/engage one or more variable inlet components. Access ports are described elsewhere. In aspects, most, generally all, or all access ports of a mouthpiece component are located in a transition/transitional element (these terms are used interchangeably herein).

In aspects, the invention provides more complex devices that comprise such a device as a component of the more complex device and, i.a., a gas delivery/storage device/component that is in operable association with the mouthpiece component. Such devices can be described as "operable devices." An "operable device" typically means a device including one of the gas delivery devices of the invention (e.g., a mouthpiece component having any of the various features provided herein, a variable inlet tube having any of the various features provided herein, or both) in combination with one or more engaged gas containers/gas sources that are suitably engaged to provide gaseous/fluid communication from the gas container to the gas delivery device(s).

In aspects, in such more complex, operable devices, comprising a mouthpiece component and a gas source, the mouthpiece component can be releasable, e.g., rapidly releasable. Such devices can be described by terms such as a "releasable assembly" or "rapid release device." Exemplary characteristics of rapid release devices are provided elsewhere.

In aspects, such components/devise can comprise other elements, such as, e.g., a lip seal/lip engagement component, is characterized by the materials of construction (e.g., the fact that at least the mouthguard is mostly, generally, substantially only, essentially only, or only composed of silicone rubber(s)), or by other elements/characteristics described in another portion of this disclosure. For the sake of illuminating the invention, the various components of such devices, assemblies, systems, etc., and inventive methods practiced with such devices are described in the following sections of this disclosure.

In aspects, the mouthpiece component is adapted to maintain its position in the mouth of most users under most ordinary conditions. In aspects a mouthpiece component can provide such stable positioning even in a near unconscious treated person, an unconscious treated person, or a treated person undergoing seizures, convulsions, etc., such as a treated person with epilepsy undergoing an epileptic seizure. In aspects, most, generally all, or all of the exterior-facing part of a mouthguard is placed under the lips of a user/ treated person. In aspects, the device comprises a lip seal/lip guard component that facilitates and promotes the retention of the mouthpiece component, sealing of the mouth (with respect to delivered gas), or both. These and any such statements herein regarding performance of devices, components, etc., can be demonstrated by any suitable type of testing, including consumer trial or clinical study (e.g., one or two well controlled and adequate clinical studies according to regulatory authority standards of testing, such as US FDA standards).

In aspects, the mouthpiece component can be characterized by the lack of one or more elements that may be associated with other types of "mouthpieces" described in the art. For example, mouthpiece components may lack any structure that covers the nose when in use. Accordingly, the mouthpiece components/interface devices of the invention in aspects lack (or are not bound to or engage) any mask structure (a mask meaning a structure that covers substantially more of the face than just the lips, such as all of the nostrils, most of the mouth, or both, etc.). In other aspects, mouthpiece components/devices may lack any tubular structure that protrudes into the mouth of a user in use or that a user has to wrap its lips around in order to operate (e.g., the type of oval mouthpieces commonly used in nebulizers and similar devices), which may, i.a., present a choking hazard for some users in some use facets.

Mouthguard Component (Teeth Separation Means)

As noted, the mouthguard components/devices provided by the invention comprise a mouthguard component that comprises one or more structures that engage and separate at least some of the teeth of a user when in use. In an aspect, any mouthguard that suitably performs such a function can be used. In aspects, the mouthguard component comprises at least left and right rear bite trays or other types of teeth engagement structure(s)/feature(s). A number of such mouthguards are known in the art. In aspects, the mouthguard is a contoured mouthguard. In aspects, the mouthguard has a U-shaped/C-shaped or horseshoe-shaped structure. In aspects, the mouthguard includes raised and recessed sections designed to engage one or more teeth of a user specifically. In aspects, the mouthguard can include vertical bar structures or similar types of structures on the teeth-covering surface(s) of the mouthguard or other features that may disperse impact forces to a user (e.g., similar to the vertical bar features of currently marketed Gelfort™ mouthguards). In aspects, the mouthguard has a height or thickness (e.g., both) in some, most, generally all, substantially all, or all of its sections of about 1-6 mm, such as about 1.25-5.75 mm or 1.2-5.2 mm, e.g., about 1.35-4.35 mm, about 1.6-4.6 mm, or about 1.4-4.4 mm, e.g., about 1.5-3.75 mm, about 1.65-3.65 mm, or about 1.6-3.6 mm, e.g., about 1.5-3.75 mm or about 1.6-3.9 mm (thickness in this respect corresponding to the amount of material separating two or more parts of the body such as upper and lower teeth, teeth and lips, etc.). In aspects, the mouthguard component has a width of about 25-100 mm, e.g., about 35-85 mm, e.g., about 40-75 mm, ~45-70 mm, ~45-65 mm, or ~45-60 mm (measured across the distal rear ends of the tooth engagement features/bite trays). In aspects, the mouthguard has a length of about 20-100 mm, such as about 35-85, 35-75, or 35-65 mm, e.g., about 40-60 mm (measured from the frontmost portion of the mouthguard to the rearmost portion of the mouthguard). Examples of mouthguard devices that may have components, features, or characteristics that can be applied/adapted with respect to the features/characteristics of a mouthguard component of the invention are described in numerous US patents including, e.g., U.S. Pat. Nos. 3,505,995A, 3,407,808A, 3,223,085A, 3,692,025A, 4,063,552A, 4,044,762A, 4,114,614A, 4,848,365A, 4,765,324A, 4,955,393A, 5,031,638A, 5,234,005A, 5,152,301A, 5,293,880A, 5,406,963A, 5,447,168A, 5,447,168A, 5,566,684A, 5,692,523A, 5,931,164A, 6,092,524A, 6,082,363A, 6,505,628B2, 6,505,628B2, 6,986,354B1, 7,299,804B2, 7,571,727B2, 7,549,423B1, 7,832,404B2, 8,205,618B2, 8,539,955B2, 8,590,538B2, 8,607,798B2, 8,689,797B2, 9,242,164B2, 9,770,644B2, U.S. Ser. Nos. 10/076,700B2, 10/343,047B2, 10/610,763, 10/806,553, 10/905,534B1, 11/109,808B2, 11/534,371B2, 11/554,309B2, and 11/701,568B2, Additional relevant disclosures may be found in published US patent applications including, e.g., US20040154626A1, US20040154625A1, US20070151567A1, US20120017922A1, US20110088703A1, US20120017922A1, US20120318280A1, US20120279506A1, US20130247923A1, US20140261465A1, US20140083435A1, US20140290669A1, US20150004555A1, US20150031994A1, US20170120135A1, US20180133581A1, US20180228643A1, US20180250577A1, US20180325722A1, US20200282639A1, US20210283489A1, US20220168070A1, US20230173373A1, US20230225899A1, US20230241486A1, and US20230241486A1. Still further additional disclosures may be found in foreign/international patent documents, such as AU2017100564, CN113058254, EP3897449, WO2016187331, WO2018161112, and WO2023055293A. Elements of mouthguard design are also provided in, e.g., Roberts, HW. Sports mouthguard overview: Materials, fabrication techniques, existing standards, and future research needs. Dental Traumatology. 2023; 39: 101-108. doi.org/10.1111/edt.12809. Elements of such components are also described in the references provided in the Background of this disclosure. Readers will understand that not all aspects of such disclosures are applicable to all aspects of the present invention. For example, in aspects, the mouthguard of the present invention lacks any air/gas release passages other than may form part of the gas outlet, thereby focusing the delivery of gas to the gas outlet and preventing undesirable release of gas. Similarly, the mouthguard/mouthpiece of the invention, in some respects, is not associated with any strap/tether attachment or similar structure, which are commonly associated with athletic mouthguards described in many of these disclosures. Thus, while aeration vents/orifices (e.g., breathing holes) may be described as present in such prior art systems/devices, such features/elements would not be incorporated into such aspects of the invention. Readers will understand what types of features of such prior art disclosures can be incorporated into mouthguard components of the present invention consistent with the aspects thereof provided herein. Uncontradicted, any element, characteristic, etc., of such disclosures that do not conflict with the elements, requirements, etc., of any aspect can be combined with such an aspect to form more particular aspects of this invention (e.g., having an upper and lower tooth engagement part, incorporating different materials or layers in construction, including sensors, the inclusion of markings, incorporating other features or specific design elements, methods of production, etc.).

The mouthguard component can be shaped in any suitable manner. In aspects, the mouthguard specifically fits an individual user in one or more ways. This can be done by self-fitting (e.g., so-called boil and bite fitting methods or other self-fitting methods) or by custom-fit design and machine methods. In other aspects, the mouthguard is not intended to fit any specific user. In aspects, the mouthguard is adapted to fit a typical/average person in a population of individuals (e.g., adults, children, the elderly, etc.). In aspects, a mouthguard or an entire mouthpiece is custom fit or is shaped to fit a particular user. The mouthpiece component can lack any structure that covers the nose. The mouthpiece component typically lacks any oval mouthpiece structure of the type used in nebulizers. In aspects, a mouthguard comprises other openings to promote breathing through the mouthguard. In aspects, a mouthguard component lacks any openings when engaged other than the outlet component, so as to promote retention/delivery of delivered gas to the user.

The mouthguard component comprises an inlet that receives gas from the gas container, from a variable inlet component/supplemental inlet component, or both, depending on the characteristics/components of the device. An inlet of a mouthguard component can be any suitable type of gas inlet, including one or more holes/orifices or channels through which gas may flow. The mouthguard component further comprises an outlet that releases received gas into the mouth of a user. A mouthguard component can comprise passageway(s) or flow paths between the inlet and outlet. In aspects, the inlet and outlet can be very close to each other. In aspects, the outlet and inlet are effectively one structure or feature. For example, in aspects, in which the mouthguard component comprises an opening between rear teeth engagement elements, the inlet and outlet may either be the same opening/open area or may be otherwise in very close proximity to one another (e.g., within less than about 0.75 cm, e.g., 0.2-0.8, 0.25-0.75, 0.1-0.9, 0.15-0.75, 0.3-0.9, 0.3-0.6, 0.3-0.8 cm, etc.). E.g., an inlet in aspects may be placed on one side or end of a mouthguard component and an outlet be placed on another side or end. In aspects, a mouthguard component comprises only right rear and left rear teeth engagement components, comprising an opening therebetween (e.g., as depicted in the Figures) (a space between the teeth engagement elements). In aspects, a mouthguard component generally engages all, substantially all, or all the teeth of a typical user. In aspects, a mouthguard component engages less than half of the teeth of a user. In aspects, the teeth engagement elements (bite tray(s)) of a mouthguard component have a sufficient thickness such that when a typical user engages the engagement elements/bite tray a sufficiently sized gap is formed between at least some of the front teeth (i.e., between the top and bottom teeth) of the user to permit gas to flow readily or promote/facilitate between such teeth and into the mouth of the user (wherever a user is described herein this disclosure implicitly supports a corresponding aspect in which the user is a semi-conscious or unconscious "treated person" rather than a conscious user). In aspects, the gap formed in a typical user when the bite tray/engagement elements are engaged is about 0.5 mm-1.5 cm (15 mm), 1 mm-1.25 cm, about 1.5 mm-10 mm (1 cm), about 2 mm-1.2 cm, about 2 mm-1 cm, about 2.5 mm-1 cm, about 3 mm-1.2 cm, about 4 mm-1.2 cm, about 5 mm-1 cm, about 5 mm-1.25 cm, etc.

Gas Outlet and Gas Flow Component(s) (Gas Outlet Means)

The mouthguard component or other part of the mouthpiece component or mouth associated gas delivery device comprises a gas outlet and, optionally, additional gas flow component(s) leading to the gas outlet (e.g., channel(s) and associated channel-forming element(s), such as a body). The gas outlet can have any suitable configuration. In some respects/facets, the gas flow outlet is a single orifice/port. In aspects, the gas flow outlet is composed of more than one orifice/port/hole. E.g., in aspects, the gas flow outlet may be composed of 2, 3, 4, 5, 10, 15, 20, 25, 30, 35, 40, 50, 75, 100, or more holes/opening(s) or port(s). In an aspect, the gas outlet is a single opening/orifice and has a maximum horizontal dimension (length/width or diameter, as applicable) of about 8 mm, e.g., about 7 mm, 6.5 mm, 6 mm, 5.5 mm, or 5 mm (e.g., 1-8 mm, 1.5-7.5 mm, 2.5-7.5 mm, 3-7 mm, 3.5-7.5 mm, 3.5-7 mm, 2-6 mm, 1.5-6.5 mm, 2-6.5 mm, 2.5-6.5 mm, or ~3-6 mm). In aspects, the gas outlet is cylindrical and has a diameter according to such measures. In aspects, the gas outlet has a different shape but provides a similar amount of overall opening for gas flow to the user. In aspects, the mouthguard comprises additional structures for facilitating airflow from the gas storage/delivery component/device to the user (airflow/gas flow components). In other aspects, the gas outlet can be considered to be a tube, passageway, channel, or set/series thereof, which passes through/transverse (forms an opening in) a part of the mouthguard component and thus is exposed to the mouth of a user when the user engages the mouthguard. In aspects, the portion of the mouthguard forming the gas outlet may have a hardness that is DOS greater than the hardness of some, most, generally all, or all of the tooth engagement feature(s) (e.g., bite tray(s)). In aspects, the length of the gas outlet is less than about 20 mm, such as less than about 15 or 12 mm, or less than about 10, less than about 8, or less than about 7 mm (e.g., 5-25 mm, 5-20 mm, 7.5-22.5 mm, 8-24 mm, 9-22.5 mm, 10-25 mm, 10-22.5 mm, or 12-25 mm). In aspects, the length of the gas outlet is less than about 7.5 mm, e.g., about 0.5-7.5 mm, about 1-7.5 mm, about 1.5-6.5 mm, about 1.5-5.5 mm, about 2-5 mm, about 1-4 mm, about 1-3 mm, or about 0.5-3.5 mm. In aspects, the gas outlet only delivers a single flow of a single type of gas. In aspects, the gas outlet can deliver multiple flows of gas, e.g., where there are multiple gas delivery/storage devices associated with a mouthpiece. Uncontradicted, the aspects of the gas outlet(s) described herein connection with the mouthpiece component can also be applied to the outlet of a variable input component.

Engagement Component(s) (Engagement Means)

A device/mouthpiece component typically comprises at least one engagement component (in aspects, devices comprise two or more engagement components, some, most, or all of which may form part of engagement mechanisms).

In the context of a mouthpiece component, an engagement component (which can be called, e.g., a mouthpiece engagement component) can be any suitable component for permitting the mouthpiece component (overall) to sealingly and stably engage one or more highly portable gas delivery/storage device(s)/component(s). Accordingly, the features of the engagement component will vary based on the counterpart gas delivery/storage component(s)/device(s) that the mouthpiece device/component of the invention is to engage. A wide variety of engagement mechanisms are known in the art. Examples include the use of threaded elements, clips, fasteners (screws, bolts, nuts, washers, rivets, etc.), hinges, brackets, clamps, couplers, connectors (e.g., plugs, jacks, pins, sockets, etc.), and the like. In general, any suitable type of engagement component can be used.

In aspects, one, some, most, generally all or all of the engagement components of a device will have the capacity to securely hold 1.5×, 2×, 2.5×, 3×, 3.5×, 4×, 5×, 7×, or 10× the weight of intended counterpart gas delivery/storage component(s)/device(s), such that a user can pick up the operational device by the mouthpiece component without the components separating. As described elsewhere, in aspects, the engagement between a mouthpiece component and a gas container is such that the device can be used by most or at least generally all users of a type of user in a hands-free manner, without having to support the device in use (e.g., where the overall device is very lightweight as described elsewhere).

In aspects, the engagement component is a "rapid release" component. A rapid-release engagement component is a component that allows a user to selectively cause a rapid separation of the mouthpiece component and the gas delivery/storage device/component of an assembly/operational device. Typical/exemplary characteristics of rapid release engagement components/engagements are described above. Again, a number of such engagement components are known in the art.

Examples of rapid-release engagement components include, e.g., quick-release couplings, quick-release latches, magnetic mounts/connectors or mechanisms, push-pull connectors, snap-in connectors, vacuum mounts, hook and loop fasteners, bayonet connectors/mounts, clips such as lanyard clips or carabiners, spring-associated engagement mechanisms, or twist-lock mechanisms. Such devices are known. In aspects, a device comprises at least two rapid-release engagement components/mechanisms (e.g., one or more associated with the mouthpiece component, one or more associated with a variable inlet component, or both).

In facets, the engagement component is relatively lightweight (e.g., having a weight of about 1-20 ounces, such as about 1 pound or less, e.g., about 0.5 pounds or less, about 0.33 pounds or less, about 0.25 pounds or less, about 0.2 lbs. or less, or about 0.15 pounds or less (e.g., about 0.05-0.4 pounds, about 0.075-0.35 lbs., about 0.1-0.3 pounds, or about 0.1-0.2 lbs.). The engagement component is typically composed of a durable material that is impervious and inert (non-reactive) with respect to the gas. In some facets, the material is a plastic or metallic material. In aspects, the material comprises, mostly is, generally is, substantially is, or entirely is aluminum. In aspects, this part, most parts, or all parts of the mouthpiece component/device are dishwasher safe, having the ability to be cleaned through dishwasher use, repeatedly, without DOS loss of functionality (e.g., over 20, over 50, over 100, or over 1000 uses on average).

As noted, in some facets, the engagement component is specifically adapted to engage one or more particular types of gas delivery/storage devices. In aspects, the gas delivery/storage device engaged by the mouthpiece component/device is, when released from the mouthpiece component/device, capable of independent operability as a gas delivery device. In such aspects, the engagement of the mouthpiece component is of a nature that does not DOS impair the independent operability of the gas delivery/storage device. E.g., in one aspect, the engagement component is specifically designed to engage one or more of the currently marketed Boost Oxygen™ canisters, in aspects in a rapid-release manner. In such aspects, a user may, e.g., carry the mouthpiece component separately from the gas delivery/storage device, using the mouthpiece component only under such situations or with such users as may be particularly advantageous, e.g., in the various exemplary use described elsewhere.

Engagements here can be described as releasable (or re-attachable), sealing (sealingly), and the like. Such terms will be understood by readers. In general, such terms are understood to be effective and suitable with respect to such functions, at least in aspects. For example, a releasable engagement is understood as being releasable based on the action of a typical adult human user of a device under normal conditions within a suitable period of time (e.g., less than 5, less than 3, or less than 2 minutes).

In aspects, the engagement component is a part of a transition element/multi-port component, examples of which are described elsewhere herein. In aspects, the engagement component is separable from the transition element.

Backflow Prevention Elements (Means for Preventing Backflow)

The engagement component can comprise or be spatially associated with a mouthpiece component inlet. The mouthpiece component inlet is a component that permits the flow of gas from the gas storage/delivery device into the mouthpiece component. In aspect, the inlet is a simple opening/orifice, e.g., within an engagement component, or is a structure that is associated with the engagement component (e.g., that is attached thereto). In some respects, the mouthpiece component inlet can be selectively openable or closeable. In aspects, the mouthpiece component may be selectively adjustable. In aspects, the mouthpiece component can comprise or be associated with one or more components for preventing the backflow of material from the mouthpiece component to the gas delivery/storage component/device. A variety of such components are known in the art. In aspects, the component comprises unidirectional valve(s). Examples include checkpoint valves, non-return valves, globe valves, lift check valves, diaphragm valves, pinch valves, solenoid valves, motorized valves, or pneumatic valves. In aspects, valve(s) used in such a context are mostly, generally only, or only unpowered valve(s), such as checkpoint valve(s). In aspect, the valve(s) of such a device can be characterized as or comprise "one-way valve(s)" as are known in the art. In aspects, one, some, most, generally all, or all valve(s) in a device of the invention are selectively removeable, either for, e.g., modifying functionality or configuration, for replacement, or both, in aspects without eliminating all functionality of the device (e.g., a valve associated with a variable inlet component might be selectively removed from an assembly but the mouthpiece component still work through a first airflow passageway from the primary/first gas container). In aspects, a one-way removable valve is placed near one or both ends of the variable inlet component, transition element, or both. In aspects, a one-way valve associated with a variable inlet component can be disengaged (e.g., unscrewed) when a treated person is resuscitated, or the user or assistant no longer wishes to use the variable inlet component (e.g., without removing the entire variable inlet component from the device). In aspects, a one-way valve is also or alternatively positioned in the transition element of a device. In aspects, an access port can be selectively closed until engaged. For example, a device can comprise an access port that is closed until either a user opens it, a component engages it (e.g., a supplemental inlet component or a variable inlet component engages it), or both.

Transition Element (Gas Transition Means)

Typically, the mouthpiece component comprises a transition element that comprises a gas flow passageway or passageway(s) that permit the flow of gas released from the gas delivery/storage device/component to the mouthguard and thereby to the user without DOS loss of the gas. A transition element, if/when present, can aid in the positioning of the mouthguard and gas outlet by providing some distance from the gas storage/delivery device.

In aspects, the transition element directly engages or comprise a gas container engagement component. In aspects, the transition element is made up of a resilient or highly flexible material. In aspects, the transition element is, at least in part, a highly flexible and can readily change shape when, e.g., about 1-30, 2-30, 2-24, 2-20, 1-20, 1-15, 2-16, 2-12, 3-15, 3-12, or 2.5-10 newtons is applied to the transition element. In aspects, a transition element is resilient (composed of a resilient material) and will return within 300, 250, 200, 150, 120, 90, 60, 30, or 15 seconds to a position/shape that is generally the same as, substantially the same as, or the same as its original shape (e.g., a shape-memory polymer (e.g., a polyurethane, a polycaprolactone, a poly(lactic) acid (PLA), an EVA, etc.), a nitinol material, or an elastomer (e.g., a silicone rubber, an ethylene-propylene diene monomer (EPDM) rubber, a fluorosilicone rubber, a neoprene rubber, or a butyl rubber) or equivalent resilient material). In this respect, a transition element can be considered to provide a flexible attachment point in view of the fact that the transition element can be moved with relative ease (e.g., using forces such as those described above) into a position in which the user or assistant can more readily (detectably or significantly) connect the engagement component to a counterpart feature/component.

In aspects, a transition element can be a flexible structure, such as a hose. However, in other aspects, the transition element can be described as "resilient" or "substantially rigid" in shape/construction and/or as being size-restricted (not having a significant length as compared to its other dimensions or not having any dimension that is significantly larger than, e.g., any of the horizontal dimensions of the gas delivery/storage device/component). Such terminology, when used, is intended to refer to the fact that the transition element will mostly, generally, substantially always, or always have the same structure under normal operating conditions of the device. In such aspects, the transition element does not have the features of a hose but, rather, is a shorter/smaller, DOS more rigid/stable, or both shorter/smaller and more stable/more resilient structure than a hose-like structure. In such aspects, the construction of the transition element can assist in, i.a., rapid user engagement of the mouthpiece component, as the mouthguard element of the device/system avoids random movements ("flopping around") as might occur with a hose structure. The transition element can be composed of any suitable gas impervious/inert and suitably resilient or rigid material where such characteristic is also required. For example, such materials can include metallic materials such as steel (e.g., stainless steel). However, the transition element in aspects is lightweight (e.g., about 0.05-0.5 lbs., such as ~0.05-0.35, 0.05-0.25, 0.05-0.1, 0.1-0.5, 0.1-0.25, or 0.1-0.33 pounds). In such aspects, the transition element may be mostly, generally, substantially, or entirely composed of aluminum, a polymer (e.g., polyethylene (PE), polypropylene (PP), polyvinyl chloride (PVC), polyurethane (PU), or fluoropolymer material, or a combination thereof), or a mixture thereof. In aspects, the transition element has a maximum horizontal dimension (length, width, or diameter) of 6 inches, e.g., about 5 inches or less, about 4 inches or less, or about 3.5 inches or less, e.g., about 0.5-3.5 inches, about 1-4 inches, about 1-3.5 inches, about 1.25-3.75 inches, about 1.25-3.25 inches, or about 1.5-3 inches. In facets, no outer dimension size of the transition element is more than five times the size (e.g., ≤~4×, ≤3.5×, ≤~3×, ~2.5×, ≤~2×, ≤~1.5×, ≤1.25×, or ≤~1.1× of the largest outer horizontal dimension size of the gas container (delivery/storage device/component)). For example, if the gas container is cylindrical and has a diameter of about 3 inches, in aspects, the transition element is less than 10.5 inches, such as less than about 6 inches, or even less than about 4.5 inches, in all dimensions (length, width, and height). As noted, in facets, the transition element substantially retains its shape in use. In embodiments, the transition element may be somewhat flexible. In aspects, the transition element may be flexible but resilient, allowing for some give and take of movement but substantially retaining the same shape at rest or in use over a number of uses/movements (e.g., ≥10, ≥50, ≥100, or ≥1000 uses/movements).

In aspects, the transition element receives, or can receive, at least in part, flow of gas from both the mouthpiece engagement component engaging a first gas container and separately from a variable inlet component. The flow of gas from the first gas container, through the transition element, to the mouthpiece (e.g., to the outlet of a mouthguard), can be characterized as a primary pathway or flow path, and the flow path through the variable inlet component to the transition element, and thereafter also into the mouthpiece, can be characterized as a second flow path. In aspects, both flow of gas from the variable inlet component and the primary flow path are delivered to the same outlet. In aspects, these flow paths deliver to different outlets in the mouthpiece (e.g., in the mouthguard).

In aspects, most of the transition element, at least in one dimension, is within the primary/first flow path (from the gas container—aka, the first gas container and to/into the mouthpiece component). In aspects, a part of the second/secondary flow path (from a second source—such as a person breathing, another gas container, or other gas source and through a supplemental inlet component or variable inlet component) is also through at least part of the transition element. In aspects, the portion of the transition element that is in the secondary flow path is less than the portion that is within the primary flow path, in at least one dimension.

Lip Engagement/Seal Component (Lip Engagement/Seal Means)

In aspects, a mouthpiece/mouthguard further comprises or is associated with a lip engagement component or lip seal component. Examples of lip seal elements/structures are known in the art and described in some of the above-incorporated patent references directed to mouthguards and mouthpieces. In aspects, the lip seal/lip engagement component is configured to DOS better seal the mouth of a user when the device is in use, e.g., by DOS reducing the amount of gas loss from the user's mouth. In aspects, the lip seal/lip engagement component also DOS reduces the amount of material that is lost from the user's mouth during use, e.g., undesirable saliva loss. In aspects, the lip seal is composed of the same material as most or all of the rest of the mouthguard. In aspects, the lip seal is composed of a material that has a greater hardness than most, generally all, or all of the mouthguard. In aspect, the lip seal does not prevent lip closure in typical users, even when the user is unconscious. In aspects, the lip seal provides soft tissue coverage of up to 2 mm from the vestibular reflection.

Composition of the Mouthpiece Component

The mouthpiece component can be composed of any suitable type and number of material(s). In aspects, the mouthguard component has a shore A hardness of between about 25 and 100, e.g., about 40-100. In aspects, the liner of a mouthpiece component has a shore A hardness of about 35-70, such as about 40-60 (all shore A hardness measurements are at 37° C. unless otherwise indicated). In facets, the other parts of the mouthguard have a shore A hardness of at least 50, such as about 55-100, e.g., 55-96. In aspects, the materials of the mouthguard have a water sorption of about 0.5 wt. % or less. In aspects, the tear strength of most, generally all, or all of the material that makes up the mouthguard or the entire mouthpiece component has a tear strength of at least about 200 N−cm−1 @ 37° C. (e.g., as specified in ANSI/ADA Standard No. 99).

In aspects, some, most, generally all, or all of one or more parts of the mouthpiece component are formed of silicone rubber compound(s) or other suitable silicone compound(s) or other suitable rubber compound(s), alone or together with other materials where suitably combined. In aspects, some, most, generally all, or all of the mouthguard is composed of one or more types of silicone rubber and in aspects some, most, generally all, or all of the mouthguard or entire mouthpiece component is composed of a type of vulcanized silicone rubber, e.g., room temperature vulcanized silicone rubber(s) (RTV). In facets, some, most, generally all, substantially all, or all of a feature of a mouthguard (sometimes called a part of a mouthguard, even though such parts are typically portions of a single component), the entire mouthguard, and possibly other portions of the mouthpiece component are composed of a type of liquid silicone rubber, solid/high temperature vulcanized (HTV) silicone rubber, or RTV silicone rubber. Silicone rubber mouthguards are described in, e.g., Auroy et al., The Journal of Prosthetic Dentistry, Volume 75, Issue 4, April 1996, Pages 463-471. Specific exemplary materials can comprise, e.g., silicone rubbers such as DUROPRENE, or the silicone rubbers sold under the trade name DRAGON SKIN, such as DRAGON SKIN 10, by Smooth-On, or the resin material sold under the trade name BLUESIL, such as BLUESIL 3040, by Bluestar Silicones; polyurethanes; polycaprolactones, synthetic rubbers; or nylon.

Other flexible, resilient materials are described herein in connection with other components of the device, and, uncontradicted, any suitable type of flexible, resilient, or otherwise suitable materials described in connection with components can make up some, most, generally all, or all of the composition of another component of a device.

In aspects, some, most, generally all, or all of one or more parts of the mouthpiece component are formed of ethylene vinyl acetate (EVA). Disclosures relating to this and other known materials for the composition of mouthguards are provided in, e.g., Maeda et al., Dental Traumatology, 25: 556-564. doi.org/10.1111/j.1600-9657.2009.00822.x; Guevara et al., Dental Clinics of North America, Volume 35, Issue 4, 1991, Pages 667-682, ISSN 0011-8532, doi.org/10.1016/S0011-8532(22)00833-3; and Going et al., The Journal of the American Dental Association, Volume 89, Issue 1, 1974, Pages 132-138, ISSN 0002-8177.

In aspects, some, most, generally all, or all of one or more parts of the mouthpiece component are formed of polyolefin (e.g., polyethylene (PE), polypropylene (PP), or polybutylene (PB)). In aspects, some, most, generally all, or all of the mouthguard (or mouthpiece component/mouthpiece) is composed of thermoplastic polyurethane(s) (TPU(s)).

In aspects, some, most, generally all, or all of one or more parts of the mouthpiece component are formed of a processed acrylic resin.

In aspects, some, most, generally all, or all of one or more parts of the mouthpiece component are formed of polyvinyl acetate-polyethylene.

In aspects, some, most, generally all, or all of one or more parts of the mouthpiece component are formed of polyvinylchloride (PVC), latex rubber, acrylic resin, polyurethane, or a combination thereof, or a combination with any one or more of the other materials mentioned above in this section. In aspects, the mouthguard, or the entire mouthpiece, is generally, substantially, or entirely free of PVC.

In aspects, the mouthpiece or at least the mouthguard is at least substantially free, if not entirely free (within the limits of detection), of bisphenol A ("BPA"), methyl methacrylate, or both. In aspects, the mouthpiece or at least the mouthguard is generally, substantially, or entirely free of phthalates. In aspects, the only phthalate in the mouthguard or mouthpiece is a dialkyl o-phthalate or a phthalate having a similar or lesser oral toxicity profile. In aspects, a mouthpiece, mouthguard, or device is generally, substantially, or entirely free of any or all thereof or also generally, substantially, or entirely free of BPA, latex, PVC, or a combination.

In aspects, some, most, generally all, or all of the material comprises inclusions.

In facets, the material can comprise polyamides, poly (ethylene terephthalate glycol) (PETG), or polyurethanes (PUs) in relatively small amounts, in combination with one or more of the previously mentioned materials (e.g., EVA or silicone rubber). As noted, combinations of such materials can be used. E.g., a combination of TPU and PETG, such as in different layers within a mouthguard or different parts, can be used.

In aspects, some, most, generally all, or all of the mouthguard component and possibly other parts of the mouthpiece are composed of ternary thiolene systems modified with urethane (UMTEN) or acrylate (AMTEN). In aspects, materials of the mouthguard or other elements of the mouthpiece can comprise, mostly comprise, generally consist of or consist of polyetheretherketone (PEEK). These and other materials are characterized in, e.g., Sousa et al., July 2020 Polymers 12(1490):1490, DOI:10.3390/polym12071490. The Sousa article also provides a description of general mouthguard structural features that can be applied in regard to the mouthguard element of the invention. Any or all part(s) of the mouthguard described therein or herein, or the mouthpiece overall, can be composed somewhat, mostly, generally, substantially, or entirely of any one or more of the types of materials described in this section. Thus, for example, the mouthguard, part(s) of the mouthguard, other part(s) of the mouthpiece, or a combination thereof, can be composed of, e.g., at least about 5%, 10%, 15%, 25%, or 35% of such a material or combination thereof. In aspects, part(s) of the mouthguard, other part(s) of the mouthpiece, or a combination thereof, can be mostly, generally, substantially, or only composed of one or more of such materials. Readers will understand that reference to a type/class of a composition (e.g., EVA, of which several types are known) provides support for any suitable particular type(s) of such composition being used.

Access Port(s)

In aspects, the mouthpiece component may further comprise at least one access port designed to receive one or more component(s) of a device, e.g., one or more variable inlet component(s).

Access port(s) are any structure that permits the flow of additional material, such as a gaseous substance, to a part of the device, such as a transition element. In cases, such a gas can be further delivered to a user/treated person either solely or in combination with a second gaseous substance from another (secondary) gas container/source. A port, in this regard usually means some opening (controlled/selectable or not) into a structure (e.g., a body) comprising a gas flow passageway. A port can be of any suitable size or shape.

In aspects, the access port(s) extends, at least in part, at a substantial angle to the largest axis of the device (e.g., the vertical axis) (e.g., at least 15 degrees, e.g., ≥20, ≥30, ≥40, ≥45, or ≥60 degrees) or perpendicular to the device (and in aspects, the passageway/channel, etc., associated with flow of gas from the gas container to the mouthpiece is parallel to the orientation of the device or within +/−15 degrees).

In aspects, access port(s) can be selectively opened or closed, depending on the preference of the user or person assisting the user. In aspects, the access port(s) can be partially open or partially closed. In such aspects, when the access port(s) is/are selectively open, the access port(s) can receive materials, such as a gaseous substance, therethrough. In aspects when the access port(s) is/are selectively closed, the seal is sufficient to keep at least about 95% of the inhalable gaseous substance in the variable inlet component (e.g., ≥98%, ≥99%, or ≥99.9%) from exiting the device via the access port(s). In aspects, the access port is automatically open when an engagement with a variable inlet component. In aspects, the access port(s) is always open or always closed.

In aspects, the access port(s) can comprise or be associated with one or more components for preventing the backflow of material from the access port and/or mouthpiece component to the gas delivery/storage component/device or variable inlet component(s). A variety of such components are known in the art. In aspects, the component comprises unidirectional valve(s). Examples include checkpoint valves, non-return valves, globe valves, lift check valves, diaphragm valves, pinch valves, solenoid valves, motorized valves, or pneumatic valves. In aspects, valve(s) used in such a context are mostly, generally only, or only unpowered valve(s), such as checkpoint valve(s). Uncontradicted, any of these types of components can be applied to other components that seek to prevent backflow (e.g., as described elsewhere with respect to gas flow from the gas container to the mouthpiece), and any elements described in respect of such other aspects can be applied as backflow prevention means in this context.

In aspects, the invention provides access port components that are specifically adapted to engage one or more other components of a device/system of the invention (e.g., a gas container, a mouthpiece component, etc.). Such devices (access port components) represent independent aspects of the invention, apart from any other components. In aspects, such an access port device is a multi-access-port component comprising a port adapted for a mouthpiece component, a port adapted for a gas container, and a port adapted for engaging a variable inlet component as described herein.

Supplemental Inlet Component(s)

In embodiments, devices of the invention comprise supplemental inlet component(s) in addition to the mouthpiece component.

A supplement inlet component can comprise or consist of any suitable structure(s) that permit additional input of gas to a user through a flow path that is different from the first/primary flow path (the primary flow path or first flow path comprising a flow path from the gas container (aka the first gas container) through the engagement component (i.e., through the "first engagement component" (where several engagement components are in a device)), typically through most if not generally all of the transition element, and through the mouthguard into the mouth of a user). A supplemental inlet component, when present, can, in aspects, at least in part, comprise or form at least part of a second gas pathway to the mouthpiece component. Alternatively, a supplemental inlet component might deliver gas to the user through some other terminus of the second pathway, such as to the nose of a user or to the mouth but through some other structure than the mouthpiece component.

In aspects, a supplemental inlet component can take the form of a tube and, accordingly, sometimes the term "supplemental inlet tube" is used in this disclosure. Readers will recognize that, uncontradicted, the term supplemental inlet component provides implicit disclosure of aspects where the supplemental inlet component comprises, generally consists of, or entirely consists of a tube shape, and, likewise, that disclosure of aspects using the term supplemental inlet tube provides support for corresponding aspects in which the supplemental inlet tube term is replaced with supplemental inlet component and can comprise non-tubular structures.

In aspects, a supplemental inlet component may, for example, comprise or consist of a short breathing tube of the conventional type described in the prior art (e.g., as described in the Background), or a hose/tube for gas delivery (e.g., as described in other references cited in the Background), or other gas delivery mean, that can engage an access port of the mouthpiece component, e.g., an access port positioned in the transition element.

In aspects, such a supplemental inlet component is associated with a flow path that does not flow through as much of the transition element as the primary flow path (e.g., in aspects, the primary flow path goes across most, generally all, or substantially all of the transition element in at least one direction and the secondary flow path associated with the supplemental inlet component flows across less than 50% of, e.g., less than 33% of, the transition element in one direction or in any direction).

In aspects, a supplemental inlet component is a variable inlet component (i.e., in aspects, a variable inlet component can be used as a supplemental inlet component).

Variable Inlet Component(s)

In aspects, a mouthpiece component or other device/system of the invention further comprises at least one access port designed to receive one or more variable inlet component(s), sometimes alternatively referred to as a gas conveyance component(s). In aspects, device(s) lack any variable inlet component or access port for such a component. In aspects, devices are provided wherein the connection to a gas supply is mostly, generally, entirely, or only through a variable inlet component.

In a typical aspect, the variable inlet component provides an alternative way to deliver gas(es) to a user, apart from the element(s) of a device associated with the gas container (which can be called the primary, first, or main gas container) (e.g., the engagement component and transition element of a device), which is why such elements are called "supplemental" inlet components. However, as noted, a variable inlet component can, in aspects, be used independently of any other airflow to the mouthpiece component or other user gas delivery component. As such, readers should not be misled by the term "supplemental" into improperly limiting the scope/nature of such element(s).

In aspects, the variable inlet component is composed of or mostly, generally, or substantially/essentially is a tube. In aspects, such a tube/component can be configured to engage the at least one or more access port(s) of a device/mouthpiece component (e.g., an access port located in a transition element, such as near the top of the transition element or in a part of the transition element near/proximal to where the transition element interfaces/engages with the mouthguard or mouthguard-associated components of the mouthpiece component).

A "tube" in this respect or, uncontradicted, any other respect herein, can have any suitable shape (e.g., a round shape, an oval shape, or a square shape).

In aspects, a variable inlet component comprises one or more sections (e.g., one section) comprising a contoured, arched, or bowed shape (having a resting partial elliptical, rounded, or bowed shape with respect to the orientation of, e.g., a vertically oriented (standing) resting gas container (e.g., as exemplified in the figures submitted herewith) (e.g., comprising, in part, a section marked by a variable sloping angle that ranges between 30-65 degrees, e.g., about 35-55, about 40-50, or about 45 degrees). For example, a flexible portion of a variable inlet component can have such a resting position, which can help limit the overall "footprint" of the device (area of a surface contacting or covered by any of its resting components when the device is placed in its ordinary resting position (e.g., vertically standing)) to less than about 1.5, less than about 1.25, or less than about 1 foot, e.g., less than about 11, less than about 10, or even less than about 9 inches, further promoting the portability of the device. In aspects, no element of the device has a maximum dimension greater than 24 inches, greater than 22 inches, greater than 20 inches, greater than 18 inches, greater than 15 inches, or greater than 12 inches.

In aspects, a device comprises only a variable inlet component as a gas delivery device to the user, e.g., to the mouthpiece component (apart from any gas delivery element associated with the gas storage container(s) that are independent of aspects of the invention, e.g., any gas delivery device already built into a marketed Boost Oxygen™ can).

In aspects, a device comprises only a mouthpiece component as a gas delivery device. In aspects, a device comprises both a variable inlet component and a mouthpiece component. A device that comprises both a mouthpiece component and a supplemental inlet component can be described, when assembled, as a complete, operable, or assembled "dual function" device or as a "dual gas pathway" device or by similar terminology. A device that comprises both a mouthpiece component and a variable inlet component can be described as a "three way" or "tri-functional" or "three source" device (reflecting that the device is configured for two or more sources of gas to flow through the secondary pathway comprising the variable inlet component and a distinct source of gas (the gas container/first gas container) flows through the first/primary pathway).

Parts of this disclosure may describe aspects characterized by the inclusion of a mouthpiece component and a supplemental inlet component or by a more specific terms such as, e.g., a supplemental inlet tube (in recognition of aspects in which the supplemental inlet component has a tubular shape) (e.g., as described in the preceding section). Readers will understand that, uncontradicted, any aspect described as relating to a supplemental inlet component provides implicit disclosure of a corresponding aspect in which the supplemental inlet component is a variable inlet component (and vice versa).

The flow of gas from a secondary source (e.g., a secondary or second container) through a supplemental inlet component or variable inlet component can be described as a "secondary flow path" or "second pathway." The term "second" here is in reference to the type of pathway, that being different from the type of pathway from the first container (sometimes just called the gas container) through a transition element (if present) and into the mouthpiece component. Thus, where a device only comprises a variable inlet component as a gas delivery component (without a mouthpiece component), the flow of gas through the variable inlet component can still be described as a "second pathway" or the like.

In aspects, the variable inlet component/tube is selectively removable/re-attachable to other elements of a device/system, such as a mouthpiece/gas delivery component, a gas container/delivery source, or a device described in other aspects. A variable inlet component/tube can be attached to other component(s) of a device (e.g., an access port, such as an access port of a transition element) by any suitable means, such as, e.g., the removal inlet end of the removable supplemental inlet tube comprises a fitting that engages. In aspects, a fitting or other engagement/attachment means is used to engage a component that acts as an oral engagement mechanism/element (e.g., an oral engagement tube that is composed of a plastic or rubber material) for a user to use to blow air into during certain situations, e.g., where delivery of more gas to a user is required. In aspects, engagement is performed by threading. In aspects, a fitting, threading, etc., is specifically adapted to permit the variable inlet component to engage with one or more component(s)/device(s).

In aspects, the supplemental inlet tube/component comprises an engagement end, an airflow inlet, and an airflow outlet. The engagement end of a variable inlet component (or other type of supplemental inlet component) typically refers to the end of the variable inlet component that selectively engages the rest of the device/system, such as the mouthpiece component or the transition element/multi-port component (e.g., by connecting to an access port of a multi-component device/transition element). Uncontradicted, the airflow outlet of the variable inlet component is positioned at or near the engagement end. In aspects, an access port that engages a variable inlet component or other supplemental inlet component is selectively openable/closeable (e.g., being associated with mechanism(s) for providing such functionality). In aspects, the supplemental engagement component comprises a variable inlet component inlet end. In aspects, the supplemental engagement component is composed of two or more portions, e.g., a portion that is positioned at the inlet end and a portion positioned at the engagement end.

In aspects, the variable inlet component/tube is flexible such that the tube or other structure that makes up most, generally all, or all the variable inlet component, at least in part, is expandable or collapsible. In aspects, the tube/component or relevant portion(s) of the tube/component is both expandable and collapsible.

Terms such as "collapsible" are used to refer to the ability to collapse the tube along its longest dimension (readers will understand this dimension may be described as its length, although it may be presented/shown in a substantially vertical orientation and thus alternatively could be described as its height). In aspects, in methods of the invention, the component/tube can be collapsed to reduce the distance (length of the tube/component) detectably or significantly between a person breathing into the tube and the mouthpiece component (e.g., reducing such length by ≥5%, ≥10%, ≥15%, ≥20%, ≥20%, ≥33%, or more). In such aspects, the length of the tube, when fully expanded, is at least 1.25×, 1.5×, or at least two times longer than the length of the tube when fully collapsed (e.g., is at least 2.5×, at least 3×, or at least 3.5× the length).

In facets, the body of the variable inlet component is (a) expandable so as to comprise the ability to expand in length, (b) collapsible so as to comprise the ability to decrease in length, or (c) reversibly expandable and collapsible such that the body of the variable inlet component can both expand and collapse making the length of the body reversibly longer and shorter, respectively.

In aspects, the body of the variable inlet component is reversibly expandible and collapsible, wherein the length of the body when in a fully expanded configuration is at least about 50% longer (e.g., at least about 1× longer, or at least about 2× longer, or even at least about 5× longer) than the length of the body when the body is in a fully collapsed configuration.

In aspects, the component/tube also is compressible. This aspect of "compressibility" means that the tube/component can, in part(s)/area(s), be compressed to have a smaller thickness/width/length or diameter, etc. (both collapsibility and compressibility can refer to a form of compression, but the terms are used to distinguish the ways that a component may be compressed). In aspects, the tube/component or relevant portion(s) (flexible portion(s)) thereof are/is only partially compressible (e.g., no more than 75%, no more than 65%, or no more than 50%, e.g., no more than 33%). In aspects, the tube/component can be compressed such that the maximum width or length of the airflow passageway at the point of compression is reduced by, e.g., ≥25%, ≥33%, ≥50%, ≥65%, ≥75%, ≥85%, ≥90%, or ≥95%. In method aspects, a user can compress part(s) of the tube/component to reduce the diameter/width/length of an area and thereby increase or concentrate airflow through the compressed area(s).

In alternative aspects, a variable inlet component does not comprise a flexible portion but does comprise a portion that is different in composition, structure, or both, from the other portion. E.g., a device can comprise a variable inlet component comprising a first portion that is contoured, but which is not compressible, not collapsible, or neither compressible nor collapsible. In aspects, the second/contoured portion (or flexible portion) can comprise protruded sections, such as shown in the figures herein. In aspects, such protruded sections are somewhat, mostly, or generally hollow open, such that the inner diameter/thickness-width of the device is greater at such protrude sections than in non-protrude sections.

In aspects, a compressible, collapsible, or compressible and collapsible tube forms one part of the overall structure (e.g., is positioned at or near the engagement end), and a second part is composed of a different material, has a different type of solidity (e.g., is detectably or significantly less compressible or collapsible), or both (e.g., is a more solid structure positioned at the inlet end, which can be, e.g., adapted to be engaged by the mouth of a person assisting the user (is orally engageable), can be engaged by one or more other device(s) (e.g., can sealingly engage a secondary gas container/source, e.g., a container that provides an amount of a secondary gas, such as a nitric oxide-containing gas, a helium containing gas (e.g., for aiding a treated person with asthma, COPD, or respiratory syncytial virus (RSV)), agents that assist with drug neutralization (e.g., in the case of treating a person suspected or known as suffering from a drug overdose or other drug-related condition), a gas containing one or more anesthetic agents or pain-relieving agents, a gas comprising one or more active pharmaceutical ingredients), etc.

In aspects, at least a portion of the variable inlet component is replaceable/removable/interchangeable. In one aspect, the invention provides the variable inlet component wherein at least a portion of the variable inlet component is disposable (i.e., designed, labeled, or otherwise configured/intended for single use).

In aspects, most, generally all, or all the variable inlet component is comprised of a single material. In other respects, the variable inlet component is mostly, generally, or entirely comprised of at least two detectably or significantly different materials. In aspects, such material(s) is/are selected from polyvinyl chloride (PVC), polyurethane, silicone, vinyl, nasal cannula tubing, rubber, plastic, metal, or any another material suitable for a tube designed for providing a substance to a subject for inhalation. In aspects, the material is suitable for cleaning (e.g., dishwashing). In aspects, the material is suitable for sterilization and reuse, such as in facets, autoclaving, and reuse. In aspects, some, most, generally all, or all of the materials of the variable inlet component or other component(s) of the device(s)/system(s) are made up of materials that are considered biodegradable.

In aspects, the variable inlet component (e.g., supplemental breathing/inlet tube) is configured to deliver materials to the at least one access port. In aspects, the tube or a part of the tube/element is mostly, generally, substantially, or entirely made of a flexible material such as a plastic or rubber material, which is impervious and inert to gas(es) to be delivered within the tube/component. Examples of such materials are known or disclosed elsewhere. In aspects, the supplemental inlet tube/component is impervious and inert with respect to oxygen.

In aspects, the variable inlet component has an uncompressed or maximum diameter of between about 2.0 mm and 25.0 mm, e.g., ~2.5-25, 3-24, 4-24, 5-25, 5-20, 4-20, 2-12, 3-18, 4-16, or ~5-15 mm.

The "length" of the variable inlet component can, in parts of this disclosure, refer to the component's largest dimension (which, in the figures, may correspond more to the "height" of the element). In aspects, the variable inlet component has a length that is longer than any transition element of the associated device. E.g., in aspects, the variable inlet component has a length that is at least about 1.5×, 1.75×, or at least two times the maximum dimension (or length/height) of the transition element (e.g., about 1.25-5× the length/maximum dimension of the transition element, or 2-6, 2-4, or ~2-~5× the length, such as ~1.5-4.5, 1.5-3.75, or ~1.75-3.25 the length/maximum dimension of the transition element).

In aspects, the inlet end of the tube is configured to releasably sealingly engage an external material source such as another gas storage container. In aspects, the second gas storage container may be, e.g., a pressurized gas container, a powered gas delivery device, or either/both of these. In aspects, the inlet end of the tube can engage with the same type of gas container as is engaged by the engagement component of or that engages with a transition element of a device.

In aspects, the inlet end of the tube can be orally engaged by a person assisting the user. In such aspects, the person assisting the user can, e.g., place their mouth around the inlet end of the tube and breathe air into the tube in order to provide additional oxygen to the user. Further, in such aspects, the person assisting the user orally engages the inlet end of the tube by placing their lips around the inlet end such that the person's mouth completely encloses the inlet end of the tube.

Gas Container Component/Gas Storage Means

Assemblies, systems, and operable devices of the invention comprise gas container component(s) (gas storage/delivery component(s) or gas storage means) or other suitable source of gas(es) that are in gaseous/fluid communication with other device components (e.g., a mouthpiece component). The terms fluid/gaseous communication are used interchangeably herein, as referring to a flow of materials that is mostly, generally only, substantially only, essentially only, or only in a gaseous state, under typical conditions (e.g., typical environmental conditions, such as 33-123 degrees F.).

Typically, a gas container comprises (1) a gas container capacity (which also may be called a gas compartment or gas container compartment) (which is formed by one or more structures usually formed of impervious and (at least internally) inert materials) and (II) a gas release component. Inert materials do not exhibit DOS reactivity with the gas(ses) intended to be stored in the container.

Gas-inert materials are known in the art. Examples of inert materials include plastics (e.g., polyethylene and polypropylene materials, which are inert to many gases), glass, and metals (e.g., aluminum, stainless steel, or titanium). Impervious materials do not DOS permit the release of contained gases. Such materials also are known and include, e.g., metals such as stainless steel or aluminum, glass, polytetrafluoroethylene and polymers with similar gas impervious properties, rubbers (e.g., butyl rubber), ceramics (e.g., alumina and zirconia), or graphene. In aspects, some, most, generally all, or all of the composition of the gas container is aluminum or a material that has similar or other suitable characteristics. In aspects, gas containers can comprise, e.g., carbon fiber materials.

The gas compartment can have any suitable volume. In some respects, the volume is sufficient for several repeated uses but limited to provide for both the typical small weight and size of the gas container (rendering it highly portable). In facets, the gas compartment has a capacity such that the device can deliver the equivalent of at least about 20 one-second continuous release pulses of gas when full. In aspects, the capacity is such that the device can deliver the equivalent of at least about 25, e.g., ≥~30, ≥~35, or ≥~50 one-second continuous release pulses of gas when full (e.g., ~20-300, 35-300, 30-300, 30-330, 25-350, 50-350, 50-500, 30-600, 25-500, 50-250, or 40-400 one second continuous release pulses of gas when full). In aspects, a gas container component can further comprise gas passageway(s) that allow for the flow of gas to the mouthpiece component.

The gas substance delivered in a part of a system, such as through an access port, into a mouthpiece component, through a variable inlet component/tube can be any suitable gas substance, including any of the gaseous substances described elsewhere herein (e.g., an at least about 90% or about 95% oxygen gas, a gas comprising nitric oxide, etc.). The conditions of gas storage also can be any of those described herein (e.g., a gas stored under pressure, and, in aspects, delivered without propellants or aerosols).

Composition of the Gas Container Component

The gas container component can be composed of any suitable type and number of material(s). In aspects, the gas container component is made from a high-strength material(s) that can withstand the pressure of the compresses, pressurized, or liquified gas stored inside. In aspects, some, most, generally all, or all of one or more parts of the gas container component are formed of aluminum. For example, aluminum portable gas canisters can comprise a high strength-to-weight ratio, which can be advantageous for portability. In facets, the container is composed somewhat, mostly, generally entirely, substantially entirely or entirely of aluminum. In aspects, some, most, generally all, or all of the container is composed of any of the materials described above for the formation of the gas container compartment. In aspects, some, most, generally all, or all of one or more parts of the gas container component are formed of steel. In aspects, the container is made of a material that has a weight that is within about 75-150% of the weight of an aluminum container, has at least about 50-150% of the pressure-holding capabilities of stainless steel, or has about 50-150% of the corrosion resistance capabilities of stainless steel. In aspects, the interior of the gas container component is coated with a gas-compatible material to prevent oxidation or contamination of the stored gas or to otherwise DOS maintain the integrity and purity of the gas.

In aspects, the gas container component comprises a seal or valve made from a material(s) that are compatible with gas (e.g., oxygen) and can maintain a tight seal. Examples of suitable materials for seals and valves include Viton, EPDM (Ethylene Propylene Diene Monomer), and other gas-compatible elastomers.

Gaseous Substance Characteristics

In operation, the gas container component comprises a gaseous substance (or "gas") to be delivered to a user. The gas can be any suitable gas for aiding users in dealing with intended conditions. Accordingly, the gas comprised in the gas container component will vary based on the situation or needs of the user operating the device.

In aspects, the gas is generally, substantially, or entirely composed of gas. In aspects, the gas comprises compounds or elements that are not gaseous under normal conditions of use. E.g., in aspects, the gas comprises a liquid (e.g., drops or micro-drops of a liquid, such as a liquid pharmaceutical composition, e.g., an anti-narcotic composition). In aspects, the gas also or alternatively comprises solid particles (e.g., powder particles) to be delivered to a user (e.g., powdered pharmaceutical ingredient(s)).

In aspects, the gas has a density of about 1.25-2 g/L, e.g., about 1.4-1.5 g/L.

In facets, the gas comprises an oxygen content that is at least about 80% oxygen-rich as air or is at least as oxygen-rich as air. In facets, the gas is at least mostly composed of oxygen (e.g., it is at least generally composed of oxygen). In aspects, the gas is pure or substantially pure oxygen gas. In aspects, the gas is highly oxygenated (i.e., has a higher oxygen content than air) such that it comprises 35%-100% oxygen, such as about 75-95% oxygen, or about 90-95% oxygen, such as about 95% oxygen (e.g., 35-98%, 55-98%, 55-95%, 65-95%, 90-95%, 90-98%, 85-95%, 88-98%, or 93-95% oxygen). In aspects, the oxygen concentration in the gas is 95% or less (or 98% or less or 94% or less). In some respects, the gas comprises or further comprises at least 0.001% nitric oxide. In some respects, the gas is an oxygen contained within the one or more of the currently marketed Boost Oxygen™ canisters. In aspects, the gas is an oxygen of purity such that it is better suited for a user than oxygen received from methods such as mouth-to-mouth resuscitation (is higher concentration oxygen, comprises other therapeutic elements, is more consistent over time, or some or all thereof).

Such gas characteristics can also be applied to the gas(es) associated with other gas containers associated with a system/device or other gas delivery system(s)/device(s) associated with a device, such as gas delivery systems or container(s) associated with a variable inlet component.

In aspects, use of a device of the invention is associated with measurably or significantly less adverse events in a population of users/treated persons, than is observed in mouth-to-mouth resuscitation or improves on one, some, or several aspects of breathing delivery of oxygen to a treated person (e.g., as such element(s) are described in, Joachim D. Pleil, "The physics of human breathing: flow, timing, volume, and pressure parameters for normal, on-demand, and ventilator respiration," National Library of Medicine, 2022: ncbi.nlm.nih.gov/pmc/articles/PMC8672270/). In aspects, use of devices herein, except for delivery of breath through a variable inlet component, is associated with the delivery of less than 0.5%, less than 0.3%, less than 0.2%, or less than 0.1% carbon dioxide to the treated person (e.g., less than 0.05%, less than 0.01%, less than 0.005%, or less than 0.001% carbon dioxide). In aspects, the devices/methods of the invention deliver a gas with an oxygen concentration that is higher than that of air bag systems known in the art (e.g., those described in the Background of this disclosure). In aspects, a mouthpiece component of the invention delivers, on average, in a relevant type of user/treated person, about as much gas, or a significantly similar amount of gas, if not more gas (e.g., a measurably or significantly greater amount of gas—or at least about 10, 20, 25, 30, 33% more gas) than one or more comparator mask oxygen delivery devices, such as those in one or more references cited herein. In aspects, some, most, generally all or all of the time user engagement of a mouthpiece component forms a more effective seal than a mask (which may, e.g., lose oxygen where the mask is unable to form a tight/flush seal with the face of a user). In aspects, operation of a device herein provides a measurably or significantly greater amount of overall gas, oxygen, or both, than mouth-to-mouth resuscitation, e.g., over a period of 1, at least 3, at least 5, at least 10, or at least 15, or more minutes. In aspects, practicing methods of the invention increase gas in the lungs of a treated person by a measurably greater or significantly greater amount than mouth-to-mouth breathing procedures, e.g., applying a tidal volume of greater than 550, ≥600, ≥650, ≥700, ≥750, ≥800, ≥900, ≥1000, ≥1100, ≥1200, ≥1250, or ≥1500 mL(ml) in a period in which a typical person completes a breath in such a procedure.

Gas Delivered Substances

In aspects, the gaseous substance (gas) of the gas container, of a second gas source, or both, can comprise substance(s) that measurably or significantly change the effect of delivering the gas, such as active pharmaceutical ingredient(s) (API(s)). In aspects, the gas comprises gaseous APIs, liquid APIs (e.g., micro-droplet APIs), solid API(s) (e.g., powder API(s)), or a combination thereof. Any suitable type of API(s) can be delivered in one or both gas pathway(s), in any suitable concentrations/amounts and number of pulse(s)/flow(s) or time(s)/duration(s). For example, an API can be delivered that to treat a condition that is associated with, is known to be the cause of, or is suspected to be a cause of a condition that is causing challenges for a treated person, e.g., an agent that treats asthma (e.g., inhaled corticosteroids, leukotriene modifiers, beta agonists, muscarinic agonists, ipratropium, etc.), anti-allergenic API(s), API(s) that treat heart conditions, API(s) for opening the lungs or airflow passageways, API(s) for the treatment of epilepsy, API(s) for the treatment of COPD (e.g., corticosteroids such as fluticasone, budesonide, or prednisolone, or anticholinergics, etc.).

In aspects, API(s) comprise small molecule or biomolecule sequestrants that bind and inactivate harmful substances in body. In aspects, API(s) can comprise, consist of, or consist essentially of agent(s) that reduce the absorption of undesirable compound(s) from the GI tract to the blood, brain, or both.

In aspects, API(s) in a gas comprise anti-narcotic agent(s). In aspects, the anti-narcotic agent(s) comprise antagonists of morphine, fentanyl, sufentanil, alfentanil, oxymorphone, hydromorphone, or oxycodone. In aspects, API(s) comprise agents that act against narcotic drugs or other possibly harmful drugs, e.g., agent(s) for treating a drug overdose. Compounds for treating drug overdose are described in, e.g., Akeemat et al., Journal of Controlled Release, Volume 348, 2022, Pages 970-1003, ISSN 0168-3659, doi.org/10.1016/j.jconrel.2022.06.034 and Britch, S. C., Walsh, S. L. Psychopharmacology 239, 2063-2081 (2022). doi.org/10.1007/s00213-022-06125-5. In aspects, droplets (e.g., microdroplets) of naloxone are delivered in one or both gas flow paths. Naloxone liquid drops are currently available under FDA NDA Number N208411 (NARCAN nasal spray currently sold by Emergent Devices, Inc. and approved to Emergent BioSolutions). A second FDA approval of such a product was under Application Number: N208969 (to Amphastar Pharmaceuticals, Inc., for a product under the brand name REXTOVY).

Other compositions for treatment of narcotics/opioids are known in the art (see, e.g., US20210228570). Narcotics that can be treated can include naloxone, naltrexone, nalmefene, cyclazocine, levallorphan, samidorphan, methylsamidorphan, nalodeine, alvimopan, methylnaltrexone, naloxegol, naloxol, 60-naltrexol, axelopran, bevenopran, naldemedine, cyprodime, naltrindole, norbinaltorphimine, and any suitable derivatives, analogs, salts, or other alternative forms/related compositions or combinations thereof.

Agents for treating overdose with such compounds are further described in, e.g., US20220241268). In aspects, API(s) comprises a respiratory stimulant, e.g., Doxapram, Almitrine. GAL-021, or a pharmaceutically acceptable salt or any thereof, or a combination of any thereof. In aspects, API(s) comprise nalbuphine and other kappa-opioid receptor agonist(s), opioid receptor antagonist(s), alternative forms thereof, or a combination thereof. Additional agent(s) and methods for treating such conditions that may be applicable to such aspects of the invention are described in, e.g., Powell, US Pharm. 2019; 44(3): HS2-HS8 (currently at uspharmacist.com/article/managing-opioid-overdose-in-the-hospital-setting). Naloxone-specific compositions and methods that may be applicable to aspects are described in, e.g., US20230095235, US20040180916, US20230181500, US20210338574, and US20180360822. Formulation of API(s) for droplet or other airborne delivery mechanisms are known and described in, e.g., Knap et al., Regenerative Biomaterials, Volume 10, 2023, rbac099, doi.org/10.1093/rb/rbacO99; Patil J S et al. Lung India. 2012 January; 29(1):44-9. doi: 10.4103/0970-2113.92361. PMID: 22345913; PMCID: PMC3276033; El-Sherbiny I M, et al. Glob Cardiol Sci Pract. 2015 Mar. 31; 2015:2. doi: 10.5339/gcsp.2015.2. PMID: 26779496; PMCID: PMC4386009; Chaurasiya et al, Pharmaceutics 2021, 13(1), 31; doi.org/10.3390/pharmaceutics13010031; Zhang et al. Clin Pharmacokinet. 2002; 41(9):661-80. doi: 10.2165/00003088-

200241090-00003. PMID: 12126458; Remiro et al., Pharmaceutics. 2022 Dec. 20; 15(1):12. doi: 10.3390/pharmaceutics15010012. PMID: 36678640; PMCID: PMC9864928; Paderni et al. Oral Surg Oral Med Oral Pathol Oral Radiol. 2012 September; 114(3):e25-34. doi: 10.1016/j.oooo.2012.02.016. Epub 2012 Jul. 6. PMID: 22771408; and Vara Almirall B et al. Pharmaceuticals (Basel). 2022 Oct. 13; 15(10):1259. doi: 10.3390/ph15101259. PMID: 36297371; PMCID: PMC9612176.

Gas Storage Conditions

The gas container component provides a means for safe and effective gas storage conditions. These conditions are crucial to maintain the integrity of the gas, ensure user safety, and facilitate efficient gas delivery. In some respects, the gas storage conditions are compatible with the gas outlet and other gas flow-associated elements/components of the gas container. In aspects, the as flow components should provide a smooth pathway for the gas to flow from the storage container to the user's mouth. In aspects, the gas storage conditions must be appropriate for the type of gas used, whether it is medical oxygen, therapeutic gases, or any other gas intended for inhalation. In aspects, the gas storage conditions provide a means for protecting the integrity of the stored gas. In aspects, the gas storage conditions provide proper pressure regulation such that the device remains within safe operating limits. In aspects, the gas container component is stored at safe temperatures, such as, below 125° F. (51.7° C.), to prevent the risk of overheating. In aspects, the gas container component is not exposed to direct sunlight for prolonged periods of time. In aspects, the gas is compressed/pressurized. For example, in aspects, the gas is at a pressure of at least about 100 PSI (pounds per square inch). In facets, the pressure of the gas is, on average, about 100-250 PSI, e.g., about 120-200 PSI, e.g., about 125-175 PSI, or about 130-160 PSI, such as about 135-155 PSI, or about 140 PSI.

Gas Release Component

A gas release component of a device can comprise any suitable means for selectively releasing gas from the gas container component. The gas release component can comprise a user-engageable element/feature (e.g., a trigger) and an internal release element/feature (e.g., a valve that opens to release the gas). A gas release component can be a part of a gas container or can be otherwise placed in the device, so long as it is capable of being selectively or controllably operated to release gas to a treated person or user, in aspects in a pulse and controllable manner.

The internal release element of the gas release component can be any one or more of a pressure-reducing valve (regulator), flowmeter, manual valve, electronic solenoid valve, pressure swing adsorption (PSA) system, pneumatic actuator, etc. In other aspects, release can be controlled via, i.a., a nozzle, a plunger, or a pump.

In aspects, the user-engageable element of the gas release component is a button, dial, knob, lever, or trigger that engages a release valve or other internal release component(s).

In aspects, the user-engageable portion of a gas release component is an actuator-type component, such as a trigger. The trigger or other user-engageable element (e.g., a button, switch, lever, etc.), when engaged, initiates the selectable release of pressurized or compressed gas from the gas container component. In aspects, the engagement is selectable. In aspects, the engagement is controllable. In aspects, sustained engagement with the engagement element provides for sustained, continuous release of the gas during the time of engagement (i.e., the time of engagement is proportional to the release of the gas, at least during most periods of operation) (e.g., the longer a person engages the release component the more gas is released, recognizing that rates of release can, in aspects, vary, e.g., from when a pressurized gas is first release to when a gas container is nearing emptying).

In aspects, the gas release component does not use an aerosol or propellant to release gas from the gas container component.

In aspects, the gas release component is engaged by the user or a person assisting the user in operating the device. In aspects, the gas release component is engaged for as long as needed by the user or until the gas is entirely released from the gas container component.

Gas Delivery Characteristics

The gas container component is configured to deliver gas to the mouth of a user. In aspects, when the gas release component is engaged, gas releases from the gas container component at a flow rate of about 50 mL to about 500 mL per second, such as about 100-350 mL per second. In aspects, a gas that is released from the gas container compartment flows from the container to the mouthpiece component, and from there, it is delivered to the mouth of the user. In aspects, all or substantially all of the gas released from the gas container component flows through the mouthpiece component.

Gas Container Size and Weight

The gas container component comprises a size and weight. In aspects, the gas container component has a capacity of 0.5-20 L, such as about 1-15 L with respect to pure or substantially pure oxygen gas. In aspects, the gas container component is less than about 3 pounds, e.g., about 2.5 pounds or less, such as about 2 pounds or less, about 1.5 pounds or less, about 1 pound or less, or even less than 1 pound, such as about 0.75, 0.66, 0.5, 0.4, or 0.33 pounds or less.

Other Optionally Included/Excluded Elements

In aspects, devices/systems of the invention can be characterized by elements that are lacking from the device/system or related methods of use.

In facets, devices/systems (either term providing implicit support for the other throughout this disclosure and being also applicable to any method of use described herein) are characterized by the lack of any mask that covers the nose of a user. In respects, devices/systems are characterized by a lack of any element that can be considered a mask, e.g., a mask that surrounds more of the mouth than just part of the lips of a user. In respects, devices/systems can include or can be characterized by the inclusion or lack of a device for closing the nose of a user, such as a nose clip. In facets, devices can be characterized by the inclusion of one or more positioning device(s) for element(s) of the system/device, e.g., for one or more of the gas channels/passages, the mouthpiece, etc., and in aspects devices are characterized by the lack of such elements. In some respects, devices lack any electronic components, any motorized components, or both. In some respects, the primary power for the delivery of gas(es) is from the pressurization of the gas(es). In some respects, the only power for the delivery of gas(es) in the system/device comes from the pressurization of the gas(es).

In facets, devices of the invention are characterized by the inclusion or the exclusion of a dedicated exhalation tube or other channel/passageway (in general, where the term "tube" is used herein, uncontradicted, it provides support for other corresponding non-tubular structures that are suitable). In aspects, devices lack an eye covering, an element that covers any part of the head other than the lip/mouth, or both.

In some respects, devices lack any component that generally, substantially, essentially, or completely surrounds the head of a user, such as e.g., any component characterizable as a strap or helmet. In some respects, devices lack any component designed to allow for the explicit expulsion of carbon dioxide exhaled by a user (such as, e.g., an expressly dedicated carbon dioxide release port). In respects, devices lack a component designed to facilitate the wearing of a device when the device may or may not be in use, such as one or more straps facilitating wearing the device about the user's body, e.g., around the waist or, e.g., as a backpack. In respects, devices lack a component characterizable as a demand valve. In respects, devices lack a component that generally, substantially, essentially, or completely covers one or more eyes of a user.

Kits/Collections of Components

Any of the various above-described elements of systems/devices of the invention can be provided alone or in unassembled combination as a collection of components (which latter-referenced collection of components herein may be referred to as a "kit").

For example, in one aspect the invention provides a kit (i.e., a collection of components(s)/device(s)) for delivering one or more sources of gas to a user comprising (1) a gas container that is capable of assuming at least one stable vertically oriented position and that comprises (a) one or more outer horizontal dimensions comprising an outer length, an outer width, or an outer diameter, (b) an inert and impermeable container material that forms a gas compartment within the gas container, and (c) optionally a stable, compressed, pressurized, aerosol-free, and propellant-free supply of an inhalable gaseous substance suitable for mammalian consumption contained in the gas compartment, the gas compartment having a capacity such that the device can deliver the equivalent of at least about 25 one-second, continuous release pulses of gas when full, and (d) a selectable gas release component that releases the compressed and pressurized inhalable gaseous substance, when present, from the gas container when engaged by the user, wherein the amount of the gaseous substance released from the gas container is proportional to the amount of time that the user engages the selectable gas release component; and (2) a releasable mouthpiece component that is adapted to engage the gas container and that comprises (a) a contoured flexible mouthguard that comprises (I) a gas outlet and (II) at least right rear and left rear teeth engagement features and (b) an engagement component that releasably sealingly engages the gas container. In aspects, a kit further comprises at least one or more variable inlet component(s). In aspects, a kit comprises at least two mouthpiece components, wherein the first mouthpiece component comprises or is associated with (e.g., engages, interacts with, binds, etc.) a component comprising at least two ports (e.g., a multi-port component/transition element) and the second mouthpiece component comprises (or is associated with an element that comprises) at least three ports. The phrase "right rear and left rear teeth engagement features" means that the mouthguard comprises features/elements that will, in use, engage the right rear and left rear teeth of a user (e.g., the rear 3, 4, 5, or 6 teeth of a user on both sides, on the upper teeth, lower teeth, or both the upper and lower teeth (in aspects only on the lower teeth)) and are adapted for such a purpose (e.g., comprising contouring, indentation, shaping, etc., to engage such teeth, as known in the art). Devices can comprise a complete mouthguard (engaging all the lower/upper teeth of a user/treated person) or can comprise a mouthguard in which there is separation between such features/elements. The composition of such a portion of the mouthguard typically is similar to the composition of the mouthguard, and will usually have some flexibility, be amenable to washing, and be suitable for repeat use, unless the element is designed for single/disposable use.

Use of Devices

The invention further provides methods of delivering a gaseous substance (gas(es)) to the mouth of a mammalian user comprising (1) placing a mouthpiece component of an operable device of the invention into the mouth of a user, e.g., such that at least some of the user's teeth engage a part of the mouthguard, e.g., at least engage the right rear and left rear teeth engagement features/bite tray element(s) when the user's mouth is closed and (2) having the user or a person assisting the user engage the gas release component to deliver the gas to the user. Typically, the mouthpiece component once placed in the mouth is stably positioned in the mouth of the user, even with movement, loss of consciousness, etc., in at least most cases (e.g., in at least 65%, 75%, 85%, 90%, or 95% of cases in the applicable situation, or in another significant number of times).

In aspects, the selective/controlled gas release of a device (e.g., of a gas container) can or only delivers oxygen or other gas through pulse delivery (e.g., when a gas release trigger, switch, button, or the like is engaged). In aspect, such pulse delivery allows for a user to effectively pace (time) the administration of pulses around the breathing of a user (i.e., around the treated person's breathing rhythm). For example, an assistant can, in aspects, observe a treated person and can deliver an enriched oxygen gas (a gas comprising more oxygen than air, such as any of the amounts described elsewhere herein, e.g., a gas comprising 90-95% oxygen) or other therapeutic gas to the person, in pulses, when the person is not engaged in exhaling. In aspects, such methods are performed in 2, 3, 5, 10, 20, 30, 50, or more cycles of use (e.g., 5-100, 5-50, 5-25, 3-30, 3-15, or 2-20 cycles of use).

User Characteristics

Methods of the invention can be practiced with large mammals, such as humans and companion animals. A person that uses a device can be described as a "user." In aspects, the user is a human. In aspects, the user operates the device mostly or entirely independently of any other person. However, in other aspects, an assistant assists the user with the operation of the device under some conditions. In such respects, a user can be referred to as a "targeted person" or "treated person" or by similar terminology used herein. Readers will understand that such terms provide implicit support for aspects in which the user acts independently and where the user is sometimes, mostly, or always assisted by an assistant.

In aspects, the method is performed to provide supplemental oxygen to a person in a non-medical use situation, e.g., to provide oxygen for a person experiencing altitude-related conditions, to a person in air with an undesirable air quality (e.g., an undesirable level of air pollution), to a person in very cold weather conditions (e.g., below 0 degrees C., such as less than −10, ~15, −20 degrees C.), or to assist athletes or the elderly in performing exercise.

In aspects, an operable device can optionally be used to assist with the performance of a medically relevant procedure, such as in performing CPR. In aspects, the device is a regulated medical device, and the components of the device are "medical grade."

In aspects, methods of the invention provide oxygen rich gas resuscitation to a user for lung/respiratory failure.

In aspects, methods of the invention deliver oxygen-rich gas (oxygen gas having any of the oxygen contents described herein, such as 88-98%, 90-95%, 90-98%, 93-95%, oxygen content) in an amount that is greater than (e.g., DOS greater than) 3 mmHg (e.g., 4, 4.5, 5, 5.5, or 6 mmHg) within a period of less than about 5, less than about 4, less than about 3.5, less than about 3,≤2.5, or ≤~2 minutes (e.g., 1.5-7.5, 1.5-6, 2-8, 2-6, 1-7, or 1-6 minutes).

In aspects, method(s) are performed to address an emergency situation either by the user or by an assistant assisting the targeted person/user.

In aspects, the use is a person who is unconscious or at risk of becoming unconscious (e.g., is showing one or more signs or symptoms of soon becoming unconscious, is going in and out of consciousness, has a history or a condition associated with becoming unconscious, etc.). In facets, the mouthguard component can DOS reduce the risk of loss of gas delivery, injury, or other negative outcomes in such a person.

In aspects, the user is a person having a condition wherein transmission of saliva materials is highly undesired, such as exposure to a chemical (e.g., to a drug, such as fentanyl) or to an infectious agent (e.g., a bacterium, fungi, other microorganism, or a virus, such as a coronavirus, HIV, influenza, or other virus). In aspects, the use of the device measurably/detectably or significantly reduces the rate of transmission of such or other possible saliva-associated agents to the assistant breathing through a variable input component as compared to performing traditional CPR-associated mouth-to-mouth resuscitation.

In aspects, the user is someone who requires the assistance of pure oxygen or substantially pure oxygen. In aspects, the operator performs the method in the presence of a detectable or significant amount of air particulates, a detectable or significant amount of one or more harmful gases, or both a detectable or significant amount of both air particulates and one or more harmful gases.

In aspects, a user is a person with a disease or condition, such as a condition that makes use of the device highly desirable as compared to existing gas delivery systems. In aspects, the user has epilepsy. In aspects, the user is a person with asthma. In aspects, the user is a person suffering from chronic obstructive pulmonary disease (COPD) or other type of respiratory disease, condition, or otherwise undergoing respiratory failure. In aspects, the user is a person undergoing a cardiac-related event, such as a heart attack or other coronary-related condition.

Methods of the invention can comprise (1) inserting a mouthpiece component into the mouth of a user, (2) sealing the lips of a user around the mouthpiece (e.g., fitting them around a lip seal component), (3) at least partially closing the nose of the user/treated person, and (4) pulse delivering gas (e.g., highly enriched oxygen) by (a) triggering the release mechanism of a gas container, (b) delivering breaths through a variable inlet tube, or (c) delivering other gas than an assistant's breath through the variable inlet tube (either the same or different from the "first gas" delivered through other engagement with a mouthpiece component). In aspects, a user delivers gas through a "first flow path" or "first route" from a primary gas container into the mouthpiece component and the user or an assistant also breathes into the variable inlet tube, or otherwise delivers a non-breath gas through the variable inlet tube, in sequence, concurrently, or both. In cases, methods include steps of assembling the device by attaching components or removing components (e.g., as a treated person regains consciousness).

In aspects, each gas delivery container used in the method (or included in a device) has a capacity of at least about 100, at least about 150, at least about 180, at least about 200, or at least about 220 one-second pulses (e.g., 150-350, 150-300, 180-300, 180-280, 180-260, 200-260, 220-300, 240-300, 240-340, 100-400, 50-400, 50-500, or 250-450 one second-pulses), typically by engaging a gas release component of a gas container of the device or by engaging some equivalent or otherwise effective gas release means. Such pulses can be sometimes described as "continuous" meaning that the gas is released throughout the entirety of the pulse.

In exemplary aspects, the invention provides a method of delivering a substance or an at least second substance to a target subject comprising (1) providing a variable inlet component; (2) ensuring attachment of the variable inlet component to a system or device (multi-port connector component/device), as applicable; (3) ensuring attachment of the of the inlet end of the variable inlet component with a source of the substance (i.e., the same gaseous substance as delivered via the gas container) or at least second substance (i.e., a gas different from the gas delivered to the user through the gas container); (4) an operator releasing the substance from the source of the substance or at least second substance into the variable inlet component such that the variable inlet component delivers the substance or at least second substance from the variable inlet component to the system or device, as applicable, to which it is attached (a) before a period in which a first substance is being delivered within the system or device to which the variable inlet component is attached, (b) after a period in which a first substance is being delivered within the system or device to which the variable inlet component is attached, or (c) during a period in which a first substance is being delivered within the system or device to which the variable inlet component is attached.

In aspects, methods can include providing a variable inlet component, (2) ensuring attachment of the variable inlet component to a system or device, (3) an operator orally engaging at least a portion of a variable inlet component, and (4) the operator exhaling a breath into the variable inlet component such that the variable inlet component delivers at least a portion of the exhaled breath from the variable inlet component to the system or device, as applicable, to which it is attached (a) before a period in which a first substance is being delivered within the system or device to which the variable inlet component is attached, (b) after a period in which a first substance is being delivered within the system or device to which the variable inlet component is attached, or (c) during a period in which a first substance is being delivered within the system or device to which the variable inlet component is attached (e.g., to augment the pressure of the gas delivered through the primary flow path from the gas container with human breath).

In aspects, a user/treated person is a person that has been poisoned, is undergoing a drug overdose, or both. In aspects, a user/treated person is a person having one or more development disabilities or similar mental health-associated special needs. In aspects, the user is a person in a pollution situation, debris/particulate environment, or fire. In aspects, a treated person is a person that has undergone smoke inhalation or other debris/particulate or harmful gas inhalation. In aspects, method(s) are performed to help revive a person that is unconscious or at risk of going unconscious. In aspects, a device is used when a user is facing a fire condition, pollution condition, or smoke condition, as a means to avoid injury associated with such an environment (by allowing the user to inhale therapeutic gas from the device and to normally exhale through his or her nose).

In aspects, a method comprises the operator of the device (e.g., an assistant) at least partially closing the nostrils of the target subject while simultaneously holding, operating, or both holding and operating the variable inlet component, the system or device to which it is attached, or any combination of any or all thereof.

In aspects, a treated person has an oxygen saturation ($SpO_2$) level of 95 or less, 93 or less, or 92 or less (e.g., a COVID patient with a relatively low oxygen saturation level). In aspects, a treated person has an oxygen saturation level of 91 or less, or 90 or less when treatment is initiated. In aspects, a person has an oxygen saturation level of 89 or less or 88 or less. In aspects, applying methods of the invention results in an enhancement of oxygen saturation of at least about 0.5 points, at least about 1 point, at least about 1.5 points, at least about 2 points, at least about 2.5 points, or even at least about 3 points or more such as about 4 points or about 5 points (5%) (e.g., 0.5-6 points, 0.5-5 points (%), 1-4 points, 1.5-6 points, 1.5-4.5 points, 0.5-4 points, 0.5-3 points, 0.5-3.5 points, 1-3 points, etc.) after a relevant treatment interval (e.g., after 2, 3, 5, 7, 10, 12, or 15 minutes of regular pulse delivery or after administration of at least about 33%, at least about 50%, at least about 75%, or about 100% of one, two, or more gas containers comprising a 5-15 L oxygen capacity, having capacity of delivering 100-300, e.g., 150-350 or 150-300, e.g., 200-250, 200-280, or 200-300 one-second pulses of gas to the treated person, or both). In aspects, devices of the invention are provided in a kit with other devices for evaluating health-related conditions, such as an oximeter for assessing a user's or treated person's oxygen saturation level. In aspects, methods are performed along with the diagnosis of such oxygen saturation condition or other conditions described here.

Assisted Use

In aspects, a person can assist the user in operating an operable device, e.g., in situations wherein the user may be unconscious, at risk of unconsciousness, or is incapable of self-operating the invention (e.g., the user is a child, elderly, or disabled).

In aspects, the method comprises the person assisting the user (the "assistant") attaching the mouthpiece component to the gas container before performing any other step of the method.

In either assistant-associated methods or user-performed methods, the method may comprise attaching the mouthpiece component to any one of various gas containers, e.g., a Boost Oxygen™ canister. In user-performed aspects, the method comprises the user engaging the gas release component(s) of the device/system/assembly.

In aspects, the method comprises the person assisting the user in placing the mouthpiece component of the device into the mouth of the user and engaging the gas release component.

In aspects, the method comprises the person assisting the user directly or indirectly, at least partially closing the nostrils of the user. For example, in aspects, the person assisting the user at least partially closes the nostrils of the user by action of one hand and operates the device by action of the other hand. In aspects, the gas release mechanism is adapted to be performable by most individuals of a class of individuals under such conditions (e.g., typical adult assistant users/users). In aspects, the weight of the device is such that it is readily held steady or even held in one hand. Closing the nostrils of the user DOS helps prevent the gaseous substance from escaping the user's mouth into the atmosphere, thus increasing the amount of gaseous substance that can enter the lungs of the user.

In aspects, the person assisting the user will engage the gas release component continuously until the user's symptoms are reduced, or the user is no longer unconscious or appears at risk of unconsciousness.

In aspects, an operable device (whether in an assistant-associated method or user-performed method) is operated for about 5-500, 10-400, 10-500, 5-400, 5-300, 5-200, 5-100, 50-50, 10-100, 10-200, 20-200, 20-400, 20-300, 25-250, 25-100, 25-50, 25-75, 10-50, or 10-30 one second continuous release pulses of gas.

In aspects, the gas release component is engaged continuously throughout the performance of the method. In aspects, the gas release component is engaged in short bursts (e.g., intervals of ~1, ~1-2, ~1-3, 1-4, ~1-5, ~1-6, ~1-7, ~1-8, ~1-9, or ~1-10 seconds). In aspects, the method comprises contacting emergency assistance. In aspects, the method comprises performing the method until a higher capacity oxygen delivery system is available. In aspects, the method comprises monitoring one or more vital signs of the user and discontinuing the application if conditions improve.

ILLUSTRATED EXEMPLARY EMBODIMENTS SHOWN IN THE DRAWINGS/FIGURES

The figures and the following description of aspects of the invention provided in connection therewith are provided for the purpose of further illustrating examples of devices and related components of the invention and the operation thereof. Such embodiments provided should not be construed as limiting (e.g., figures/components may not be drawn to scale; an element may be provided primarily for illustrating operation; and several alternative embodiments are within the scope of the invention (as also described elsewhere herein).

FIG. 1 is an isometric view of an exemplary embodiment of a portable gas delivery device (100). The main components of the exemplary portable gas delivery device (100) include a mouthpiece component (105) and a gas container (125). As described elsewhere, the device can be provided as an integral (non-separable) device or can be a selectively attachable/releasable assembly formed from two separate devices (e.g., a gas container that can act independently as a gas delivery system, such as an oxygen delivery system like the current on-market Boost Oxygen™ devices, and a releasable mouthpiece component.

The mouthpiece component (105) may comprise a right rear teeth engagement component (110), a left rear teeth engagement component (111), a mouthpiece first engagement end (115), a mouthpiece gas outlet (160), and a mouthpiece lip seal (165). The gas outlet is where gas from the gas container is delivered through the mouthpiece component. The teeth engagement features, as shown, may be separated. The mouthpiece can be made of a suitable material, which typically is mostly, generally entirely, substantially entirely, or entirely one or more silicone rubbers or material(s) of similar hardness properties, safety properties, durability, washability, and the like. The mouthpiece lip seal better seals the mouth when in use.

The gas container (125) may further comprise a gas release component (130) (exemplified here as a trigger) and a gas container engagement end.

The mouthpiece component may further comprise a mouthpiece gas inlet (not shown), which may be, e.g., located approximately between the mouthpiece first engagement end (115) and the gas container engagement end (135).

The gas container may further comprise a gas container gas outlet (not shown), located approximately between the mouthpiece first engagement end (115) and the gas container engagement end (135).

The right rear teeth engagement component (110) and the left rear teeth engagement component (111) are configured to receive the teeth of a user and are used to hold the portable gas delivery device (100) in place while in use. In aspects, the right rear teeth engagement component (110) and the left rear teeth engagement component (111) are at least mostly composed of one or more types of silicone rubber.

The mouthpiece lip seal (165) is configured to fit over the lips of a user and provides an airflow seal that prevents or substantially prevents gas from escaping into the atmosphere when the portable gas delivery device (100) is in use.

The gas container (125) is highly portable, typically having a gas holding capacity of 0.5-20 L. The gas container is composed of material(s) that are suitably inert and impervious to the contained gas, even under pressures (e.g., pressures of 100-500 psi, 100-300 psi, 100-250 psi, or 100-200 psi). In aspects, the gas is highly oxygenated (e.g., the gas comprised within the gas container (125) may comprise, e.g., 35-100% oxygen, such as about 75-95% oxygen, or about 90-95% oxygen, such as about 95% oxygen (e.g., 95-96% oxygen).

In aspects, the mouthpiece component (105) releasably sealingly engages the gas container (125). Further in aspects, the mouthpiece first engagement end (115) releasably sealingly engages the gas container engagement end (135) such that there is an airtight seal between the mouthpiece component (105) and the gas container (125). Even further, in aspects, this engagement allows for the transfer of gas from the gas container (125) into the mouthpiece component (105) when the gas releases component (130) is engaged. In this engagement, the mouthpiece gas inlet and gas container gas outlet are engaged and in alignment such that gas exiting the gas container (125) travels continuously through the gas container gas outlet and mouthpiece gas inlet into the mouthpiece component (105).

In use, the gas release component (130) may be engaged to release the gas from the gas container. In aspects, the gas release component (130) is a trigger. When the trigger is engaged, gas will be released from the portable gas delivery device (100) through the mouthpiece gas outlet (160) at an amount proportional to the amount of time that the trigger is engaged.

Figure 2:
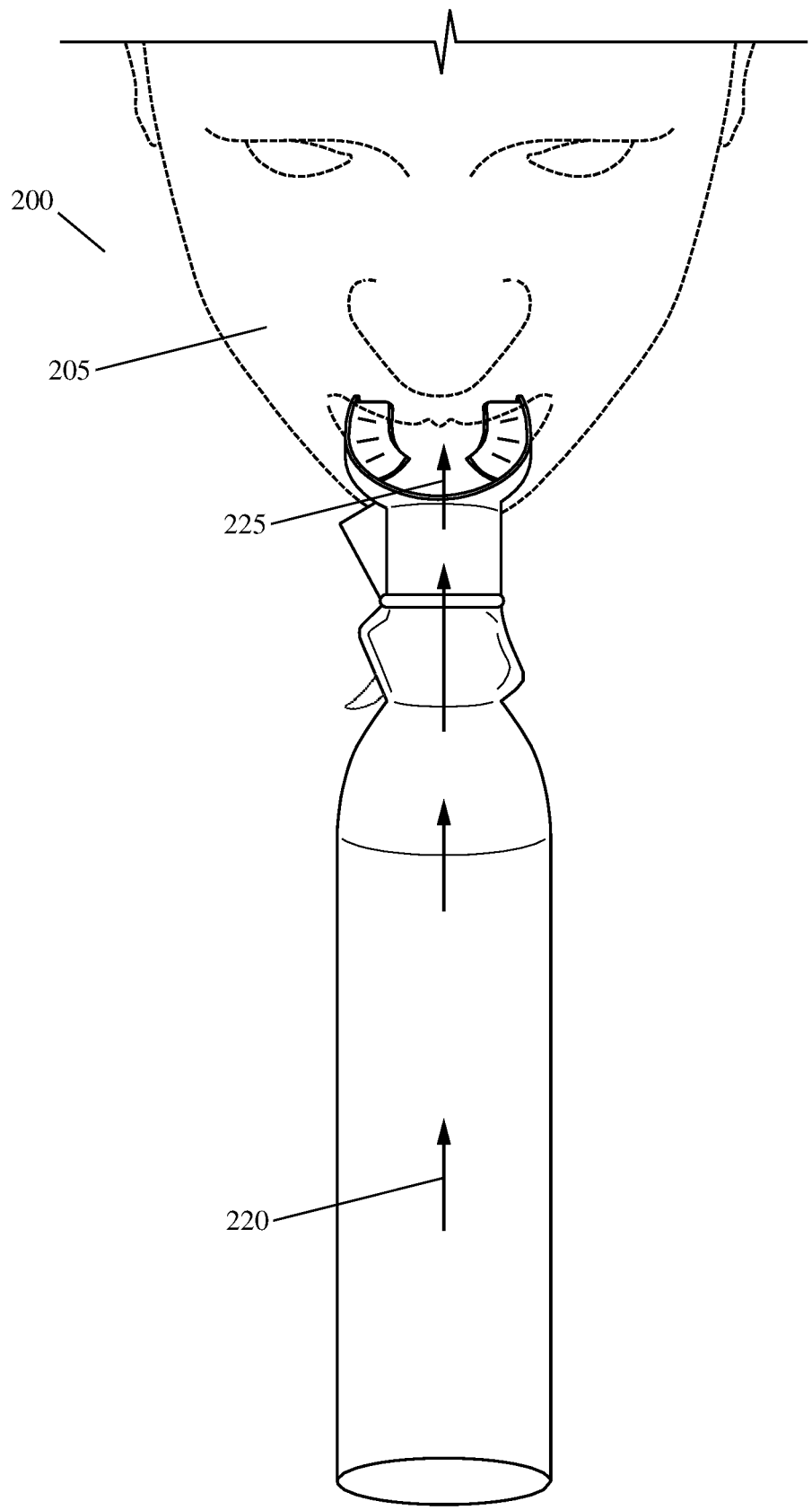
FIG. 2 is an isometric view of an exemplary device, as shown in FIG. 1, the device being used by a user and the figure illustrating the flow of gas ("airflow") through the device and into the user.

FIG. 2 is an isometric view of an exemplary portable gas delivery device and user system (200) in use. As shown, a user (205) engages the delivery device (100) and operates it by engaging with the gas release component. Engagement of the device results in a gas container airflow (220) and mouthpiece gas outlet airflow (225).

In aspects, a user (205) is someone suffering from a condition such as, but not limited to, asthma, an infection, such as a viral infection, such as a COVID-19 infection, or epilepsy. A user (205) may also be someone who is unconscious or at risk of unconsciousness.

The user (205) specifically engages the portable gas delivery device (100) by placing a portion of the mouthpiece component (105) in the user's mouth. The portable gas delivery device (100) can be held in place by the user (205) biting down on the right rear teeth engagement component (110) and left rear teeth engagement component.

In the same or further aspects, a user (205) or a person assisting the user operates the portable gas delivery device (100) by engaging the gas release component (130).

When the gas release component (130) is engaged, gas in the gas container (125) flows out of the gas container in the direction illustrated by the gas container airflow (220). The gas will continue to flow in the direction of the gas container airflow (220) through the gas container gas outlet and mouthpiece gas inlet. Finally, the gas exits the portable gas delivery device completely or substantially completely through the mouthpiece gas outlet (160) in the direction of the mouthpiece gas outlet airflow (225). In the same or further aspects, the gas will continue in the direction of the mouthpiece gas outlet airflow (225), at least until it enters the mouth of a user (205).

Figure 3:
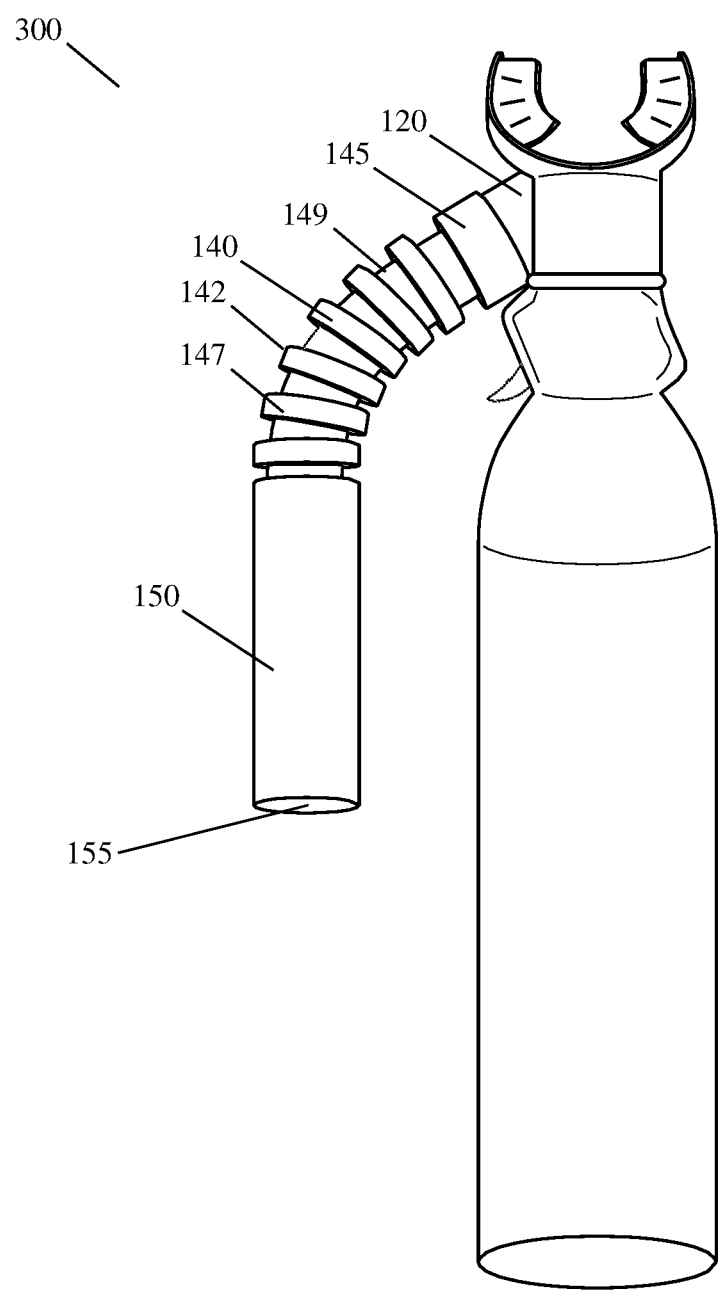
FIG. 3 is an isometric view of an exemplary assembled device/assembly of the invention comprising both a gas container component, e.g., an oxygen canister component, and a mouthpiece component with a variable inlet component, which sealingly and stably engages the gas container component.

FIG. 3 is an isometric view of an exemplary embodiment of a portable gas delivery device (300) further comprising a variable inlet component (140) (which may be described as a dual pathway or dual function device). In addition to the components of the exemplary device of FIG. 1, the exemplary portable gas delivery device with variable inlet component (300) further comprises a mouthpiece component access port or second engagement end (120) that engages the transition element (not labeled in FIG. 3—see above) of the device, and thus provides a secondary flow path or secondary pathway in which a secondary source of gas (apart from the gas container (not labeled in FIG. 3—see above)) provides gas to a user through the variable inlet component and through this access portion/second engagement end (120) of the device, through the transition element, and into the mouthguard of the mouthpiece component (again, such elements are not labeled in FIG. 3, but have the same structure as that described in FIGS. 1 and 2, above).

The variable inlet component (140) further comprises a variable inlet component engagement end (145), a variable inlet component contoured/first section (142) (which, in aspects can be a flexible part that is compressible or collapsible) and that comprises protruded sections (e.g., 147) and non-protruded sections (e.g., 149), and a variable inlet component body or second part/portion (150) (which, in aspects, may be removable from the first portion), and a variable inlet component inlet (155).

The variable inlet component (140) provides a means for delivering additional gas, such as oxygen, from the mouth of a person assisting a user to a user. In aspects, the variable inlet component (140) is or at least comprises in part, e.g., in the first portion (142), a flexible tube. In aspects, the variable inlet component (140) is somewhat or mostly made from (or the first portion, 142, is somewhat, mostly, or generally made from) a material such as polyvinyl chloride (PVC), polyurethane, silicone, rubber, nylon, etc. In aspects, some, most, or all of the variable inlet component (140) is expandable (e.g., the first portion, 142, may be collapsible or compressible, such as at 10-75% or 15-60% collapsible, 10-100%, 15-90%, 10-75%, 15-60%, 20-80%, less than 50%, more than 50%, 25-100%, 25-50%, or 25-75% compressible). Compressible/collapsible or not, the first portion (142) can comprise contoured/angled section/body as compared to the orientation of the gas container and second portion/body (150).

The mouthpiece's second engagement end/access port (120) can be configured to releasably sealingly engage the variable inlet component engagement end (145). In aspects, the mechanism for engagement may be a screw fastener, rubber hose fitting, cuff, bridge clamp, pin-lock, or any other suitable mechanism for attachment as described elsewhere.

The variable inlet component body (150) can be configured to engage an additional source of gas, such as an oxygen tank or the mouth of a person assisting a user. In aspects, a part of the variable inlet component body (150) (e.g., an end that is distal to the mouthpiece component) is threaded so that it can releasably sealingly engage an additional gas source, such as an oxygen tank. In aspects, the variable inlet component body (150) is made from a flexible material such as rubber or silicone. In aspects, the variable inlet component body (150) is composed of a material that is substantially less flexible than the first portion (142) of the variable inlet component. In aspects, the body (150) is designed to be removed from the first portion (142), such that a person may apply breathing through the first portion (142) when the body (150) is removed from the device, thereby decreasing the distance that the breath has to travel to reach a treated person. In aspects, the variable inlet component comprises a one-way valve that prevents flow of substances from the treated person to an assistant (not shown—interior to the component, but which can be positioned at or near the access port (120)). In aspects, the first portion (142) is compressible, but only partially so, to maintain distance between an assistant and a treated person.

The variable inlet component (140) can be configured to receive an additional source of gas and deliver the gas to the mouthpiece component (105 in, e.g., FIG. 1), wherein it is further delivered to the user. A second flow of gas can be delivered to the variable inlet component (140) by way of the variable inlet component inlet (155), thereby increasing pressure in the mouth of a user or delivering a gas with different compositional characteristics than the gas delivered through the primary pathway as shown in FIGS. 1 and 2.

Figure 4:
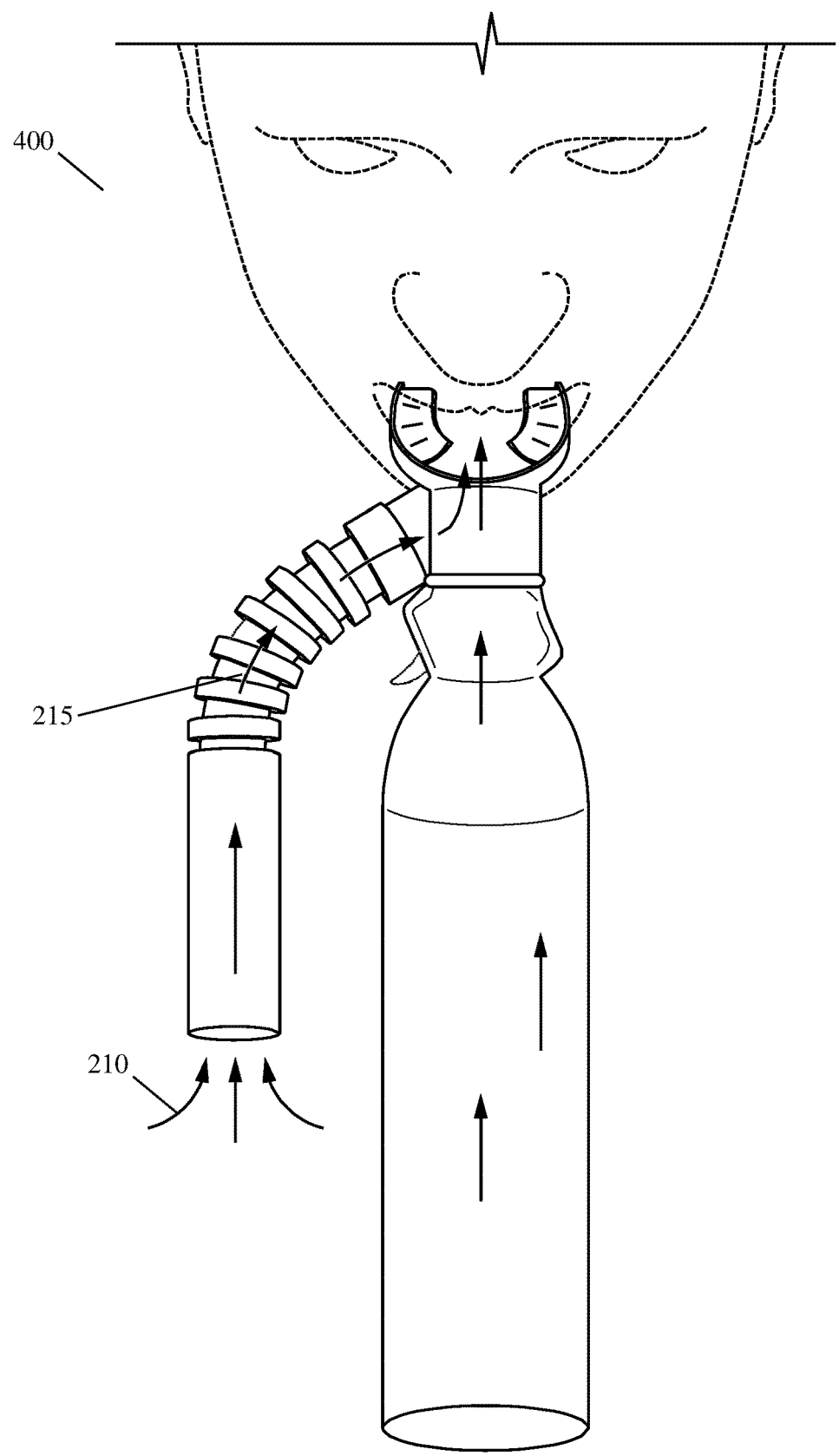
FIG. 4 is an isometric view of an exemplary device, as shown in FIG. 3, the device being used by a user and the figure illustrating the flow of gas ("airflow") through the device and into the user.

FIG. 4 is an isometric view of an exemplary portable gas delivery device with a variable inlet component and user system (400) in use. As shown, a user (205) engages the delivery device (300) and operates it by engaging with the gas release component. Engagement of the device results in a gas container airflow (220) and mouthpiece gas outlet airflow (225), as described previously in the description of FIG. 2, above. In addition, there is a variable inlet component inlet airflow (210) and variable inlet component airflow (215).

In aspects, a person assisting the user may place their mouth on the variable inlet component body (150) and blow air into the variable inlet component (140), thus providing an alternative to conventional mouth-to-mouth resuscitation (the assistant is not shown in the figure, but an airflow (210) is representative of any suitable secondary gas source that flows through the variable inlet component). In aspects, the air from the person's mouth will travel into the variable inlet component inlet (155) in the direction shown by the variable inlet component inlet airflow (210) and continue through the variable inlet component (140) in the direction shown by the variable inlet component airflow (215) until the air finally exits through the mouthpiece gas outlet (160) and into the mouth of the user (205).

In aspects, the variable inlet component (140) is releasably sealingly attached to an additional source of gas, such as another oxygen tank. Further, in aspects, gas is delivered from the additional source of gas through the variable inlet component (140) in the same airflow direction as described above.

REPRESENTATIVE USE EXAMPLES

The following detailed exemplary prophetic applications ("Examples") are provided to assist readers to understand better how devices of the invention can be applied in various settings. Any particular material(s), method(s), step(s), and condition(s) employed/described in the following Examples, and any result(s) thereof, are merely intended to further illustrate aspects of the invention. The method(s), finding(s), and principle(s) of such Examples, and the general implication(s) thereof, can be combined with any other part(s) of this disclosure. However, readers should understand that the scope of the invention is not limited by the overall content of these Examples or any part thereof.

Example 1

Two people ("Person A" and "Person B") are separately engaged in an outdoor activity in a remote environment (e.g., hiking) but are close enough in proximity to each other to observe one another.

Person A has packed two Boost Oxygen™ (e.g., 10 L or 12 L) devices in a kit further comprising two mouthpiece components of the invention (each comprising a flexible silicone rubber mouthguard comprising a gas flow outlet port, a transition element, and an engagement element for rapidly attaching/detaching the mouthpiece component to a Boost Oxygen™ device) and a variable inlet component comprising a flexible component that can be used for breathing air into the mouthpiece component (either as a means for delivering oxygen or as a means for motivating gas delivery from the gas device into the user/target/treated person) or that can be attached to other (secondary) gas delivery devices/sources.

Person A observes Person B is having difficulty breathing. Person A alerts emergency services of the situation. Person A then quickly assembles a mouthpiece device by attaching a mouthpiece component of the kit to one of the Boost Oxygen™ canisters and then offers the device to Person B. Person B takes one or more inhalation(s) of highly enriched (98%) oxygen from the Boost Oxygen™ canister through the mouthpiece component by self-operating the gas-release mechanism of the canister.

However, the condition of Person B worsens. Person B appears to be losing consciousness. As such, Person A assembles a complete device of the invention comprising both a mouthpiece component and a variable input tube, one or both attached to the second Boost Oxygen™ canister (e.g., the engagement component of the mouthpiece component still engaging the first Boost Oxygen canister and the engagement component of the variable inlet tube engaging the second Boost Oxygen canister). Person A is able to get Person B to place the mouthguard of the complete device into their mouth or, if necessary, can place the mouthguard into Person B's mouth, in either case in a manner that the mouthguard will remain in place, protecting Person B's mouth and also ensuring that the enriched oxygen flow continues to be delivered to Person B. Person A can also pace the delivery of the enriched oxygen gas to Person B by observing when Person B exhales and delivering pulses of enriched oxygen to Person B mostly, generally, or only when Person B is not exhaling. At times, Person A also or alternatively can close off Person B's nostrils to increase the efficiency of airflow delivery to Person A.

Person A then operates the Boost Oxygen™ canister of the second complete/operable device thereby continuing to administer or to facilitate the administration of 98% oxygen gas to Person B. Moreover, the mouthguard component of the device at this and other times in the performance of the method protects Person B from dangerous biting of the tongue, gums, or cheek, from choking, from damaging the jaws or teeth, or from not receiving oxygen delivery due to mouth closure that might occur with alternative gas delivery (e.g., alternative rescue oxygen delivery) system(s). The mouthpiece component of a device of the invention can in this and other aspects serve to maintain the open volume of a mouth of a treated person detectably or significantly, such as Person B.

If, for example, the Boost Oxygen™ canisters are depleted, Person A can continue to deliver at least some oxygen to Person B by breathing into the variable inlet component/tube. In such an exemplary case, Person A removes a detachable part of the variable inlet component and then compresses, collapses, or compresses and collapses the flexible portion while breathing into it. While the flexible portion collapses somewhat, it can, in this and other aspects, be not 100% collapsible, and, thus, a distance is still maintained between the mouth of Person A and the mouth of Person B (e.g., of 1, 2, 3, 4, or 5 inches). This distance allows Person A to be in sufficient proximity to Person B to deliver some amount of oxygen by breathing into the variable inlet component but to concurrently maintain a physical separation from Person B to avoid the transmission of chemical(s) or biologic agent(s) (e.g., fentanyl, viruses, bacteria, etc.).

Under different conditions, Person A might recover enough consciousness to begin to self-administer enriched oxygen through operation of the first Boost Oxygen™ gas storage device, delivering such oxygen through a primary flow path into the mouthpiece. At the same time, Person B can assist with the forcible delivery of the oxygen into the lungs of Person B by blowing into the variable inlet tube. The variable inlet tube can be associated with a one-way valve, thereby preventing any backflow of gas from Person B to Person A while Person A blows breaths into the variable inlet component.

When emergency services arrive, the emergency service personnel can, e.g., use the variable inlet component by reattaching the second portion of the variable inlet component, which comprises an interface for medical oxygen delivery system(s). The emergency service personnel then, as required, continue delivering highly concentrated oxygen to Person B through the mouthpiece component. The inclusion of another or alternative one-way valve either upstream of both the variable inlet component and transition element engagement component/mechanism or somewhere in the primary flow path (e.g., in the transition element at or near the engagement component that engages the first Boost Oxygen™ canister), can prevent backflow of gas associated with Person B into a gas delivery source, such as the Boost Oxygen canister.

Alternatively, if EMS personnel wish to use a primary flow path that would ordinarily be associated with a first gas storage device, the EMS personnel can either remove the variable inlet component or, e.g., disengage/close a one-way valve contained in the variable inlet component, thereby cutting off any flow of gas to the treated Person B other than through the intended primary flow path.

When Person B begins to recover consciousness, emergency services personnel can remove the variable inlet tube of the device and permit Person B to continue to self-administer oxygen from the Boost Oxygen™ can as desired or recommended. Alternatively, still, when Person B has sufficiently recovered, both the mouthpiece component and variable inlet component can be removed, and Person B can thereafter use the remaining enriched oxygen gas of the Boost Oxygen canister(s) through that device's ordinary delivery means.

Example 2

In her car, Person C maintains a kit that includes (1) mouthpiece component according to aspects of the invention (comprising a flexible contoured mouthguard and transition element comprising at least one access port and an engagement component that is designed to releasably, rapidly, and selectively engage a large (10 L or 12 L) Boost Oxygen™ device), (2) variable inlet tube that is configured to sealingly and releasably engage with the transition element of the mouthpiece component and that comprises a one-way valve, compressible/collapsible flexible portion, and second portion adapted to engage one or more gas sources (e.g., F size or G size oxygen containers commonly found in ambulances), and (3) a number of large/extra-large Boost Oxygen™ cannisters.

While Person C is driving through a suburban or urban location, she discovers unconscious Person D. Person D exhibits shallow, rapid breathing and sporadic movements, which might signal to a non-medically trained person that Person D is experiencing a seizure or a drug overdose. Given such facts, Person C calls emergency medical services. While waiting for help to arrive, rather than applying traditional mouth-to-mouth resuscitation to Person D, Person C quickly assembles a complete (three-way mode/three source assembled/complete/operable) device according to the invention (with mouthpiece component engaging a Boost Oxygen™ cannister as a gas storage container and a connected variable inlet tube). The rapid engagement mechanism allows Person C to assemble the device within a short period of time (less than 60 seconds with average adult users of ordinary cognitive and physical ability being able to assemble the device in 15-120 seconds).

Person C places the mouthpiece component into the mouth of Person D such that the mouthguard component makes contact with at least some of the teeth of Person D, thereby assisting in maintaining the mouth in a more open state providing for measurably or significantly greater open mouth volume and measurably or significantly aiding in a person in a state similar to Person D avoiding biting of his own tongue, cheek, etc.

Person C then engages the trigger of the engaged Boost Oxygen™ device to deliver pulse oxygen through the primary airflow passageway (from the Boost Oxygen™ cannister through most of the span of the transition element through the mouthpiece/mouthguard passageway and into the mouth of Person D). Person C may either compress Person D's nostrils or maintain Person D's lips in a more sealed state (if necessary) to promote filling of the lungs and better oxygenation through the pulse oxygen delivery (resulting in a measurably or significantly greater enhancement of lung volume, lung oxygen, or both, than, e.g., mouth-to-mouth techniques or use of an unmodified Boost Oxygen™ cannister).

Person C can either elect to solely allow Person D to exhale or can for at least part of the time while or after administering the pulse oxygen also breathe into the attached variable inlet tube, thereby adding pressure and gas volume in Person D's mouth, thereby promoting delivery of the gas mixture further into Person D's lungs and also slightly increasing carbon dioxide content, which may have, in some cases, beneficial effects, given the relatively low concentration of carbon dioxide in the gas mixture in the mouth. Person C can apply compression to the flexible portion of the variable inlet component (either lengthwise, with respect to the longest dimension of the component, the diameter of the component, or both, to increase the rate or efficacy of breath delivery, while maintaining a sufficiently safe distance such that the risk of transmission of harmful/undesirable substances in Person D's saliva to Person C through the variable inlet component is measurably or significantly reduced). The one-way valve of the variable inlet tube also measurably or detectably prevents the flow of materials from Person D to Person C.

Person C can continue to apply pulse oxygen (or pulse oxygen and breaths) and rests in several cycles while waiting for emergency medical services (EMS) to arrive. When EMS arrives, EMS personnel can use the second component of the variable inlet component and connect it with a gas source in an ambulance, e.g., a size F or size G standard ambulance oxygen container. EMS personnel may also be able to deliver other substances to Person D through either the primary pathway or secondary pathway (second flow path), such as delivering nitric oxide or helium or delivering pharmaceutical active ingredients, such as anti-narcotic agents if EMS determines that Person D is experiencing a drug overdose (e.g., delivering naloxone or other anti-narcotic active pharmaceutical ingredient (API) through the primary or secondary pathway). If Person D begins to recover, EMS personnel may remove the variable inlet tube. In cases, EMS personnel also may reverse the one-way valve of the variable inlet tube and apply suction through the variable inlet tube (or a portion thereof) to remove material from Person D.

This Example 2 and Example 1 both reflect the flexible nature of application of the devices of the invention in assisting treated persons with a variety of conditions.

CONSTRUCTION PRINCIPLES AND DESCRIPTION OF SELECT TERMS

This section offers guidelines for reading this disclosure.

General Terms and Principles

The intended audience for this disclosure ("readers") are persons having at least ordinary skill(s) in the practice of technologies discussed or used herein. Readers may also be called "skilled persons," and such technologies and related publicly available prior knowledge are collectively referred to as "the art." Terms such as "understood," "known," and "ordinary meaning" refer to the general knowledge of skilled persons.

The term "uncontradicted" means not contradicted by this disclosure or by logic, plausibility, or unsuitability based on the knowledge of skilled persons.

Disclosed here are several different but related exemplary aspects (variations) of the invention(s) described here (also referred to as, e.g., "cases," "facets," "respects," or "embodiments"). The invention encompasses all aspects as described individually and as can be arrived at by any combination of such individual aspects. Thus, any reference to "aspects" (e.g., "according to aspects" or "in an aspect") will be understood as referring to according to any and all of the other suitable aspects described herein. In this respect, the breadth and scope of the invention should not be limited by any exemplary aspect(s)/embodiment(s). No language in this disclosure should be construed as indicating any element/step is essential to the practice of the invention unless such a requirement is explicitly stated. Uncontradicted, any aspect(s) described in any part of this disclosure can be combined with any other aspect(s) in any other part.

Uncontradicted, all technical/scientific terms used here should be read, at least in one aspect, to have the same meanings as commonly understood by skilled persons, regardless of any narrower examples or descriptions provided here (including any term introduced initially in quotations). However, readers will also recognize that some aspects can characterized by the inclusion of elements, steps, features, characteristics, etc., associated with specific descriptions provided here and that such specific disclosures represent distinct embodiments of the invention apart from the corresponding aspect that is provided by interpreting the invention using any broader commonly used terminology or concept. Uncontradicted, disclosure of any aspect using known terms, which terms are narrowed by example or otherwise, implicitly discloses one or more related aspects in which the applicable terms are alternatively interpreted using the broadest reasonable interpretation of skilled persons.

Uncontradicted, the term "or" means "and/or" here, regardless of any occasional inclusion of the actual phrase "and/or" (e.g., phrases such as "A, B, or C" and "A, B, and/or C" each simultaneously discloses aspects including (1) all of A, B, and C; (2) A and C; (3) A and B; (4) B and C; (5) only A; (6) only B; and (7) only C (and also support sub-groupings, such as "A or B," "A or C," etc.)).

For conciseness, symbols are used where appropriate. E.g., "&" is used for "and," & "~" for "about." Symbols such as < and > are given their ordinary meaning (e.g., "≤" means "less than or equal to" & "≥" means "greater than or equal to"). A slash "/" between terms here can represent "or" ("A/B" means "A or B") or identify synonyms of an element, depending on context. The inclusion of "(s)" after an element or a step indicates that ≥1 of such an element is present, step performed, and the like. E.g., "element(s)" refers to both 1 element and ≥2 elements, with the understanding that each thereof is an independent aspect of the invention.

Uncontradicted, the term "also" means "also or alternatively." Uncontradicted, the terms "here" & "herein" mean "in this disclosure." The term "i.a." ("ia" or "ia") means "inter alia" or "(possibly) among other things." "Also known as" is abbreviated "aka" or "AKA." (and can mean is otherwise referred to, even if the relationship between the terms is not well known). The term "elsewhere" means "elsewhere herein."

Use of the abbreviation "etc." (or "et cetera") in association with a list of elements/steps means any or all suitable combinations of the recited elements/steps or any known equivalents of such recited elements/steps for achieving the function(s) of such elements/steps known in the art. Readers should interpret phrases like "and the like" similarly.

Uncontradicted, terms such as "and combinations," "or combinations," and "combinations thereof," etc., regarding listed elements/steps, means any or all possible/suitable combinations of the associated elements/steps. Thus, e.g., uncontradicted, a phrase like "combination of any thereof" refers to any or all combinations.

Aspects may be described as suitable for use(s) disclosed herein. Uncontradicted, terms such as "suitable" or "suitability" mean acceptable, appropriate, or, in aspects practical for performing a particular function/achieving particular state(s)/outcome(s), and typically means effective, practical, and non-deleterious/harmful in the context the term is used. E.g., uncontradicted, the term "suitable" means appropriate, acceptable, or in contexts sufficient, or providing at least generally or substantially all an intended function, without causing or imparting significant negative/detrimental impact. Additional suitability characteristics of certain aspects of the invention may be described below. Uncontradicted, each element of the invention is suitable for its intended use.

Uncontradicted, heading(s) (e.g., "Construction and Terms") and subheadings here are included for convenience and do not limit the scope of any aspect(s). Uncontradicted, aspect(s), step(s), or element(s) described under one heading can apply to other aspect(s) or step(s)/element(s) here.

Ranges of values here represent each value falling within a range within an order of magnitude of the smallest endpoint of the range without having to write each value of the range explicitly. E.g., a recited range of 1-2 implicitly discloses each of 1.0, 1.1, 1.2, . . . 1.9, and 2.0, and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593). Uncontradicted, readers will understand that any two values in a range provided as a list herein can be combined as endpoints to form a range defining a more particular aspect of the invention (e.g., if a list of values 1, 2, 3, 4, and 5 of element X is provided, readers will understand that the disclosure implicitly discloses an aspect comprising 2-4 X, 3-5 X, and 1-3 X, etc.

Terms of approximation (e.g., "about," "~," or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10—about 20"). The scope of value(s) encompassed by an approximate term typically depends on the context of the disclosure, criticality or operability, statistical significance, understanding of the art, etc. In the absence of guidance here or in the art for an element, terms such as "about" when used in connection with an element should be interpreted as ±10% of the indicated value(s) and implicitly disclosing ±5%, ±2%, ±1%, and ±0.5%.

This disclosure includes aspects associated with particular characteristics, such as amounts of components (or ranges thereof), In cases, several such characteristics of varying scope may be provided. Readers will understand that each such characteristic can be associated with particular properties that distinguish such aspects from other aspects, and, accordingly, each such range can be viewed as critical to a particular aspect of the invention, even if the associated results, properties, functions, etc., associated with such aspects are not directly communicated in association with such characteristics.

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/step implicitly discloses the corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys."

"Significant" and "significantly" mean results/characteristics that are statistically significant using ≥1 appropriate test(s)/trial(s) in the given context (e.g., p≤0.05/0.01). "Detectable" means measurably present/different using known detection tools/techniques. The acronym "DOS" (or "DoS") means "detectable(ly) or significant(ly)." The term "measurably" means at a measurable level. The term detectable provides implicit disclosure for aspects that are "measurable" and the term "measurable" implicitly supports aspects where the measured or measurable element is "detectable."

Uncontradicted, any value provided here that is not accompanied by a unit of measurement (e.g., a weight of 50 or a length of 20), either any previously provided unit for the same element/step or the same type of element/step will apply, or, in cases where no such disclosure exists, the unit most used in association with such an element/step in the art applies.

Uncontradicted, the terms "including," "containing," "comprising," and "having" mean "including, but not limited to," or "including, without limitation." Uncontradicted, use of terms such as comprising and including regarding elements/steps means including any detectable number or amount of an element or including any detectable performance of a step/number of steps (with or without other elements/steps). Uncontradicted, "a" means one or more, even when terms such as "one or more" or "at least one" are used in association with the referent "a."

For conciseness, description of an aspect "comprising" or "including" an element, with respect to a collection/whole (e.g., a system, device, or composition), implicitly provides support for any detectable amount/number or ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the whole/collection being made up of the element, or essentially all of the whole/collection being made up of the element (i.e., that the collection consists essentially of the referenced element). Similarly, a method described as including a step with respect to an effect/outcome implicitly provides support for the referenced step, providing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the effect/outcome, representing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the steps/effort performed, or both. Explicit listing of percentages of elements in connection with particular aspects does not limit or contradict such implicit disclosure. Uncontradicted, readers should interpret terms such as "essentially all" or "essentially" consistent with the concept of "consisting essentially of."

Uncontradicted, terms such as "comprising" when used in connection with a step of a method provide implicit support for performing the step once, ≥2 times, or until an associated function/effect is achieved.

Uncontradicted, any disclosure of an object or method (e.g., composition, device, or system) "comprising" or "including" element(s) provides implicit support for an alternative corresponding aspect that is characterized by the object consisting of that element or "consisting essentially of" that element (excluding anything that would "materially affect" the "basic and novel characteristic(s)" of the invention). Uncontradicted, any specific use of phrases such as "consists of" and "consists essentially of" herein does not modify this construction principle.

Readers will understand the "basic and novel characteristic(s)" of the invention, and the scope of what constitutes a "material affect" (or "material effect") of such "basic and novel characteristics" will vary with the specific applicable aspect. In aspects, the basic and novel characteristics include one or more intended functions and levels of performance. In one aspect, the basic and novel characteristics include suitability, effectiveness, or both. The basic and novel characteristics of any aspect of the invention also include, of course, any specific recited and associated elements of an aspect. In an aspect, a material effect is an effect that reduces, diminishes, eliminates, counteracts, cancels, or prevents one or more of such functions in one or more respects (e.g., delaying onset, reducing scope, reducing duration, reducing output, reducing the level of applicability, reducing effect, or combinations thereof). In an aspect, a material effect is one that changes such functions by making such functions impractical, difficult to obtain, or materially more expensive or otherwise costly in terms of inputs. From this and the other guidance provided herein, readers can understand the scope of an aspect that is defined by consisting essentially of a collection of elements. E.g., a composition that consists essentially of elements A and B, which are helpful towards human health, would exclude element C, which is known to reduce the efficacy of A, and also exclude element D, which is known to be toxic."

Uncontradicted, the term "one" means a single type, single iteration/copy/thing, of a recited element or step, or both, which will be clear from context. For example, the referent "one" used with respect to a component of a composition/article or system can refer to one type of element (which may be present in numerous copies, as in the case of an ingredient in a composition) one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a type of component of a composition/system/article).

Uncontradicted, the term "some" means ≥2 copies/instances or ≥5% (e.g., ≥7.5%, ≥12.5%, ≥17.5%, ≥27.5%, or ≥37.5%) of a listed collection/whole is or is made up of an element. Regarding methods, some means ≥5% of an effect, effort, or both is made up of or is attributable to a step (e.g., as in "some of the method is performed by step Y") or indicates a step is performed ≥2 times (e.g., as in "step X is repeated some number of times"). Terms such as "predominately," "most," or "mostly" (and "primarily" when not used to refer to an order of events or "mainly") means detectably ≥50% (e.g., mostly comprises, predominately includes, etc., mean ≥50%) (e.g., a system that mostly includes element X is composed of ≥50% of element X). The term "generally" means ≥75% (e.g., generally consists of, generally associated with, generally comprises, etc., means ≥75%) (e.g., a method that generally consists of step X means that 75% of the effort or effect of the method is attributable to step X). "Substantially" or "nearly" means ≥95% (e.g., nearly all, substantially consists of, etc., mean ≥95%) (e.g., a collection that nearly entirely is made up of element X means that at least 95% of the elements in the collection are element X). Terms such as "generally free" of an element or "generally lacking" an element mean comprising ≤25-% of an element, and terms such as "substantially free" of an element mean comprising ≤~5% of an element. Uncontradicted, any aspect described as "generally comprising" or "generally consisting" of an element implicitly discloses an element that "substantially comprises" the element. The same principle applies to disclosure wherein an aspect is described as being "generally free" of an element.

Uncontradicted, phrases such as "substantially identical" or "substantially similar" may be used to refer to element(s)/component(s)/ingredient(s)/thing(s) (e.g., composition, system, device, etc.) or step(s)/method(s) that have the same or about the same characteristic(s) or achieve the same or about the same result(s), typically in a similar way, as a referenced element/thing or step/method or otherwise do not meaningfully differ in intended result and manner of achieving such a result or are otherwise recognized in the art as not differing or not differing substantially in the relevant context (e.g., by being considered equivalents). Uncontradicted, readers will understand that a "substantially identical" or "substantially similar" element/thing or step/method when compared to a comparator thing/element or method/step means that the referenced element/thing or step/method exhibits such a similar function as a comparator at identical, approximately identical, or statistically similar amounts as the comparator thing or method when applied under similar conditions of use. Again, where statistical, approximate, or other measured comparisons are not possible, readers will understand the phrase as encompassing those things known as being identical or substantially identical to the referenced element/step or are described as such herein.

Uncontradicted, any aspect described with respect to an optionally present element(s)/step(s) also provides implicit support for corresponding aspect(s) in which one, some, most, generally all, nearly all, essentially all, or all such element(s) are lacking/step(s) not performed, in respect of the relevant aspect. E.g., disclosure of a system comprising element X implicitly also supports a system lacking element X. That is, readers will understand that any element, feature, step, or characteristic of any aspect of the invention recited herein as being present in an aspect also implicitly provides support for the element, feature, step, or characteristic as being excluded from a corresponding/similar aspect of the invention implicitly disclosed by the explicit positive disclosure. Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C can be performed in the order C, B, and A; B and A and C simultaneously, etc.). Uncontradicted, elements of a composition can be assembled in any suitable manner by any suitable method. In general, any methods and materials similar or equivalent to those described here can be used in the practice of embodiments in at least the broadest version of the relevant aspect. Uncontradicted, the use of ordinal numbers such as "first," "second," "third," and so on is primarily, though not exclusively, intended to distinguish respective elements rather than to limit the disclosure to a particular order of those elements, importance, or configuration.

Any elements associated with a function can be alternatively described as "means for" performing a function in a composition/device/system or a "step for" performing a part of a method, and parts of this disclosure refer to "equivalents," which means known equivalents known in the art for achieving a referenced function associated with disclosed mean(s)/step(s). However, no element of this disclosure or claim should be interpreted as limited to a "means-plus-function" or "step-plus-function" construction unless such intent is clearly indicated by the use of the terms "means for" or "step for." Terms such as "configured to" or "adapted to" do not indicate "means-plus-function" interpretation but, rather, describe element(s)/step(s) configured to, designed to, selected to, or adapted to achieve a certain performance, characteristic, property, or the like using teachings provided here or in the art.

As used herein, the word "exemplary" means "serving as an example, instance, or illustration." Any embodiment described herein as "exemplary" or "illustrative" should not necessarily be construed as preferred or advantageous over other embodiments. Any embodiment described herein as "exemplary" is not necessarily to be construed as preferred or advantageous over other embodiments.

Except where explicitly indicated or clearly indicated by context, terms such as "improved" or "better" mean DOS "increased." In some respects, terms such as "improved" means DOS "reduced," such as with respect to the toxicity of a composition. Uncontradicted, terms such as "enhanced," "improved," "better," and the like are used synonymously.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. Uncontradicted, in the event of any conflict between this disclosure and the teachings of such documents, the content of this disclosure takes precedence regarding interpreting aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

While elements disclosed in such incorporated references can be combined with aspects of the invention disclosed herein, readers will understand that the invention is intended to stand apart from such disclosures and, accordingly, uncontradicted, in aspects, any element(s) of the objects or methods of any such references are excluded from the scope of the invention (e.g., if reference A discloses object or element B, any aspect that is not directed to object or element B can be characterized by, as one aspect, the lack of object or element B).

All original claims contained in this disclosure, when filed, are incorporated into this specification as if they were a part of the description.

Terms and Principles Relating to Devices/Systems and Related Methods

Uncontradicted, the term "part" refers to a portion of a device, component, system, or assembly that is characterized by a unique construction or composition and which is separate from, is separable from, or was at least at one point in time (e.g., during manufacturing of the associated device) separable/separated from one or more other part(s) or component(s) (e.g., where the applicable part represents one of a plurality of parts of an assembly).

Uncontradicted, the term "component" describes a part or collection of associated parts that perform one or more defined functions. A function can, depending on context, be selectively performed, conditionally performed, or both, or can be performed at all times during operation or can be an inherent feature of a part or component.

Uncontradicted, the term "mechanism" describes feature(s), part(s), component(s), or combination(s) thereof that cause(s) or promote(s) the interaction of two or more elements (parts, components, devices, or combinations thereof, etc.). Often, but not always, a mechanism may be composed of two parts, features, or a combination thereof that performs the interaction (e.g., a hook part and a loop part in a hook-and-loop attachment mechanism). In certain aspects, a "mechanism" can be represented as a single part, feature, or component, as in, for example, a magnet.

Uncontradicted, the term "assembly" refers to a component formed by an assembly of previously separated parts.

Uncontradicted, the term "feature" is used to describe a portion of a part or component that is associated with a well-defined structure, composition/material(s), or function.

In certain contexts, herein, the term "element" may be used to reference a part, component, mechanism, device, system, or assembly. For example, disclosure herein may use the phrase "the X element" of the "Y component." Readers will recognize the term "element" also can be generally used herein to describe a thing (an object, such as a device, composition, system, etc.) or a part of a thing.

In the context of the present invention, some structures/objects can be considered devices or components of a large device (e.g., an assembly or system). In this respect, readers will understand that the use of the term "component" for referring to any such object/structure (e.g., a mouthpiece component) implicitly describes corresponding aspects where the structure is a free-standing/independent, separate device, and vice versa.

This paragraph exemplifies the use of such terminology. A rolling component of an automobile can comprise one or more axles and one or more wheels. Each wheel can, e.g., be a part of the rolling component, as can, e.g., each axel. Also, each wheel can be a component comprising its own parts, such as, e.g., a rubber tire and a wheel rim. A rolling mechanism can be, e.g., at least one axel and at least one wheel, wherein the mechanism facilitates the movement of the automobile. Further, an axel and, e.g., at least two wheels, may form an assembly. The particular design of the tread on the rubber tire of a wheel can be, e.g., a feature of the rubber tire. In describing the automobile, one may reference, for example, a/the "wheel element."

Terms related to orientation may be used here to describe the positioning of a part, component, or, e.g., an assembly in space (spatial positioning or spatial orientation) relative to one or more other part(s), component(s), or assembly(ies). For example, terms such as "longitudinal," "lateral," and "vertical" can be used herein to refer to what would be understood by readers to correspond to an x-axis, y-axis, and z-axis, respectively, of a device or other element (the x-axis and y-axis being perpendicular in the relevant plane and the z-axis being oriented away from, above or below the plane). Such terminology can refer to the orientation of part(s), component(s), and, e.g., device(s), etc. The term "horizontal" can be used to mean either longitudinal or lateral, i.e., not vertical. Readers will understand when other similar positional terms are also used. For example, the term "length" may be used in place of "longitude," the term "width" or "thickness" (or, where applicable, circumference) may be used in place of "lateral," and terms such as "height" or terms such as "up" and "down" (or upper and lower) may be used in place of "vertical." Ordinarily, the vertical access in a description or a figure is oriented in the manner in which gravity acts and on a page ordinarily will correspond to the top and bottom of the page when viewed by a reader. Ordinarily, the longitudinal direction (length) will refer to the direction of right-to-left in a figure or description, and the lateral direction refers to the direction perpendicular thereto (e.g., in the same plane) (but ordinarily representing objects towards the reader and away from the reader rather than to the right, left, or center of the reader). Often, the lateral dimension (width, thickness, or depth) can be considered to "come in and out of the page" (i.e., projecting towards or away from the reader). Such terms can also describe how a device or element is oriented/viewed, usually consistent with the longest measurement/dimension of the element/device in ordinary use. For example, a device that is longitudinally oriented will have its longest dimension in the longitudinal coordinate (longest measurement along or parallel to the longitudinal axis). Ordinarily, a device or other element is displayed or described consistent with its orientation in ordinary or primary use (e.g., a device is typically described as positioned longitudinally if used longitudinally). For example, although an automobile might be shown as aligned vertically, it is, consistent with these principles, ordinarily described and displayed as horizontally aligned because that is the way the automobile is ordinarily used, and its length is measured from rear bumper to front bumper because that is the largest horizontal dimension of the car in such a view). However, one might illustrate a car vertically, in which case the measures of length, width, and height of the car would change from those measures in the horizontally aligned car, but readers will understand that the size of the parts of the car are the same only the orientation of the car has changed.

Terms like "proximal" and "distal" or "near" and "far" can be used in relationship to objects, usually to two or more objects, to describe relative distances. Uncontradicted, such terms are not meant to imply any specific limitation on position, at least with respect to the broadest disclosed relevant aspect. Despite the foregoing, uncontradicted, terms such as "longitudinal," "transversal," "orthogonal," "vertical," "on," "under," "in front of," "behind," "left," "right," "vertical," "horizontal," "top," "bottom," "inside," "outside," etc. that indicate the directions or positions based on the directions or positions shown in the drawings or in the description of the directions or positions in a device, component, or part commonly placed, are, at least in one aspect, only for the purpose of describing the present disclosure and simplifying the descriptions, but not intended to indicate or imply that a device or a component has a compulsory position or must be structured or operated in a specific position, hence not to be considered as limitations to the full scope of the present disclosure.

In view of the preceding paragraphs, terms such as "top" and "bottom" or "upper" and "lower" may be used to refer to the position of parts, components, etc., in this disclosure. Uncontradicted, readers should interpret such terms as merely terms of context (e.g., referring to a particular figure) or convenience. In certain embodiments where there is some functionality associated with the placement, terms such as "top" and "bottom" may have a more definite meaning in a particular context, at least in aspects (e.g., with respect to orientation to the horizon, another part/component, etc.).

Axes relating to the orientation of a device or element also can be used in the description of such a device or element. For example, an imaginary line drawn through the longest dimension of a device herein may be referred to as a "long axis" or "longitudinal axis" of the device. Other elements may be described as perpendicular, parallel, aligned with/overlapping, being the same (or substantially the same), or being non-overlapping, non-aligned, etc., with respect to such an axis.

Uncontradicted, herein, terms such as "interface," "engage," and, e.g., "cooperate" may be used to describe the interaction of two or more part(s), component(s), or assembly(ies) or combination(s) thereof. Uncontradicted, the term "interface" is used to describe physical contact, such as, e.g., part A interfacing with part B means that part A makes physical contact with part B. Uncontradicted, "engage" also means to affect activity detectably or significantly. Further, "engage" may be used to indicate an active interface, such as, e.g., a magnetic attraction between two parts, such that while the activity of a part may not be visually perceivable, an attractive activity is present. For example, a part/component/feature called X engaging a part/component/feature called Y can mean that, e.g., the activity of X detectably or significantly affects the activity of part Y, or, also or alternatively, there is a non-visible activity occurring between X and Y, such as, e.g., the engagement between X and Y is a magnetic attraction. "Engage" may, in aspects, also mean to affect activity detectably or significantly but may not require a direct/touching (contacting) interface (e.g., may not involve direct attachment or other contact). Accordingly, a part/component/feature called X that "engages" a part/component/feature called Y can mean that, e.g., activity of X detectably or significantly affects the activity of (acts on, applies a detectable force on, etc.) part Y, or, also or alternatively, there is a non-visible activity occurring between X and Y, such as, e.g., the engagement between X and Y is a magnetic attraction, wherein X and Y do not make physical contact. Uncontradicted, herein the term "cooperate" can be used to describe two or more part(s), component(s), or assembly(ies) or combination(s) thereof which act together to perform a function, as in, for example, two or more airflow limiting parts which cooperate to establish and airflow control setting of a device.

Terms such as "selectively," "selectable," "releasably," "releasable," and, e.g., "controllable" may be used to describe the functionality of one or more part, component, or assembly (or combination(s) thereof), the state of the interface(s) or engagement(s) of one or more part(s), component(s), or assembly(ies) (or combination(s) thereof), one or more operation status(s) or setting(s) of a delivery device, or the like. Uncontradicted terms such as "selectively" or "selectable" mean designed to be, able to be, or which otherwise are established/set by a device user (e.g., an airflow control setting could be "selectable" such that it can be "selectively" open or "selectively" closed (or, e.g., a feature could be, e.g., selectively on/off, active/inactive, functional/non-functional, etc.) or selectively more or selectively less). Uncontradicted, the terms "releasably" and "releasable" mean that two or more referenced parts, components, assemblies, elements, features, or combinations thereof, which can be at least detectably or significantly engaged but which can be disengaged from one another. For example, part A and part B can be "selectively releasable," meaning that part A and part B are able to be engaged or disengaged from one another as established by a device user. Uncontradicted, a "secure" or "fixed" engagement or attachment means an engagement that is not intended to be releasable or that would not be releasable in ordinary intended operation or if released, would reduce or eliminate or limit operability.

Uncontradicted, the term "controllable" (or "adjustable") means adjustable in degree, amount, timing, or other characteristic(s) of operation according to user aim(s), desire(s), target use(s), or other user preference(s). A controllable/adjustable component allows for ≥2 conditions or states (e.g., degree of airflow control) that can be selected by a user (e.g., ≥3, ≥5, ≥7, ≥10, ≥15, ≥20, ≥25, etc.). In other aspects, a device can also or alternatively comprise an element that is selectable but not controllable. Such an element can allow for a function to be performed but without setting the degree of the function. A selectable element does not necessarily mean that the selected element is entirely on or off, but, rather, can, in aspects, mean that it (the condition, characteristic, operation) changed from one state/setting to another when a selection is made.

In aspects such as where this disclosure describes an exemplary element having a particular shape (e.g., a "barrel," etc.), readers will understand that, uncontradicted, such disclosure implicitly provides alternative aspect(s) in which the form of the element is any suitable shape or known suitable alternative shape, and that for any shape provided herein, the disclosure implicitly discloses any known suitable subtypes of such shapes as individual aspects of the invention (e.g., any tubular structure described herein can be, uncontradicted, a square, rectangular, cylindrical, round (pipe-shaped), or other suitably shaped tube).

Terms and Principles Specific to this Disclosure

In aspects, airflow (gas flow) through a device or component can be described as "upstream" or "downstream" of some reference element. Uncontradicted, "upstream" means airflow (or a location in an airflow element) located relatively more towards the airflow inlet or source with respect to referenced element(s), and "downstream" means airflow (or a location in an airflow element) located relatively closer to the airflow outlet (usually a user interface or component) than the referenced element(s).

Uncontradicted, the term "airflow" is not limited to air but can represent the flow of any gas disclosed herein, such as purified oxygen or an oxygen-containing composition, including elements of air or other gaseous elements/compounds. In general, readers will understand that references to "air," such as in terms like "airflow" and "airtight," implicitly disclose corresponding aspects relating to non-air gasses, such as enriched oxygen gas compositions (e.g., pressurized oxygen comprising 35-95%, 50-95%, or 75-95% oxygen).

Devices herein comprise element(s) composed of materials that are designed/adapted to retain gas(es) within airflow areas (channels, passages, etc.). Such material(s) can be characterized as being impervious, inert, impermeable, etc. In general, any material described herein as impervious, inert, or impermeable provides implicit support for the material exhibiting two of such characteristics or all three of such characteristics. Inert, as may be described elsewhere, generally means unreactive with the gas(es). Impermeable refers to the lack of the gas(es) to permeate the material(s) detectably or significantly. Impervious refers to the lack of gas(es) to escape from (be inadvertently released from) the area surrounded by the material (or having the ability to contain the gas(es) substantially, essentially, or entirely under normal operating conditions).

Terms such as "outlet" and "inlet," like other terms herein, can represent multiple elements to provide the indicated structure/function. For example, an outlet can comprise many outlet channels/orifices or a single hole/opening, etc.

Herein, uncontradicted, a gas delivery/breathing apparatus or device of the invention is ordinarily described and displayed in a vertical orientation as this reflects the typical alignment of such a device's use (i.e., when a user engages with the delivery device). Thus, e.g., a mouthguard component, as shown in the figures provided herein, may be described as having a length that is defined as the distance between the furthest apart ends of the mouthguard on the right and left sides of the figure, a height that refers to the distance from the top to the bottom of the mouthguard (e.g., ranging from a portion covering the most forward teeth/lip(s) in a person when in use to the portion that extends furthers into the user's mouth) and a depth or thickness referring to the measure from the bottommost portion to the topmost portion when a user wears the mouthguard. In other aspects, a mouthguard might be described in the orientation it is used by placement into the mouth of a user, in which case the height described above would be equal to the depth/width in this second orientation, and the depth/width described above would be equal to the height in this second orientation. Readers will be able to determine which orientation is being described from the measurements and units provided. For example, mouthguard components can be described as having a height of about 1-3 cm, which ordinarily will be recognized as referring to a mouthpiece that is oriented as used in a user's mouth.

The term thickness here and in references incorporated herein also sometimes can refer to the height or depth of the mouthguard component material along a particular tooth surface (e.g., the occlusal aspect, the labial aspect, the palatal aspect, etc.). E.g., a mouthpiece component can have a "thickness" of about 2.5-3.5 mm, 2.75-3.25 mm, or 2.9-3.1 mm on the labial aspects, about 1.75-2.25, 1.85-2.15, or 1.9-2.1 along the occlusal aspect, a labial flange extending within 1.8-2.2 or 1.9-2.1 mm of the vestibular reflection, or about 0.8-1.2, 0.85-1.15, 00.9-1.1 along the palatal aspect, the palatal flange extending about 8-12 mm or 9-11 mm (e.g., about 10 mm) above the gingival margin, or a combination thereof. Such aspects of mouthpiece design are described in e.g., Sousa et al. (2020). Polymers. 12. 1490.

doi: 10.3390/polym12071490. Again, readers will understand when "thickness" is used in such a manner by the context of use, including the relevant measurements used in the description.

Elements of the invention relate to the provision of amounts of materials, e.g., the amount of gaseous substance that is released by a device and delivered to a user over/during a period of administration/action of a device (e.g., a pulse of delivery, etc.). In general, the amount of the gaseous substance delivered by the number of typical/intended application(s) is an effective amount. Similarly, the concentration of the gas, e.g., of oxygen, will be an effective concentration. Terms such as "effective amounts" mean an amount that is effective for the described function(s) of the associated element (e.g., the amount of oxygen delivered to a user being effective to prevent, treat, or promote the prevention or treatment of a condition). Uncontradicted, readers will understand that any element that is associated with such a function that is not characterized as being associated with a specific amount, concentration, etc., is present in an effective amount, effective concentration, etc.

Uncontradicted, terms such as "adapted to" mean that the associated element is designed to be capable of an engagement/interaction, performing a function, etc., as indicated. Terms such as "specifically adapted to" means that an element is specifically designed to engage with a particular or particular set of device(s), component(s), etc., or to carry out (conduct) a specific function or conduct a function in a specific manner, as described herein. E.g., a component that is specifically adapted to engage a counterpart component is designed to preferentially bind that counterpart component or only bind to the counterpart component (e.g., by specific size, engagement means, etc.).

Uncontradicted, readers will understand that any element, feature, step, or characteristic of any aspect of the invention recited herein as being present in an aspect also implicitly provides support for such element, feature, step, or characteristic as being excluded from a corresponding/similar aspect of the invention. For example, where an aspect object A comprises element B, readers will understand that a corresponding aspect is implicitly disclosed, which provides object A lacking element B.

The invention claimed is:

1. A device for delivering gas to a user comprising a mouthpiece component, the mouthpiece component comprising (1) a contoured and flexible mouthguard component that comprises (a) a gas inlet that is configured to receive a first gas flow from a highly portable gas container that weighs less than 1.25 pounds when filled with a breathable gas comprising 92.8-98.4% oxygen, (b) a gas outlet through which gas can flow out of the mouthguard component and into the mouth of a conscious user or unconscious or semi-conscious treated person when the mouthguard component is placed into the mouth of the user or the treated person, and (c) at least right rear and left rear teeth engagement elements, (2) an engagement component that is configured to releasably and sealingly engage the gas container, (3) a transition element that (a) comprises a gas flow path that facilitates the flow of the first gas from the gas container to the inlet of the mouthguard component when the engagement component engages the gas container and the first gas is released from the gas container, (b) maintains a stable shape in use such that the position of the mouthguard component relative to the gas container is constant when the engagement component engages the gas container, and (c) comprises an access port that is configured to engage a secondary inlet component that comprises a secondary flow path for delivering a gas to the user or treated person from a gas source that is different than the gas container, and (d) directly engages the gas container, and (4) a variable inlet component that (a) is configured to receive a secondary gas flow that is independent of the flow of the first gas from the gas container to the mouthpiece component (i) at the same time that the first gas flows from the gas and (b) is configured such that the secondary gas flow can selectively originate from (i) a human assistant breathing breath into the variable inlet component or.

2. The device of claim 1, wherein the variable inlet component comprises a one-way valve that prevents the flow of gas from the user or the treated person to the source of the secondary gas flow.

3. The device of claim 2, wherein the variable inlet component is selectively releasable from the device.

4. The device of claim 3, wherein at least a portion of the variable inlet component is selectively and reversibly collapsible lengthwise and compressible in diameter or width.

5. The device of claim 4, wherein the variable inlet component comprises a first contoured variable inlet portion comprising an arched shape that is maintained when the device is at rest and a discrete, second noncontoured variable inlet portion that is positioned distally to the gas container.

6. The device of claim 5, wherein (1) the first variable inlet portion and second variable inlet portion are configured to be selectively separable from each other, and (2) the device is configured to receive breaths or the second gas through some or all of the variable inlet component when (a) both the first variable inlet portion and second variable inlet portion are connected and (b) when the second variable inlet portion is separated from the first variable inlet portion.

7. The device of claim 5, wherein the first collapsible contoured variable constitutes 20-80% of the length of the variable inlet component.

8. The device of claim 7, wherein the device is configured so that it can be used in a hands-free manner when inserted into a user's mouth.

9. The device of claim 4, wherein the length of the variable inlet component is configured to be reversibly collapsible by at least 15% of the resting length of the variable inlet component.

10. The device of claim 9, wherein the variable inlet component comprises a collapsible and compressible portion with a length of 3.5-7 inches.

11. The device of claim 3, wherein the gas container is engaged with the engagement component.

12. The device of claim 11, wherein the gas container comprises a selectable gas release component that, when operated, delivers the first gas from the gas container through the transition element and through the mouthguard component in a pulse delivery manner.

13. The device of claim 12, wherein the gas container, when not engaged by the engagement component, is independently operable as a gas delivery device and comprises its own mouthpiece component through which the user may receive the first gas when the gas container is separated from the rest of the device, and wherein the device lacks any mask component.

14. A method of delivering a gas to a treated person, the method comprising (1) causing the treated person to engage a device of claim 13 by placing the mouthguard component into the mouth of the treated person such that the mouthguard is sealed within the mouth of the treated person, (2) the assistant operating the gas release component to deliver the first gas to the treated person, and (3) the assistant breathing breath into the variable inlet component to deliver breath to the treated person.

15. The method of claim 14, wherein the method comprises the assistant (1) closing off the nose of the treated person during at least part of the method, (2) delivering one or more other elements or compounds to the treated person, or (3) performing both (1) and (2).

16. The method of claim 14, wherein the method is performed on a treated person who is unconscious during at least a part of the method.

17. The method of claim 16, wherein the device is maintained in the mouth of the unconscious user without any further support during the method.

18. The method of claim 16, wherein the treated person is a person who is known to have an infection or is suspected to have an infection.

19. The method of claim 16, wherein the treated person is a person who is known to have saliva containing harmful saliva-transmissible chemicals or is suspected of having saliva containing harmful saliva-transmissible chemicals.

20. The method of claim 14, wherein the method comprises concurrently delivering both gas from the gas container and breath from the assistant through the variable inlet component.

21. The method of claim 20, wherein the method comprises the assistant collapsing a collapsible portion of the variable inlet component by at least 15% of its resting length before breathing into the variable inlet component.

22. The method of claim 14, wherein the method comprises the assistant collapsing a collapsible portion of the variable inlet component by at least 15% of its resting length before breathing into the variable inlet component.

23. The method of claim 14, wherein the method comprises applying suction through a portion of the variable inlet component or permitting the treated person to exhale through a portion of the variable inlet component.

24. The method of claim 14, wherein the method comprises the assistant monitoring the breathing of the treated person and, based on the breathing condition of the treated person, either delivering gas from the gas container, breathing through the variable inlet tube, or both.

25. The device of claim 3, wherein when the variable inlet component is removed from the device, no portion of the device extends beyond the diameter or width of the gas container.

26. The device of claim 1, wherein the mouthguard component comprises separated right and left rear teeth engagement elements that are positioned adjacent to the gas outlet, and the transition element is in direct contact with both the mouthpiece component and the gas container.

27. The device of claim 2, wherein the variable inlet component is.

28. The device of claim 27, wherein the variable inlet component is configured to selectively permit the user or the treated person to exhale through a portion of the variable inlet component.

29. The device of claim 27, wherein the device is configured to selectively engage a device that applies a suction force which is applied through a portion of the variable inlet component.

* * * * *

UNITED STATES PATENT AND TRADEMARK OFFICE
CERTIFICATE OF CORRECTION

PATENT NO. : 12,090,276 B1  
APPLICATION NO. : 18/509316  
DATED : September 17, 2024  
INVENTOR(S) : Minogue et al.

Page 1 of 1

It is certified that error appears in the above-identified patent and that said Letters Patent is hereby corrected as shown below:

In the Claims

At Column 80, Claim number 1, Line numbers 7-10, should read "time that the first gas flows from the gas container to the mouthpiece component and (ii) when there is no flow of the first gas from the gas container to the mouthpiece component and (b) is configured such that the secondary gas flow can selectively originate from (i) a human assistant breathing breath into the variable inlet component or (ii) a source of a second gas that selectively engages the variable inlet component."

At Column 80, Claim number 7, Line 35, should read "The device of claim 5 wherein the first . . ."

Signed and Sealed this  
Eleventh Day of March, 2025

Coke Morgan Stewart  
*Acting Director of the United States Patent and Trademark Office*